United States Patent
Zivkovic et al.

(10) Patent No.: US 8,556,854 B2
(45) Date of Patent: Oct. 15, 2013

(54) DUAL CHAMBER SYRINGE WITH RETRACTABLE NEEDLE

(75) Inventors: Ivan Zivkovic, Pleasantville, NY (US); Jorgen Hager, Helsingborg (SE); Ulf Handberg, Upplands Vasby (SE); Gert Hanner, Hoganas-Mjohult (SE); Thomas Holma, Svangsta (SE); Ulf Wahlberg, Helsingborg (SE)

(73) Assignee: Becton, Dickinson and Company, Franklin Lakes, NJ (US)

( * ) Notice: Subject to any disclaimer, the term of this patent is extended or adjusted under 35 U.S.C. 154(b) by 6 days.

(21) Appl. No.: 13/187,101

(22) Filed: Jul. 20, 2011

(65) Prior Publication Data
US 2012/0029427 A1 Feb. 2, 2012

Related U.S. Application Data

(60) Provisional application No. 61/366,874, filed on Jul. 22, 2010.

(51) Int. Cl.
*A61M 5/00* (2006.01)

(52) U.S. Cl.
USPC ............................................. 604/110

(58) Field of Classification Search
USPC .................. 604/181, 183, 187, 195, 198
See application file for complete search history.

(56) References Cited

U.S. PATENT DOCUMENTS

| | | |
|---|---|---|
| 857,739 A | 6/1907 | Kennerly et al. |
| 1,930,929 A | 10/1933 | Eisenberg |
| 3,572,556 A | 3/1971 | Pogacar |
| 3,978,846 A | 9/1976 | Bailey |
| 4,284,077 A | 8/1981 | Wagner |
| 4,375,815 A | 3/1983 | Burns |
| 4,388,925 A | 6/1983 | Burns |
| 4,449,529 A | 5/1984 | Burns |
| 4,527,561 A | 7/1985 | Burns |
| 4,535,769 A | 8/1985 | Burns |
| 4,553,541 A | 11/1985 | Burns |
| 4,616,649 A | 10/1986 | Burns |
| 4,624,253 A | 11/1986 | Burns |
| 4,677,979 A | 7/1987 | Burns |
| 4,747,830 A | 5/1988 | Gloyer et al. |
| 4,941,883 A | 7/1990 | Venturini |
| 5,431,672 A | 7/1995 | Cote et al. |
| 5,533,970 A | 7/1996 | Berger et al. |
| 5,578,011 A | 11/1996 | Shaw |

(Continued)

FOREIGN PATENT DOCUMENTS

| | | |
|---|---|---|
| WO | WO-96/35463 | 11/1996 |
| WO | WO-98/48869 | 11/1998 |
| WO | WO-03/090815 | 11/2003 |

OTHER PUBLICATIONS

PCT International Search Report & Written Opinion in PCT/US2011/044834, mailed Mar. 9, 2012, 16 pgs.

(Continued)

*Primary Examiner* — Aarti B Berdichevsky
(74) *Attorney, Agent, or Firm* — Servilla Whitney LLC

(57) ABSTRACT

Embodiments of a retractable syringe assembly are provided that include a dual syringe barrel configuration. One or more embodiments include reuse prevention features and features that prevent premature activation of the retraction mechanism. Methods for aspirating and expelling liquid from medical devices are also provided.

24 Claims, 67 Drawing Sheets

(56) References Cited

U.S. PATENT DOCUMENTS

| | | |
|---|---|---|
| 5,632,733 A | 5/1997 | Shaw |
| 5,709,667 A | 1/1998 | Carilli |
| 5,752,968 A | 5/1998 | Jolly et al. |
| 5,792,162 A | 8/1998 | Jolly et al. |
| 5,797,880 A | 8/1998 | Erskine |
| 5,830,190 A | 11/1998 | Howell |
| 5,919,201 A | 7/1999 | Carter et al. |
| 5,938,676 A | 8/1999 | Cohn et al. |
| 5,941,892 A | 8/1999 | Cohn et al. |
| 6,010,486 A | 1/2000 | Carter et al. |
| 6,024,726 A | 2/2000 | Hill |
| 6,036,674 A | 3/2000 | Caizza et al. |
| 6,053,929 A | 4/2000 | Cohn et al. |
| 6,086,568 A | 7/2000 | Caizza |
| 6,090,077 A | 7/2000 | Shaw |
| 6,177,037 B1 | 1/2001 | Mayer |
| 6,183,440 B1 | 2/2001 | Bell |
| 6,221,052 B1 | 4/2001 | Caizza et al. |
| 6,277,102 B1 | 8/2001 | Carilli |
| 6,368,303 B1 | 4/2002 | Caizza |
| 6,409,701 B1 | 6/2002 | Cohn et al. |
| 6,413,237 B1 | 7/2002 | Caizza et al. |
| 6,432,087 B1 | 8/2002 | Hoeck et al. |
| 6,517,516 B1 | 2/2003 | Caizza |
| 6,558,357 B1 | 5/2003 | Hoeck |
| 6,585,690 B1 | 7/2003 | Hoeck et al. |
| 6,589,209 B1 | 7/2003 | Dysarz |
| 6,599,268 B1 | 7/2003 | Townsend et al. |
| 6,632,198 B2 | 10/2003 | Caizza |
| 6,689,106 B2 | 2/2004 | Bush, Jr. et al. |
| 6,776,776 B2 | 8/2004 | Alchas et al. |
| 6,840,291 B2 | 1/2005 | Caizza et al. |
| 6,926,700 B2 | 8/2005 | Bressler et al. |
| 6,932,803 B2 | 8/2005 | Newby |
| 6,952,604 B2 | 10/2005 | DeNuzzio et al. |
| 7,018,344 B2 | 3/2006 | Bressler et al. |
| 7,083,599 B2 | 8/2006 | Alchas et al. |
| 7,108,675 B2 | 9/2006 | Deboer et al. |
| 7,182,734 B2 | 2/2007 | Saulenas et al. |
| 7,258,678 B2 | 8/2007 | Wilkinson et al. |
| 7,294,118 B2 | 11/2007 | Saulenas et al. |
| 7,344,517 B2 | 3/2008 | Schiller |
| 7,351,224 B1 | 4/2008 | Shaw |
| 7,426,408 B2 | 9/2008 | DeNuzzio et al. |
| 7,597,684 B2 | 10/2009 | Alchas et al. |
| 7,604,613 B2 | 10/2009 | Crawford et al. |
| 7,713,245 B2 | 5/2010 | Cipoletti et al. |
| 7,803,132 B2 * | 9/2010 | Janek et al. .......... 604/110 |
| 2002/0068907 A1 | 6/2002 | Dysarz |
| 2002/0082560 A1 | 6/2002 | Yang |
| 2002/0165501 A1 | 11/2002 | Yang |
| 2003/0125676 A1 | 7/2003 | Swenson et al. |
| 2003/0125677 A1 | 7/2003 | Swenson et al. |
| 2003/0163096 A1 | 8/2003 | Swenson et al. |
| 2003/0181867 A1 | 9/2003 | Bressler et al. |
| 2004/0204688 A1 | 10/2004 | Lin et al. |
| 2005/0215951 A1 | 9/2005 | Saulenas et al. |
| 2006/0129173 A1 | 6/2006 | Wilkinson |
| 2006/0189935 A1 * | 8/2006 | Janek et al. .......... 604/110 |
| 2007/0129675 A1 | 6/2007 | Summerville et al. |
| 2007/0260193 A1 | 11/2007 | Chin et al. |
| 2008/0097344 A1 | 4/2008 | McKinnon et al. |
| 2008/0243075 A1 | 10/2008 | Shaw |
| 2008/0262423 A1 | 10/2008 | Ingram et al. |
| 2009/0048560 A1 | 2/2009 | Caizza et al. |
| 2009/0131869 A1 | 5/2009 | Caizza et al. |
| 2012/0022464 A1 * | 1/2012 | Zivkovic et al. .......... 604/198 |
| 2012/0029427 A1 * | 2/2012 | Zivkovic et al. .......... 604/110 |
| 2012/0071827 A1 * | 3/2012 | Zivkovic et al. .......... 604/110 |
| 2012/0078225 A1 * | 3/2012 | Zivkovic et al. .......... 604/506 |

OTHER PUBLICATIONS

"Non-Final Office Action in U.S. Appl. No. 13/187,136", Dec. 13, 2012, 15 pgs.

* cited by examiner

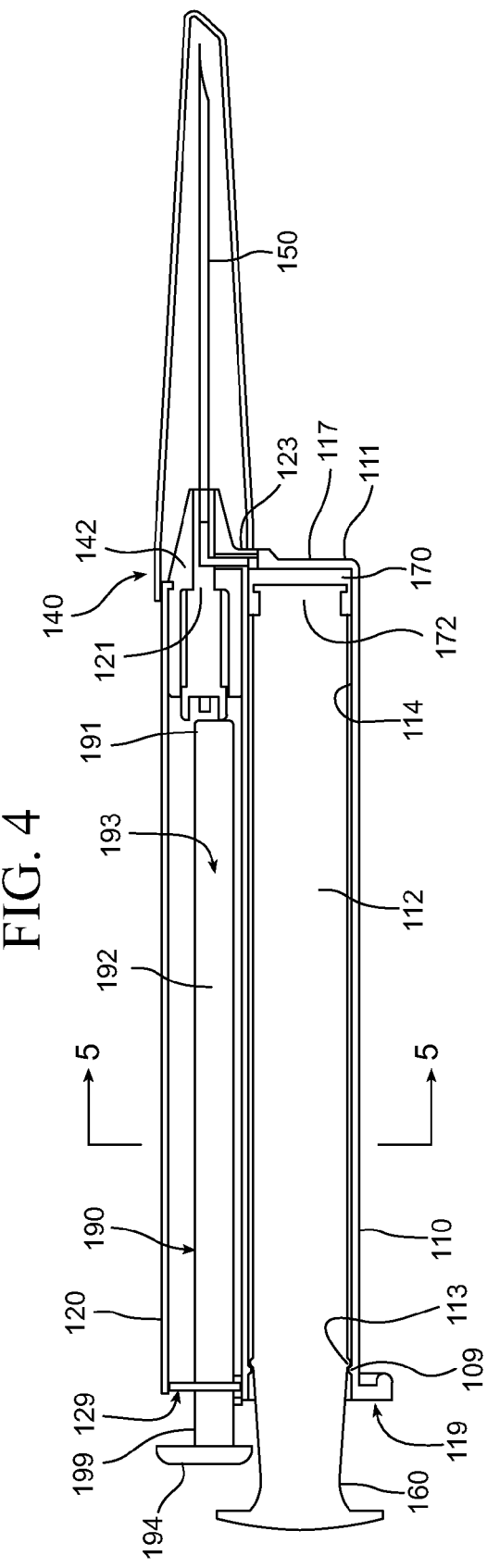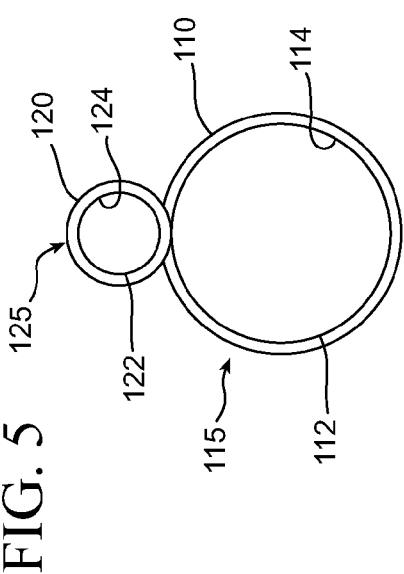

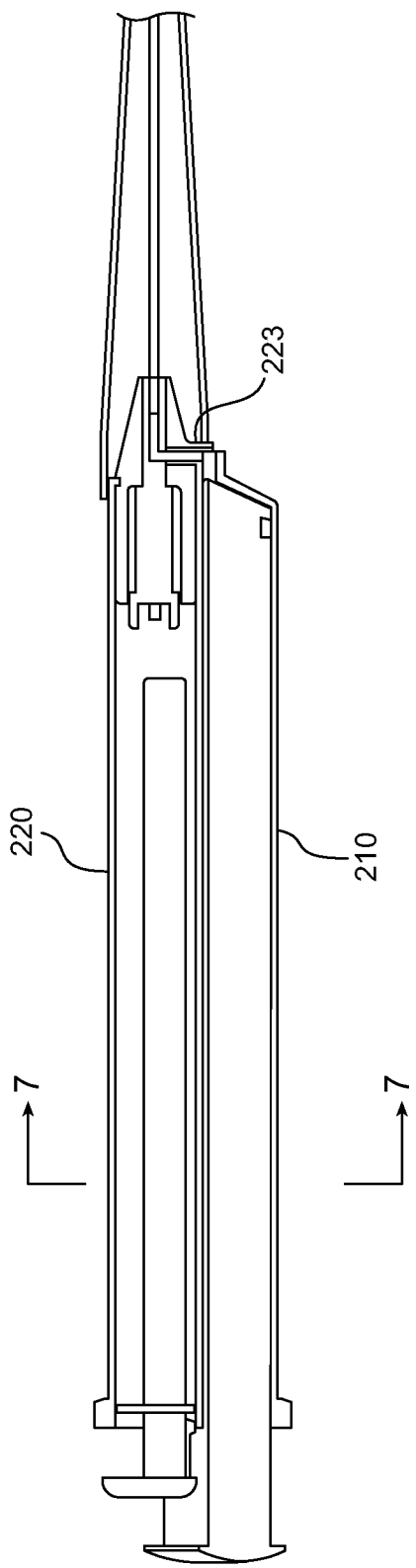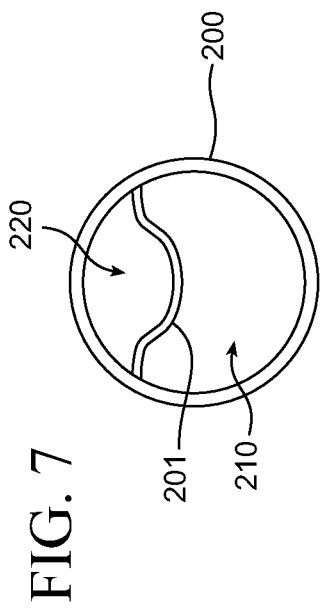

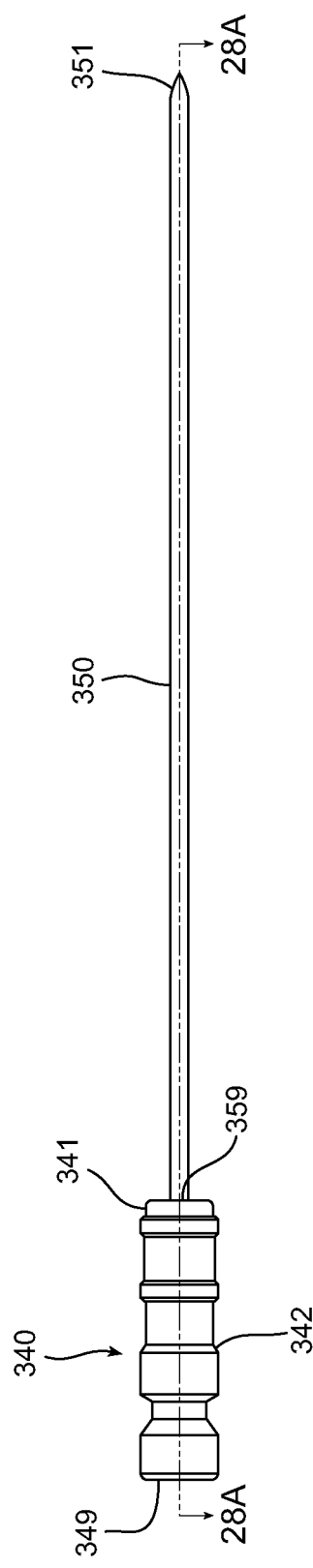
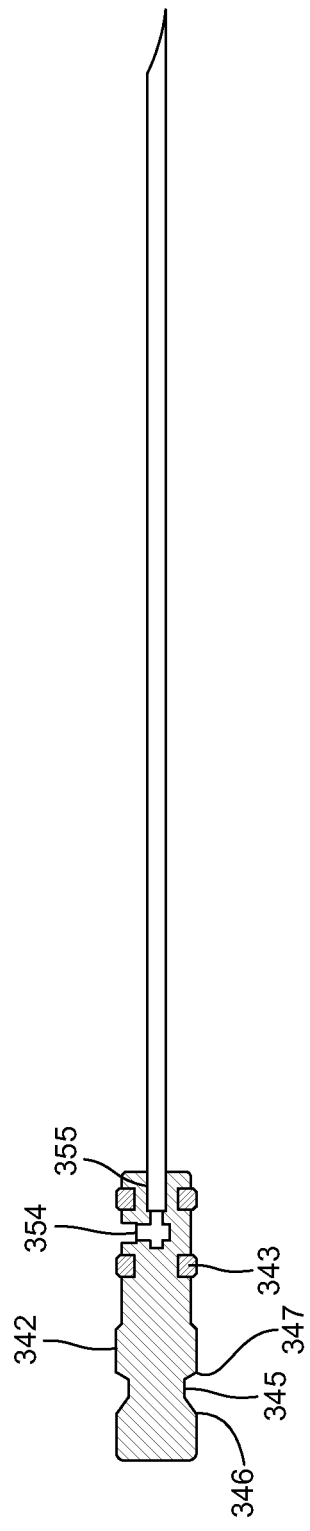
FIG. 28
FIG. 28A

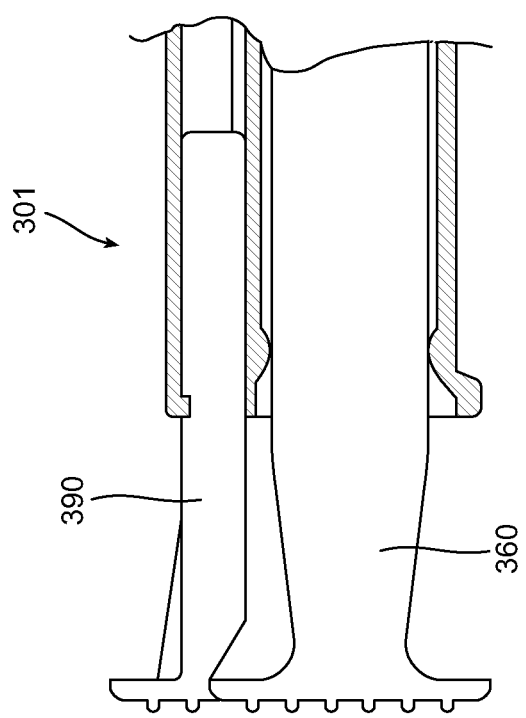

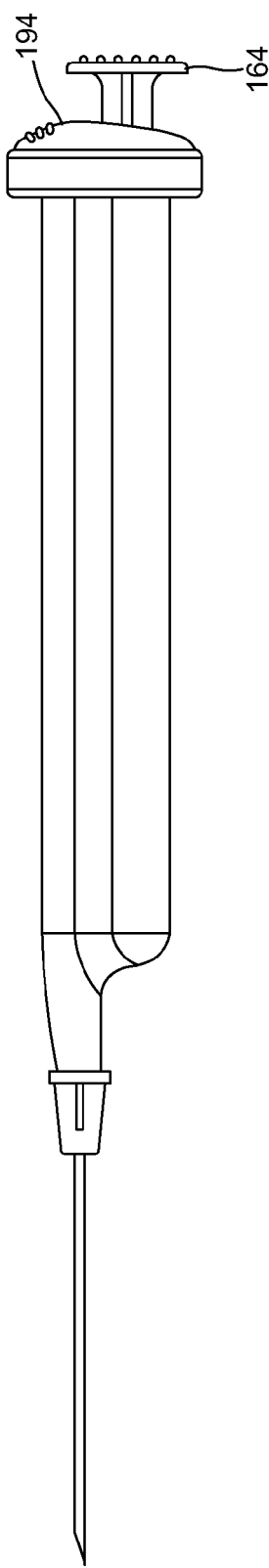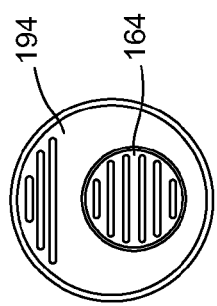
FIG. 39A
FIG. 39B

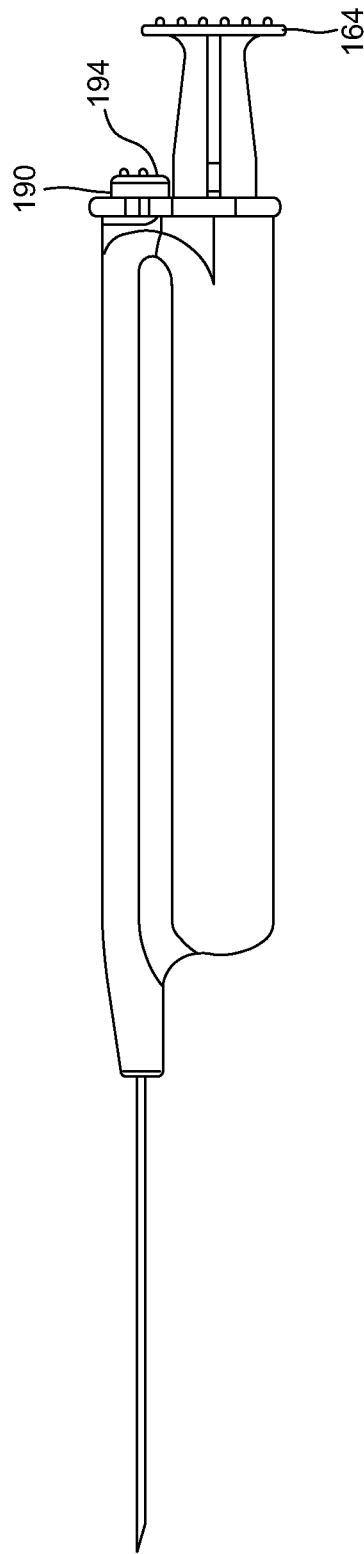
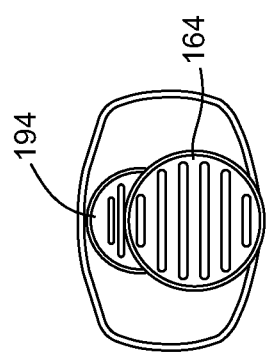

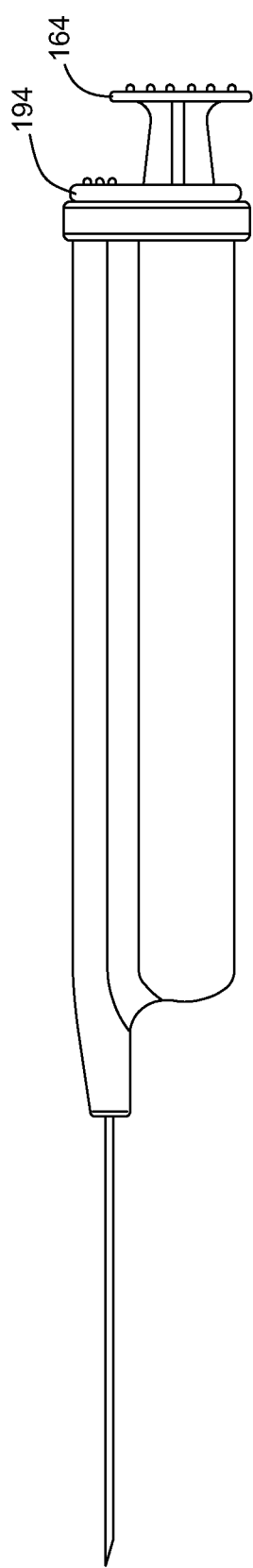
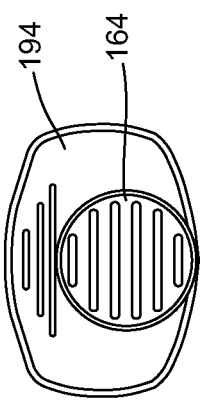
FIG. 46
FIG. 47

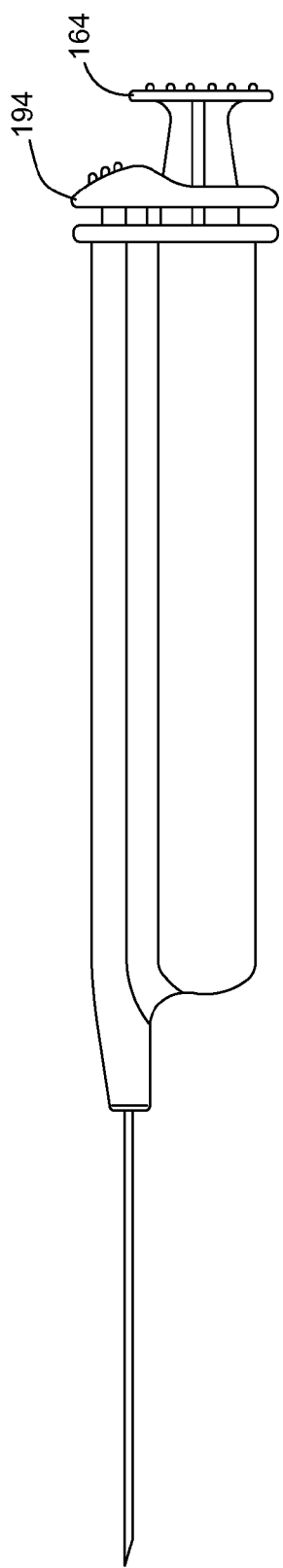
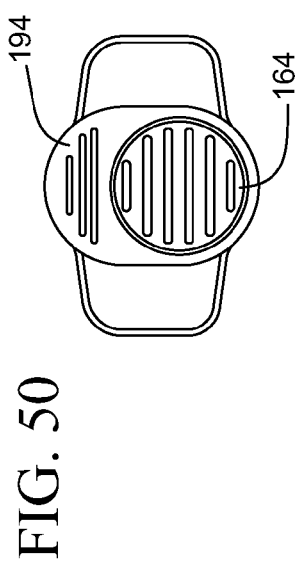
FIG. 49
FIG. 50

DUAL CHAMBER SYRINGE WITH RETRACTABLE NEEDLE

CROSS-REFERENCE TO RELATED APPLICATIONS

This application claims priority under 35 U.S.C. §119(e) to U.S. Provisional Application No. 61/366,874, filed Jul. 22, 2010, the disclosures of which are incorporated herein by reference in their entirety.

TECHNICAL FIELD

Aspects of the present invention relate to syringe assemblies that include a retractable needle and reuse prevention features and methods of using such syringe assemblies.

BACKGROUND

Needle retraction features have been incorporated into syringe assemblies to protect users from needle stick injuries. In conventional assemblies, the needle hub assemblies, including a needle cannula, are attached to the syringe barrel and must be withdrawn into the syringe barrel by a user or by a retraction feature. Alternatively, a needle shield may be placed over the needle cannula by the user or otherwise.

In conventional syringe assemblies in which the needle hub assemblies are retracted into the syringe barrel by a retraction feature, the retraction feature is often provided within the syringe barrel and/or the plunger rod disposed within the syringe barrel. Specifically, the plunger rod may include a chamber that houses the needle hub after it is retracted. The retraction feature typically includes a cutting element disposed between the plunger rod and the stopper that is used to open the stopper after the contents of the syringe barrel are expelled, to expose the chamber of the plunger rod to receive the retracted needle hub. A spring is often incorporated in the needle hub assemblies to drive the retraction of the needle hub into the plunger rod.

Accordingly, such retraction features require cutting, breaking, piercing or other force-intensive mechanical action for activation and, thus, increased complexity to enable the sealed plunger and stopper to be breached during activation. Further, as most conventionally designed retractable needles are activated after dosing by continued pressure on the rear of the plunger rod, inadvertent activation of the retraction feature may occur since the same forces must be applied when expelling the contents of the syringe barrel. Moreover, some devices may be inadvertently activated during dosing if sufficient pressure is generated during expulsion of the contents of the syringe, for example, when the medication is viscous and requires the user to apply additional pressure or force to the plunger rod, which exceeds the force required to activate the retraction feature. Premature activation is especially problematic in applications where high forces are applied to the plunger rod, for example, during high speed injections.

The retraction features of conventional syringe barrels that are plunger-activated must withstand increased syringe pressures and associated increase in force applied to the plunger rod, as described above. These increased forces and pressure lead to a requirement for large activation forces which could exceed the operational forces in order to prevent premature activation. Since most conventional syringe barrels employ an additional plunger motion after full dispensing, and in the same manner as the dispensing motion, a threshold force must be used to allow the user to differentiate between a fully bottomed plunger and the activation of the retraction feature. The threshold force may be difficult to ascertain and maintain separately from the force applied to the plunger rod to expel the contents of the syringe barrel. Further, proper application of the threshold force may require a user to position the syringe barrel and the needle cannula at an increased angle to the patient's skin, instead of positioning the syringe barrel and needle cannula substantially parallel to the patient's skin. The additional force required to activate the retraction feature may cause additional pressure to be generated at the stopper or other removable opening in the plunger rod, which may be sufficient to cause the stopper and/or plunger rod to malfunction.

In conventional retractable syringe assemblies where the retraction feature and the subsequent housing of the needle hub are contained within the fluid path, the retraction feature and housing may cause a volume of medication to become trapped within the syringe barrel, thereby increasing waste and potentially affecting dosing accuracy. Further, a portion of the trapped medication may be expelled during the activation of the retraction feature causing splatter, if the retraction feature is activated when the needle cannula is outside of the patient, or an unintended increase in the dose administered to the patient, if the retraction feature is activated when the needle cannula is in the patient. Placement of the retraction feature within the syringe barrel may also cause trapped air to remain in the syringe barrel when purging or priming the syringe. This can lead to the possibility of injected air. The size of the syringe barrel must also accommodate the retraction feature and the needle hub assembly that will be housed therein after retraction.

In syringe assemblies which do not house the retraction feature within the fluid path, the retraction feature is often disposed at a location that requires the user to change their grip of the syringe assembly to activate the retraction feature. Such designs may not be ergonomically acceptable to certain users of these syringe assemblies.

Conventional retraction syringe assemblies often do not incorporate reuse prevention features, and thus, the retraction mechanism may be reset so the syringe barrel may be reused. The reuse of syringe assemblies without sterilization or sufficient sterilization is believed to facilitate the transfer of contagious diseases.

Accordingly, it would be desirable to provide a retractable syringe assembly with a retraction feature that does not interfere with normal operation of the syringe assembly and reduces the risk of premature activation or the retraction mechanism. It would also be desirable to provide a retractable syringe assembly which incorporates a reuse prevention feature.

SUMMARY OF THE INVENTION

One aspect of the present invention pertains to a syringe assembly comprising a fluid barrel including a sidewall having an inside surface defining a fluid chamber for retaining fluid and having a first cross-sectional width, an open proximal end and a distal end including a distal wall; a plunger rod disposed within the fluid chamber comprising a distal end, a proximal end, a plunger rod body extending from the distal end to the proximal end, and a stopper disposed at the distal end of the plunger rod for forming a fluid-tight seal with the inside surface of the barrel; a retraction barrel disposed adjacent to the sidewall of the fluid barrel, the retraction barrel including a wall having an interior surface defining a needle chamber, an open proximal end, an open distal end including a barrier wall, an aperture between the wall of the retraction barrel and the sidewall of the fluid barrel permitting fluid communication between the fluid chamber and the needle chamber and a needle hub assembly comprising a needle hub, a needle cannula attached to the needle hub, the needle cannula being in fluid communication with the aperture and biased to move in a proximal direction; and a trigger element disposed within the needle chamber and moveable within the retraction barrel independently from the plunger rod, wherein the trigger element includes a proximal end, a free and open distal end that provides the trigger force, and a trigger element body extending from the proximal end to the distal end and including an interior surface defining a hollow interior, the trigger element providing a trigger force causing the needle cannula to retract into the retraction barrel.

In one or more embodiments of the present invention, the inside surface of the fluid chamber sidewall includes a retaining ring adjacent to the proximal end defining a second cross-sectional width that is less than the first cross-sectional width, and the plunger rod body includes a flexible protrusion having a cross-sectional width greater than the cross-sectional width of the barrel at the rib and a frangible portion. In one or more embodiments of the present invention, contact between the stopper and the distal wall of the barrel causes the protrusion to advance distally past the rib in the barrel and lock the plunger rod in the barrel to prevent reuse of the syringe assembly. In one or more embodiments of the present invention, the distal end of the plunger rod includes a stopper-engaging portion and the stopper is attached to the stopper-engaging portion of the plunger rod, the stopper being distally and proximally movable relative to the stopper-engaging portion for a pre-selected axial distance such that when a force is applied to the plunger rod in the distal direction and the distal end of the stopper is in contact with the distal wall of the barrel, the protrusion is permitted to advance distally past the rib in the barrel and lock the plunger rod in the barrel to prevent reuse of the syringe assembly. In one or more embodiments of the present invention, continuous application of a force on the plunger rod in the proximal direction after the protrusion has advanced distally past the rib causes the frangible portion to break. In one or more embodiments of the present invention, continuous application of a force on the plunger rod in the proximal direction after the protrusion has advanced distally past the rib causes the frangible portion to break.

In one or more embodiments of the present invention, the needle hub assembly of the syringe assembly is disposed at the open distal end of the retraction barrel and includes a frangible element for exerting a force on the needle cannula support in the distal direction. In one or more embodiments of the present invention, application of a force in the distal direction to the trigger element provides the trigger force on the needle hub assembly to break the frangible element so the needle cannula is retracted into the retraction barrel. In one or more embodiments of the present invention, the needle cannula is biased by a spring disposed between the needle hub and the barrier wall that exerts a force on the needle hub in a proximal direction.

In one or more embodiments of the present invention, the needle cannula is retracted into the retraction barrel, it is housed within the hollow interior of the trigger element.

In one or more embodiments of the present invention, the open distal end of the retraction barrel comprises a securing element for securing the needle hub assembly to the retraction barrel and the needle hub assembly includes an attachment element that engages the securing element, the engagement of the attachment element and the securing element being activated by a needle shield disposed on the needle hub. In one or more embodiments of the present invention, engagement of the securing element and the attachment element permits fluid communication between the aperture and the needle cannula. In one or more embodiments of the present invention, the needle shield may be removed from the needle hub upon engagement of the attachment element and the securing element. In one or more embodiments of the present invention, the securing element of the retraction barrel comprises at least one opening in the wall of the retraction barrel extending in a distal direction from the open distal end and the attachment element comprises at least one radially outwardly extending tab disposed on the needle hub for engaging the at least one opening. In one or more embodiments of the present invention, the needle hub comprises an open conduit for permitting fluid communication between the needle cannula and the aperture and the engagement of the tab of the needle hub and the opening of the retraction barrel permits alignment of the open conduit and the aperture.

In one or more embodiments of the present invention, the needle hub comprises a distal end, a proximal end and a hub body extending from the distal end to the proximal end, the hub body including an outside surface and at least one finger element disposed along an outside surface, the finger element extending outwardly from the outside surface of the hub body and including a distal end attached the outside surface of the needle hub and a free proximal end that is unattached to the needle hub. In one or more embodiments of the present invention, the needle shield comprises a closed distal end, an open proximal end and a hollow body defining an cavity for receiving the needle hub, the hollow body including an interior surface comprising a plurality of detents that extend inwardly and engage the at least one finger of the needle hub to rotate the needle hub with respect to the securing element to attach the needle hub to the open distal end of the retraction barrel. In one or more embodiments of the present invention, the plurality of detents apply a rotational force to the at least one finger or the needle hub to engage the finger and permit rotation of the needle hub.

In one or more embodiments of the present invention, the inside surface of the fluid chamber sidewall includes a retaining ring adjacent to the proximal end defining a second cross-sectional width that is less than the first cross-sectional width and the plunger rod body includes a flexible protrusion having a cross-sectional width greater than the cross-sectional width of the barrel at the rib and a frangible portion. In one or more embodiments of the present invention, contact between the stopper and the distal wall of the barrel causes the protrusion to advance distally past the rib in the barrel and lock the plunger rod in the barrel to prevent reuse of the syringe assembly. In one or more embodiments of the present invention, the distal end of the plunger rod includes a stopper-engaging portion and the stopper is attached to the stopper-engaging portion of the plunger rod, the stopper being distally and proximally movable relative to the stopper-engaging portion for a pre-selected axial distance such that when a force is applied to the plunger rod in the distal direction and the distal end of the stopper is in contact with the distal wall of the barrel, the protrusion is permitted to advance distally past the rib in the barrel and lock the plunger rod in the barrel to prevent reuse of the syringe assembly. In one or more embodiments of the present invention, continuous application of a force on the plunger rod in the proximal direction after the protrusion has advanced distally past the rib causes the frangible portion to break. In one or more embodiments of the present invention, continuous application of a force on the plunger rod in the proximal direction after the protrusion has advanced distally past the rib causes the frangible portion to break.

In one or more embodiments of the present invention, the needle chamber has a cross sectional width that is less than the first cross-sectional width.

Yet another embodiment of the present invention pertains to a syringe assembly comprising a barrel comprising including an open proximal end, sidewall having an inside surface defining a fluid chamber for retaining fluid and having a first cross-sectional width and a needle chamber for housing a needle hub assembly, the fluid chamber and the needle chamber being divided by a barrier wall having a first aperture permitting fluid communication between the fluid chamber and the needle chamber; a needle hub assembly disposed within the needle chamber, the needle hub assembly comprising a needle hub, a needle cannula supported within the needle hub by a frangible connection, the needle cannula in fluid communication with the first aperture and biased to move in a proximal direction; a plunger rod disposed within the fluid chamber comprising a distal end, a proximal end, a stopper disposed at the distal end of the plunger rod for forming a fluid-tight seal with the inside surface of the barrel and a plunger rod body extending from the distal end to the proximal end; and a retraction rod disposed within the needle chamber, the retraction rod including a proximal end and an open distal end for breaking the frangible connection of the needle hub assembly upon application of a distally directed force to the retraction rod and causing the needle cannula to retract and be retracted within the retraction rod.

In one or more embodiments of the present invention, the syringe assembly further comprises a needle shield disposed on the needle hub for attaching the needle hub assembly to the retraction barrel. In one or more embodiments of the present invention, the needle shield provides tactile indication of attachment of the needle hub assembly to the retraction barrel. In one or more embodiments of the present invention, the needle shield permits removal of the needle hub assembly from the retraction barrel.

In one or more embodiments of the present invention, attachment of the needle hub assembly to the retraction barrel permits fluid communication between the aperture and the needle cannula.

In one or more embodiments of the present invention, the inside surface of the fluid chamber sidewall includes a retaining ring adjacent to the proximal end defining a second cross-sectional width that is less than the first cross-sectional width and the plunger rod body includes a flexible protrusion having a cross-sectional width greater than the cross-sectional width of the barrel at the rib and a frangible portion. In one or more embodiments of the present invention, the contact between the stopper and the distal wall of the barrel causes the protrusion to advance distally past the rib in the barrel and lock the plunger rod in the barrel to prevent reuse of the syringe assembly.

In one or more embodiments of the present invention, the distal end of the plunger rod includes a stopper-engaging portion and the stopper is attached to the stopper-engaging portion of the plunger rod, the stopper being distally and proximally movable relative to the stopper-engaging portion for a pre-selected axial distance such that when a force is applied to the plunger rod in the distal direction and the distal end of the stopper is in contact with the distal wall of the barrel, the protrusion is permitted to advance distally past the rib in the barrel and lock the plunger rod in the barrel to prevent reuse of the syringe assembly. In one or more embodiments of the present invention, continuous application of a force on the plunger rod in the proximal direction after the protrusion has advanced distally past the rib causes the frangible portion to break. In one or more embodiments of the present invention, continuous application of a force on the plunger rod in the proximal direction after the protrusion has advanced distally past the rib causes the frangible portion to break.

In one or more embodiments of the present invention, the needle barrel has a cross sectional width that is less than the first cross-sectional width.

BRIEF DESCRIPTION OF THE DRAWINGS

FIG. 4 illustrates a side cross-sectional view of the syringe assembly shown in FIG. 1, wherein the retraction barrel is located outside of the fluid barrel;

FIG. 5 illustrates a cross-sectional view of the fluid barrel and the retraction barrel taken along lines 5-5, with the trigger element and plunger rod removed from the assembly;

FIG. 6 illustrates a side cross-sectional view of the syringe assembly according to one or more embodiments, wherein the retraction barrel is nested within the fluid barrel;

FIG. 7 illustrates a cross-sectional view of the fluid barrel and the retraction barrel taken along lines 7-7;

FIG. 28 illustrates a side view of the needle hub assembly shown in FIG. 24;

FIG. 28A illustrates a cross-sectional view of the needle hub assembly shown in FIG. 28 taken along line A-A;

FIG. 29 illustrates a partial, cross-sectional view of a retractable syringe assembly showing the proximal end according to one or more embodiments;

FIG. 39A illustrates a side view of the retractable syringe assembly shown in FIG. 39;

FIG. 39B illustrates a view of the retractable syringe assembly shown in FIG. 39 taken from the proximal end;

FIG. 41 illustrates a side view of the retractable syringe assembly shown in FIG. 40;

FIG. 42 illustrates a view of the retractable syringe assembly shown in FIG. 40 taken from the proximal end;

FIG. 46 illustrates a side view of the retractable syringe assembly shown in FIG. 45;

FIG. 47 illustrates a view of the retractable syringe assembly shown in FIG. 45 taken from the proximal end;

FIG. 49 illustrates a side view of the retractable syringe assembly shown in FIG. 48;

FIG. 50 illustrates a view of the retractable syringe assembly shown in FIG. 48 taken from the proximal end;

DETAILED DESCRIPTION

Figure 1:
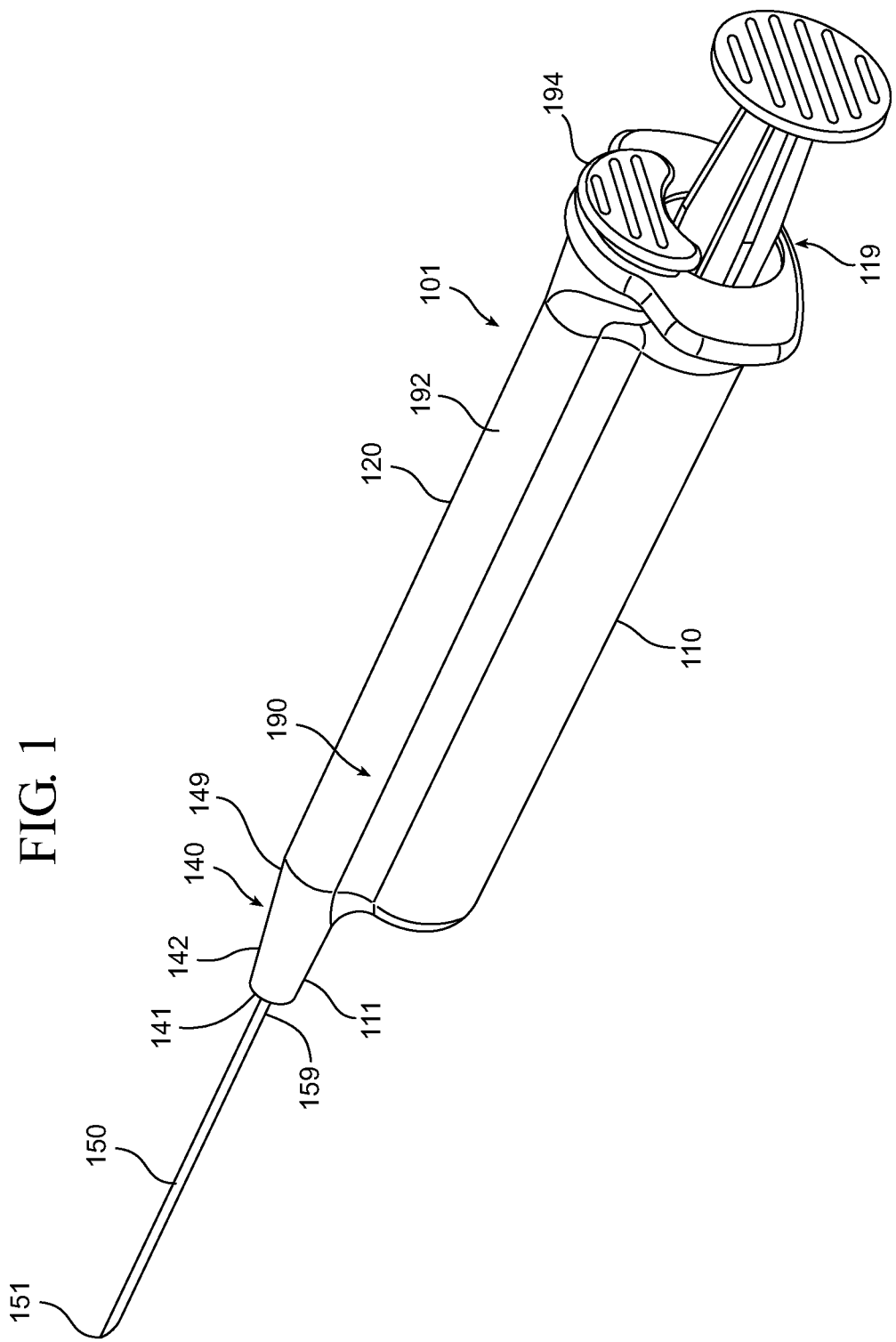
FIG. 1 illustrates a perspective view a retractable syringe assembly according to one or more embodiments of the present invention.
Figure 2:
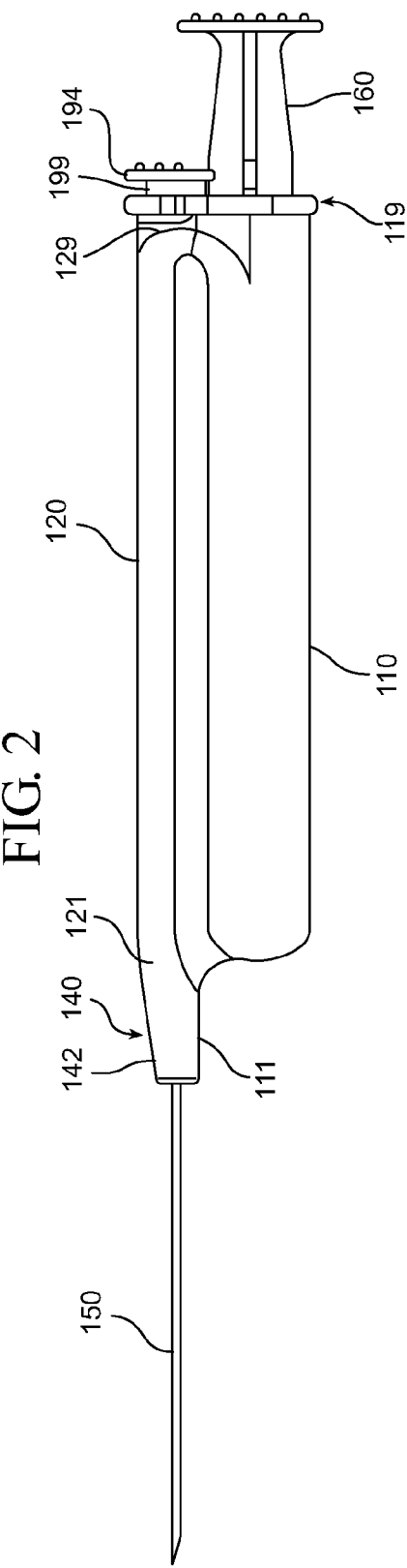
FIG. 2 illustrates a side view of the syringe assembly shown in FIG. 1.
Figure 3:
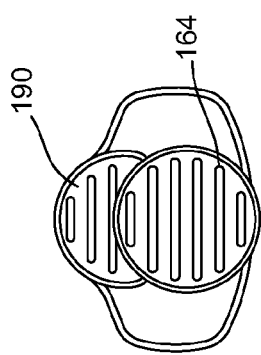
FIG. 3 illustrates a view of the syringe assembly shown in FIG. 1 from the proximal end of the syringe assembly.

Before describing several exemplary embodiments of the invention, it is to be understood that the invention is not limited to the details of construction or process steps set forth in the following description. The invention is capable of other embodiments and of being practiced or being carried out in various ways.

In this disclosure, a convention is followed wherein the distal end of the device is the end closest to a patient and the proximal end of the device is the end away from the patient and closest to a practitioner.

Aspects of the invention pertain to retractable syringe assemblies and methods of aspirating and expelling a liquid from a syringe assembly.

A first aspect of the present invention pertains to a retractable syringe assembly having a retraction feature that is activated by the user to retract a needle hub assembly, which includes a needle cannula, into the syringe assembly.

In the embodiment shown in FIGS. 1-5, the retractable syringe assembly includes a dual syringe barrel 101 that includes fluid barrel 110 and a retraction barrel 120. The retractable syringe also includes a needle hub assembly 140, a plunger rod 160, stopper 170 and a trigger element 190. The fluid barrel shown in FIG. 4, includes a distal end 111, a open proximal end 119, a sidewall 112 extending from the distal end 111 and the proximal end 119 including an inside surface 114 defining a chamber 115. The inside surface 114 defines a cross-sectional width and may include a reuse prevention feature, that will be discussed in greater detail below. The distal end 111 includes a distal wall 117 that encloses the distal end 111. In the embodiment shown, the sidewall 112 includes a first aperture 123 for permitting fluid communication between the fluid barrel and the retraction barrel. As will be discussed in greater detail below, the first aperture 123 also permits fluid communication between a needle cannula disposed within the retraction barrel 120 and the retraction barrel 120 and the fluid barrel 110.

The fluid barrels shown in FIGS. 1-7 may include a reuse prevention feature. Specifically, the fluid barrel 110 may include a retaining element 109 that extends around the entire circumference of the inside surface 114 of the fluid barrel 110 at a location adjacent to the proximal end 119 of the fluid barrel. The cross-sectional width of the inside surface 114 at the retaining element is less than the first cross-sectional width or the cross-sectional width of the inside surface 114 at the remaining locations along the length of the fluid barrel. In one or more embodiments, optional tabs or detents can be used to create a region of the fluid barrel 110 having a cross-sectional width that is less than the first cross-sectional width of the fluid barrel 110. The retaining element may also be shaped to facilitate activation of the reuse prevention feature. For example, the fluid barrel 110 may also include a diameter transition region disposed proximally adjacent to the retaining element at the proximal end 119 of the fluid barrel 110. The cross-sectional width of the inside surface 114 of the fluid barrel at the diameter transition region increases from the distal end 111 to the proximal end 119 of the fluid barrel 110. As will be described in greater detail below, in embodiments of the retractable syringe assembly that utilize a reuse prevention feature, the reuse prevention feature of the fluid barrel 110 cooperates with corresponding reuse prevention features on plunger rod 160 to lock the plunger rod 160 within the fluid barrel 110 and/or to disable the plunger rod 160 from further use.

An alternative embodiment is shown in FIGS. 6-7, wherein the retractable syringe assembly may include a single barrel 200. In such embodiments, a portion of the barrel is divided by a dividing wall 201 into a fluid barrel 210 and the remaining portion of the barrel houses the retraction feature and the needle hub assembly and is referred to as the retraction barrel 220. The dividing wall 201 may include an aperture 232 for permitting fluid communication between the fluid barrel 210 and the retraction barrel 220. The single barrel 200 of FIGS. 6-7 provides an ergonomic design which improves grip by providing a large diameter for small syringe sizes.

In the embodiments shown in FIGS. 1-5, the retraction barrel 120 is disposed adjacent to the sidewall 112 of the fluid barrel 110 in the embodiment shown in FIG. 4. The retraction barrel 120 is configured to house a needle hub assembly 140 therein and the retraction feature. The retraction barrel 120 includes an open distal end 121 and an open proximal end 129. A wall 122 having an interior surface 124 defining the needle chamber 125 extends from the distal end 121 to an open proximal end 129. The wall 122 of the retraction chamber is adjacent to the sidewall 112 of the fluid barrel 110. In one or more embodiments, the wall 122 may extend around the portions of the retraction barrel 120 that are not in direct contact with fluid barrel 110 and the sidewall 112 may form the barrier between the retraction barrel 120 and the fluid barrel 110. In other words, the outside surface of the sidewall 112 may form the interior surface 114 of the retraction barrel 120 along the portion of the retraction barrel 120 that is in direct contact with the fluid barrel 110.

The size of the needle chamber 125 may be modified to accommodate the needle hub assembly 140 and/or the retraction feature. According to one or more embodiments, the interior surface 124 of the retraction barrel 120 has a cross-sectional width that is smaller than the first cross-sectional width of the fluid barrel 110. In specific embodiments, the cross-sectional width of the interior surface 124 of the retraction barrel is less than about 90%, 80%, 70%, 60%, 50%, 40%, 30%, or 20% of the cross-sectional width of the inside surface 114 of the fluid barrel. Such designs in which the cross-sectional width of the interior surface 124 of the retraction barrel is less than the cross-sectional width of the inside surface 114 of the fluid barrel, provides ergonomic and functional advantages. For example, the overall appearance and handling of the dual barrel syringe is more appealing to the user. In certain embodiments, the retraction barrel can be nested within the fluid barrel. For example, both the retraction barrel and the fluid barrel may both be bounded or circumscribed by a common wall, and the retraction barrel may be partially or fully disposed within the fluid barrel, or alternatively, a dividing wall may separate a single barrel into two separate barrels, a fluid barrel and a retraction barrel.

The open distal end 121 of the retraction barrel 120 in the embodiment may be fully open or partially enclosed by, for example, a barrier wall (not shown) that partially encloses the open distal end 121. The open distal end 121 may be free of a barrier wall and may be fully open. In such embodiments, the needle hub assembly forms a closure around the open distal end 121 such that there is fluid communication between the needle cannula and the aperture 123 that permits fluid communication between the fluid barrel 110 and the retraction barrel 120. In one embodiment, as shown in FIG. 5, the wall 122 may include a second aperture (not shown) that permits fluid communication with the fluid chamber 115 and the needle chamber 125. The second aperture of the wall may also allow fluid communication between the fluid chamber 115, needle chamber 125 and the needle cannula. The fluid communication between the fluid barrel 110 and retraction barrel 120 may be provided by a first conduit (not shown) that extends from a first aperture (not shown) of the fluid barrel 110 and the second aperture (not shown) of the retraction barrel.

According to one or more embodiments, the retraction barrel has a cross-sectional dimension that is smaller than the cross-sectional dimension of the fluid barrel. In specific embodiments, the cross sectional dimension of the retraction barrel is less than about 90%, 80%, 70%, 60%, 50%, 40%, 30%, or 20% of the cross-sectional dimension of the fluid barrel. Such designs in which the cross-sectional dimension of the retraction barrel is less than the cross-sectional dimension of the fluid barrel, provides ergonomic and functional advantages. For example, the overall appearance and handling of the dual barrel syringe is more pleasing to the user.

The needle hub assembly may include a second conduit (not shown) that extends from an open end of the needle cannula to second aperture (not shown) of the retraction barrel. The second conduit may include an opening (not shown) that must be aligned with the second aperture to permit fluid communication between the needle cannula and the fluid barrel.

The needle hub assembly 140 is disposed within the retraction barrel 120 and includes a needle hub 142 and a needle cannula 150 attached to the needle hub 142. The needle hub 142 includes a distal end 141 and a proximal end 149. The needle cannula 150 includes a free and open distal end 151 end and an open proximal end 159 that is attached to the distal end 141 of the needle hub. The needle hub 142, shown in FIGS. 4 and 8, includes a needle hub body 143 and a needle cannula support 146 disposed distally within the needle hub body 143. The needle cannula support 146 includes a recessed portion (not shown) for partially housing one end of the needle cannula. The recessed portion may include a portion of the second conduit (not shown) that extends through the needle hub 142 to the second aperture (not shown) of the retraction barrel to permit fluid communication between the needle cannula 150 and the fluid barrel 110.

Figure 13:
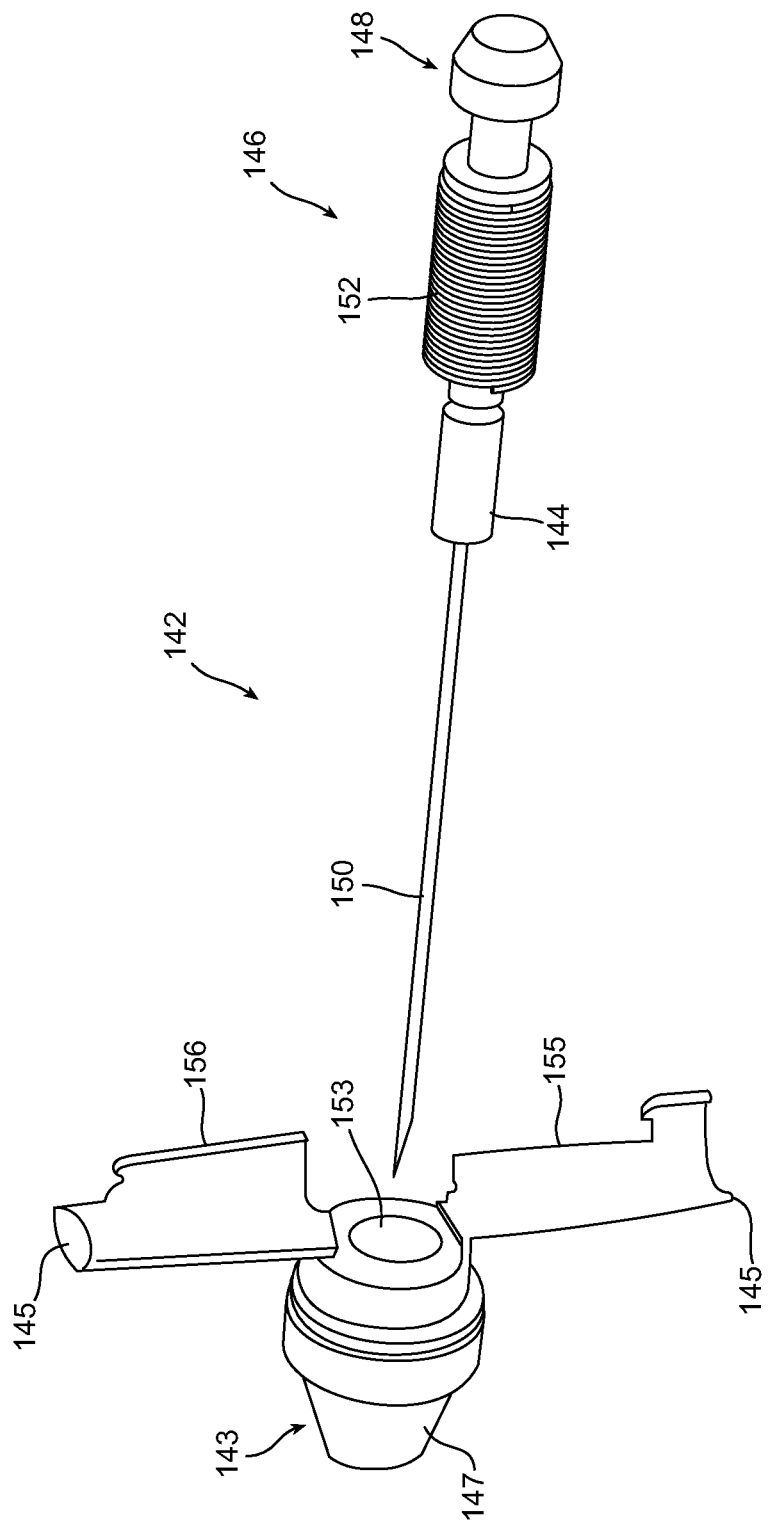
FIG. 13 illustrates a perspective view of the assembly of a needle hub assembly according to according to one or more embodiments.
Figure 14:
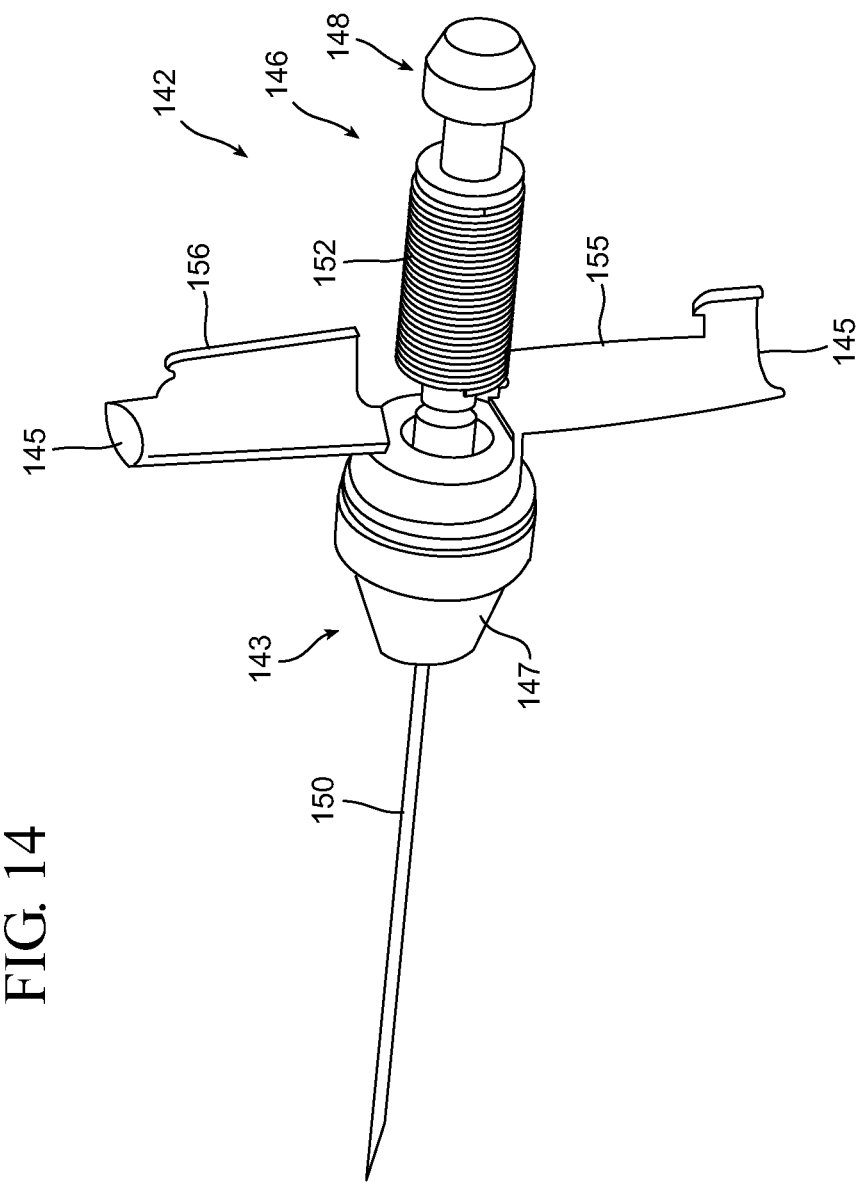
FIG. 14 illustrates the needle hub assembly of FIG. 13 as the needle cannula and needle cannula support is being inserted into the needle hub.
Figure 15:
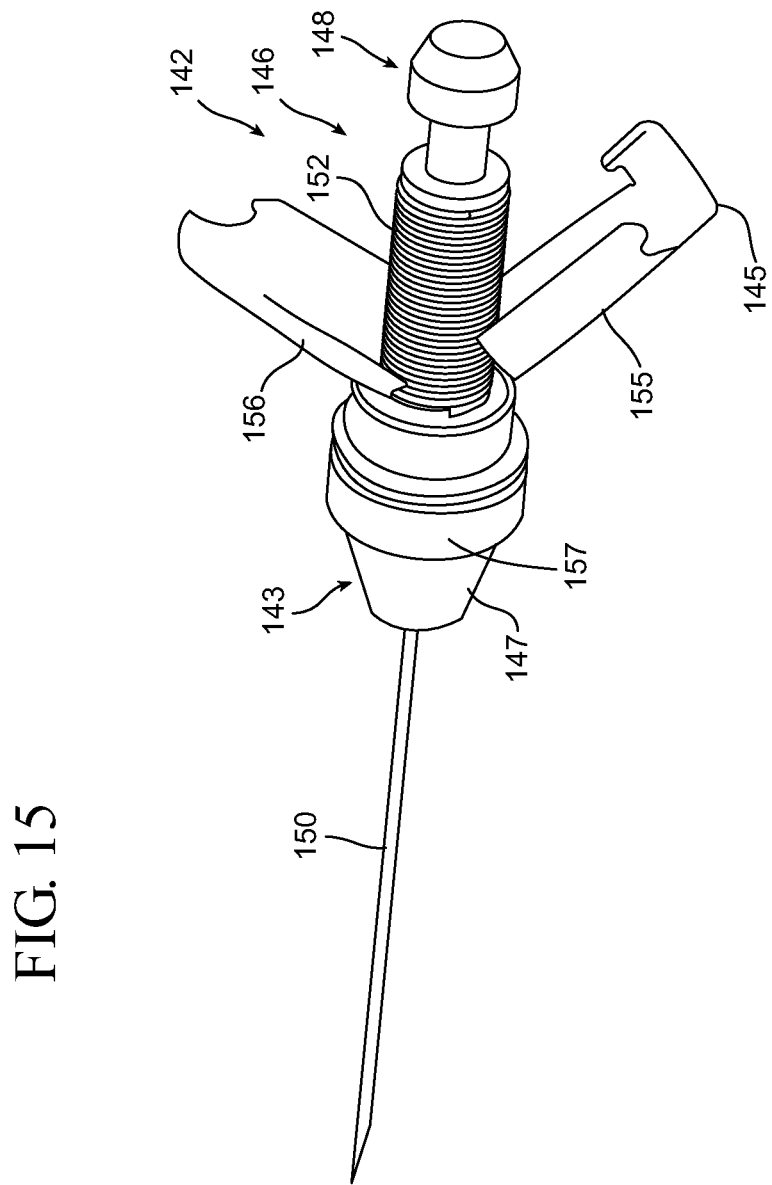
FIG. 15 illustrates the needle hub assembly of claim 14 as the needle hub is being formed around the needle cannula and the needle cannula support.
Figure 16:
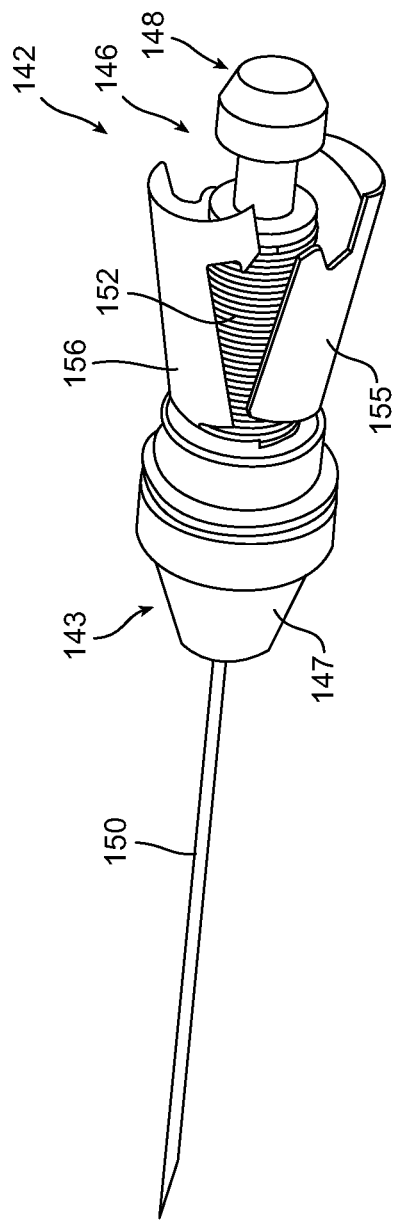
FIG. 16 illustrates the needle hub assembly of claim 15 as needle hub is more fully being formed around the needle cannula and the needle cannula support.
Figure 17:
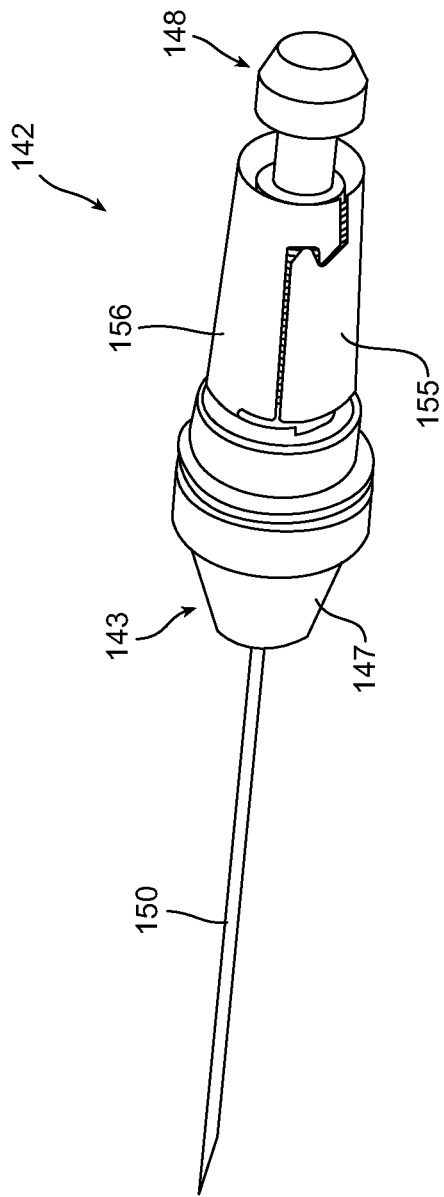
FIG. 17 the assembled needle hub assembly of claim 16.

The needle cannula 150 of the needle hub assembly 140 is biased to move in the proximal direction. In the embodiment shown, the needle hub assembly 140 is biased to move in the proximal direction, thereby biasing the attached needle cannula 150. In the embodiment shown, the needle hub assembly 140 is biased to move in the proximal direction by a biasing element 152 disposed between the needle hub body 143 and the needle cannula support 148. As shown more fully in FIGS. 13-17, the biasing element 152 is shown as surrounding the needle cannula support 146. To assemble the needle hub assembly 140 with the biasing element 152, the biasing element 152 is initially placed over the needle cannula support 146 and compressed, as shown in FIG. 13. The needle hub body 143 includes a distal end 144, a proximal end 145, distal portion 147 disposed adjacent to the distal end and proximal portion 148 disposed adjacent to the proximal end. The distal portion 147 may include a conical fitting with an opening (not shown) therethrough for receiving the needle cannula 150. The proximal end 148 includes two hinged enclosing walls 155, 156. The enclosing walls 155, 156 surround the needle cannula support and the biasing element 152 as they are assembled with the needle hub body 143. Specifically, the needle cannula 150 is inserted into the opening of the distal portion 147 as shown in FIG. 14. The cross-sectional width of the opening increases from the proximal end of the distal portion 147 to the distal end of the distal portion 147 so that the needle cannula 150 extends through the opening, while the needle cannula support 146 remains within the distal portion 147. The two hinged enclosing walls 155, 156 of FIGS. 15-16 are moved inwardly until they surround the needle cannula support 146 and the biasing element 152, as shown in FIG. 17.

In the embodiment shown, the biasing element 152 engages the needle cannula support 146. The biasing element 152 may include a spring, which may be a compression spring that applies a constant force on the needle hub body 143 in the proximal direction. In alternative embodiments, the biasing element 152 may be provided in another form, for example, a lever arm (not shown) may be disposed between the needle hub and the barrier wall. The needle hub body 143 includes a frangible element 153 that supports biasing element 152, the needle cannula support 146 and the needle cannula 150 from moving in the proximal direction. As will be explained in greater detail below, breaking the frangible element 153 will allow the biased needle hub 142 and the needle cannula 150 attached thereto to retract into the retraction barrel 120.

In one or more variants, the entire needle hub assembly 140 may be biased. For example, the needle hub body 143, needle cannula support 146 and the needle cannula 150 may be provided as an integral unit that is biased and the retraction barrel may include a support element (not shown) that is frangible and applies a force on the needle hub assembly 140 in the distal direction. The biasing element 152 may be located between the needle hub assembly 140 and the distal end 121 of the retraction barrel 120. The force applied by the support element to the needle hub assembly 140 in the distal direction counteracts the force applied to the needle hub assembly 140 by the biasing element 152 in the proximal direction. Once the support element is broken, the needle hub assembly 140 may be retracted into the retraction barrel 120.

The frangible element 153 is shown in FIGS. 8-12 as a partially extending shelf wall 154 that is disposed along portions of the inside surface of the needle hub body 143. The shelf wall 154 extends radially inwardly to form a supporting barrier that is positioned adjacent to the biasing element 152 that surrounds the needle cannula support, which prevents movement or expansion of the biasing element 152. Once the frangible element 153 is broken, for example, by the movement of the trigger element 190 in the distal direction, the engagement between the biasing element 152 and the needle cannula support 146 cause the biasing element 152 to move the needle cannula support 146 and the needle cannula 150 attached thereto into the trigger element 190 and/or the retraction barrel 120. Specifically, the expansion of the biasing element 152 drives the needle cannula support 146 and the needle cannula 150 into the trigger element 190 and/or the retraction barrel 120.

The needle hub assembly is sized moveable within the needle chamber. The size and shape of the needle hub assembly may be modified to permit movement in needle chambers having different sizes. In the assembled state, prior to use, the needle hub assembly is positioned at the open distal end of the retraction barrel.

A plunger rod 160 is disposed within the fluid barrel 110 and includes a stopper 170 attached thereto for forming a fluid-tight seal with the inside surface 114 of the fluid barrel 110. The plunger rod 160 may include a reuse prevention feature that locks the plunger rod 160 within the fluid barrel 110 or otherwise disables the plunger rod 160. The plunger rod may include a reuse prevention feature that cooperates with a reuse prevention feature disposed on the fluid barrel 110. In one or more embodiments, the plunger rod may include a protrusion 113 that has a cross-sectional width that is greater than the cross-sectional width of the inside surface 114 of the fluid barrel 110 at the retaining element 109. As discussed above, the retaining element forms a smaller cross-sectional width than at other locations along the length of the fluid barrel 110. Accordingly, when the protrusion of the plunger rod advances distally past the retaining element of the fluid barrel 110, the smaller cross-sectional width of the retaining element prevents movement of the protrusion in the proximal direction. Accordingly, the plunger rod 160 is locked within the fluid barrel 110 by the retaining element. In one or more embodiments, the stopper 170 and/or the plunger rod 160 may have a structure to permit relative movement of the plunger rod 160 with respect to the stopper 170. For example, the stopper 170 may have an interior recess that allows the distal end of the plunger rod 160 to move in the distal and proximal directions within the interior recess, thus elongating and shortening the length of the plunger rod and the stopper. Exemplary plunger rods and stoppers which permit relative movement of the plunger rod with respect to the stopper are disclosed in U.S. patent application Ser. Nos. 12/137,732 (published as United States Patent Application Publication Number 20090048560) and 12/262,836 (published as United States Patent Application Publication Number 20090131869), each of these applications being incorporated herein by reference in its entirety.

The stopper 170 may also include reuse prevention features that also cooperates with reuse prevention features disposed on the fluid barrel 110. For example, the stopper 160 may include a sealing portion (not shown) that has a cross-sectional width that is greater than the cross-sectional width of the inside surface 114 of the fluid barrel 110 at the retaining element. In such embodiments, removal of the stopper 170 is prevented because the smaller cross-sectional width of the retaining ring of the fluid barrel 110 prevents the stopper 170 from being removed. The plunger rod 160 and the stopper 170 may be joined by a frangible connection 172 that may cause the plunger rod 160 to become disconnected from the stopper 170, while the stopper 170 remains locked within the fluid barrel 110 by the retaining element. Exemplary stoppers which include a reuse prevention feature and plunger rods and stoppers joined by a frangible connection are disclosed in U.S. application Ser. Nos. 12/137,732 and 12/262,836, referred to above.

The retractable syringe assembly 101 also includes a trigger element 190 that includes a distal end 191 and a proximal end 199. The trigger element 190 is moveable independently of the plunger rod 160 and extends into the needle chamber 125 of the retraction barrel 120. In the embodiment shown in FIG. 4, the trigger element 190 includes a trigger pad 194 on which the user applies a force in the distal direction to activate the retraction mechanism of the syringe assembly.

The trigger element 190 is sized, shaped and positioned to provide a trigger force on the frangible element 153 of the needle hub body 143 to release the biasing element 152 so the needle cannula 150 retracts and is housed into the retraction barrel. The trigger element 190 includes a trigger element body 192 that extends from the distal end 191 to the proximal end 199. The trigger element body 192 is shaped to have a cylindrical shape and is elongate. In the embodiment shown, the trigger element 190 has an open distal end 191 and the trigger element body 192 has a hollow interior 193 to house the needle hub 142 and the needle cannula 150. The proximal end 199 of the trigger element is closed and may be tapered to retain the needle hub 142 within the hollow interior 193 after the needle hub 142 and the needle cannula 150 is retracted into retraction barrel. The needle cannula support 146 may also include structure to retain the retracted needle cannula support 146 and the needle cannula 150 within the trigger element 190.

The open distal end 191 of the trigger element may have a beveled edge that breaks the frangible element 153 more efficiently by concentrating the force applied to the frangible element 153. The breaking of the frangible element 153 releases the force applied to the biasing element 152 and the needle cannula support 146 in the distal direction. After the release of this distally direction force, the force applied on the needle cannula support 146 by the biasing element 152 in the proximal direction remains due to the compression of the biasing element 152. The expansion of the biasing element 152 or the presence of the proximally directed force on the needle cannula support 146 by the biasing element 152 causes the needle hub 142 to retract or move into the retraction barrel 120 or specifically, the hollow interior 193 of the trigger element.

Figure 8:
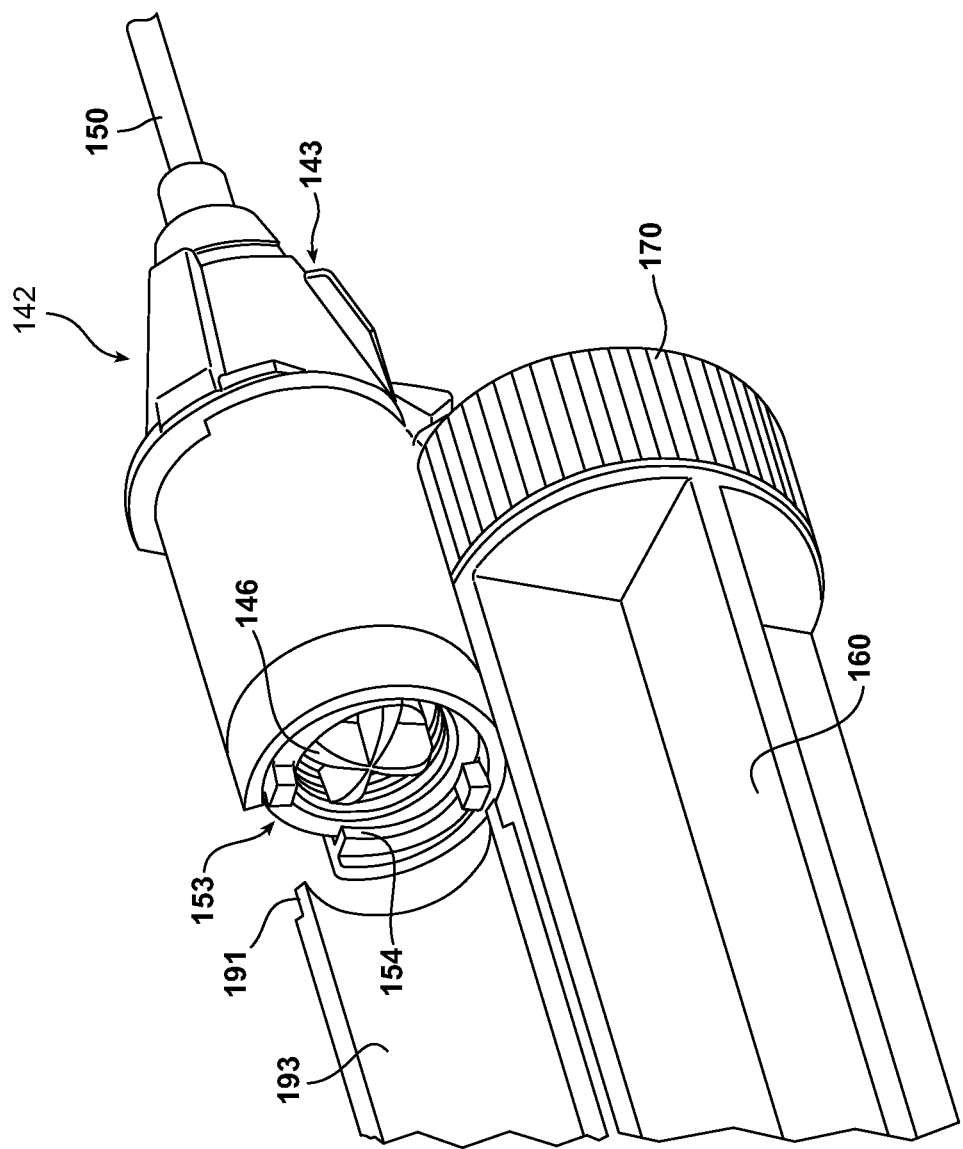
FIG. 8 illustrates a partial perspective view of the plunger rod, needle hub assembly and trigger element of FIGS. 4 and 6 prior to retraction of the needle hub assembly.
Figure 9:
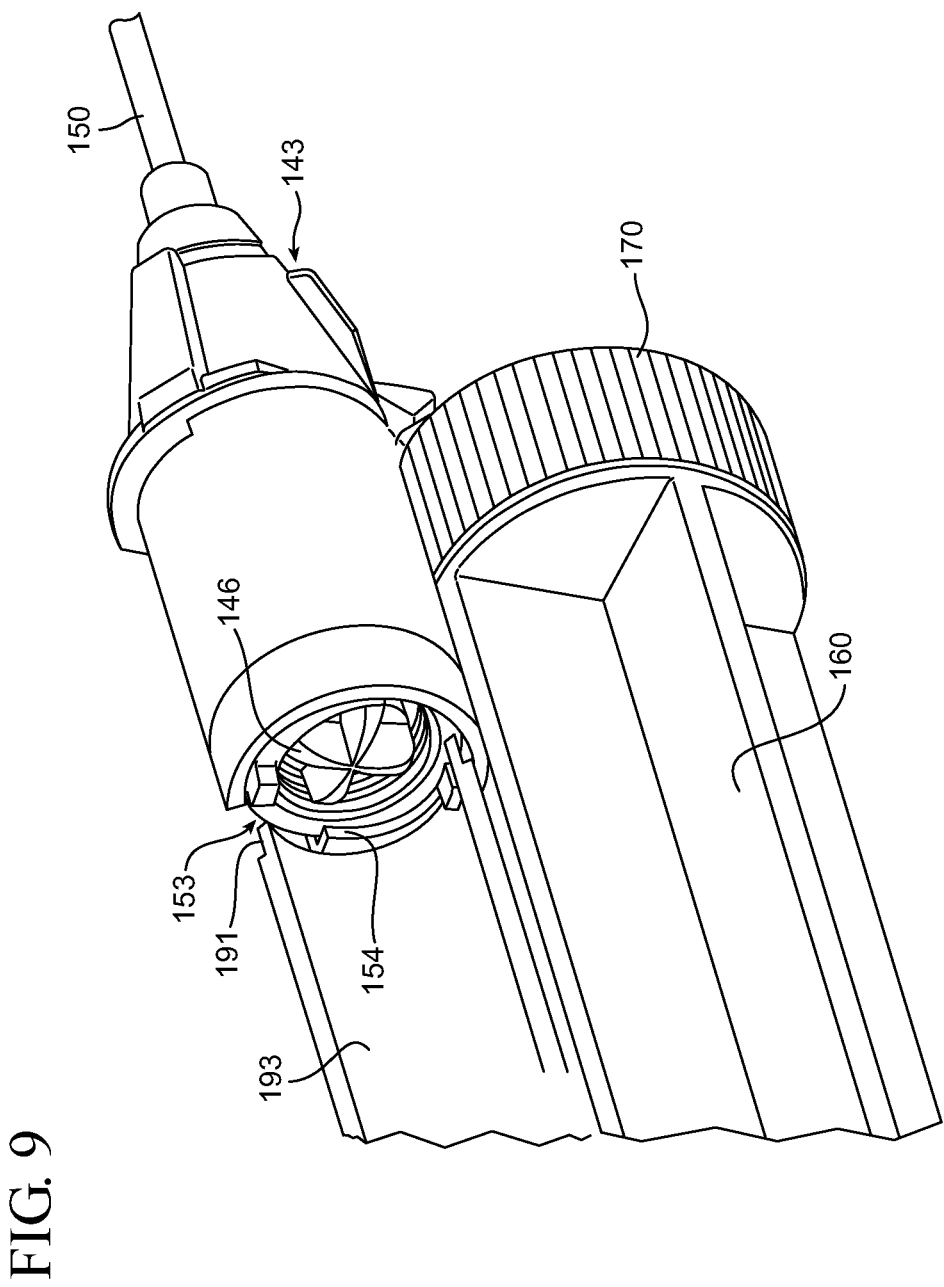
FIG. 9 illustrates a partial perspective view of the plunger rod, needle hub assembly and the trigger element shown in FIG. 8 after application of a force on the trigger element in the distal direction.
Figure 10:
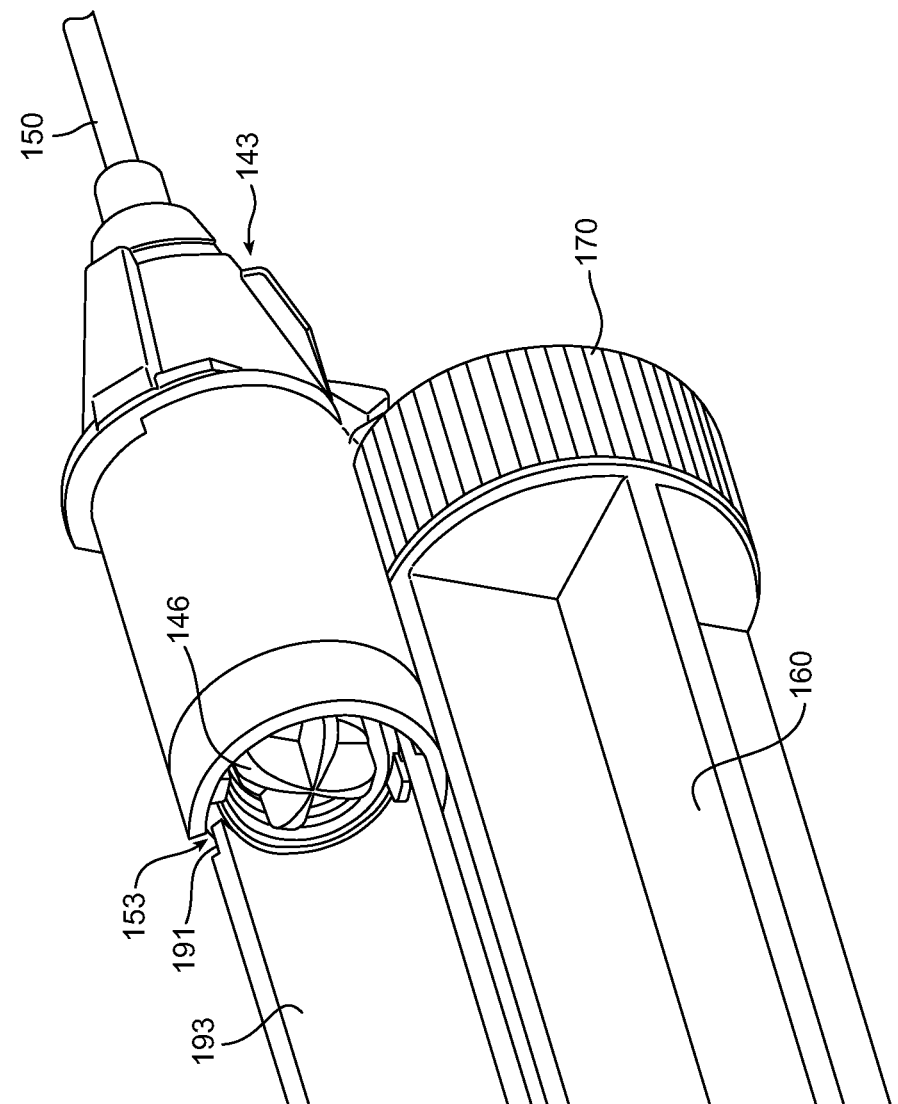
FIG. 10 illustrates a partial perspective view of the plunger rod, needle hub assembly and the trigger element shown in FIG. 9, after the trigger element breaks the frangible element.
Figure 11:
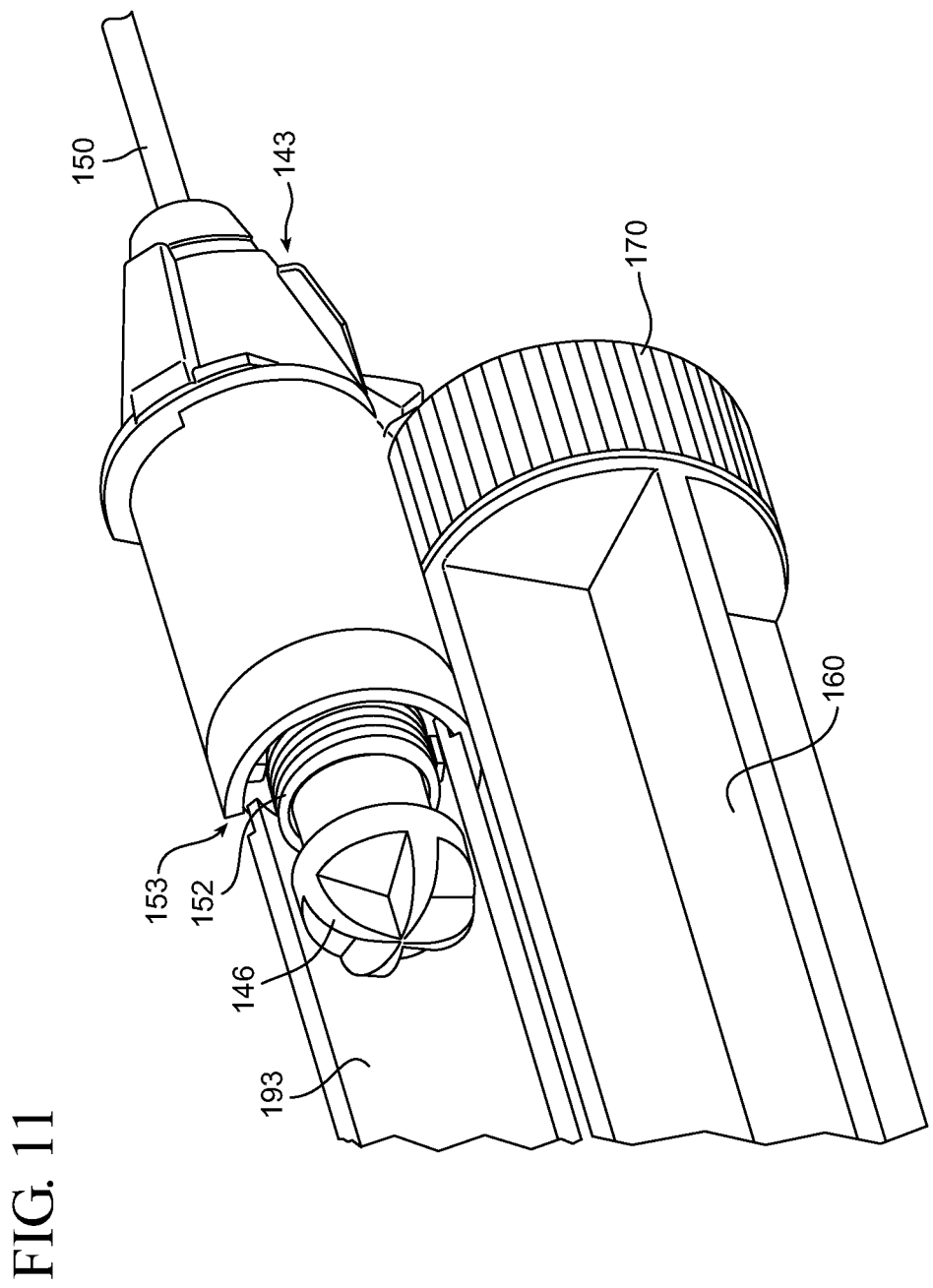
FIG. 11 illustrates a partial perspective view of the plunger rod, needle hub assembly and the trigger element shown in FIG. 10 after a portion of the needle hub assembly begins to retract into the retraction barrel.
Figure 12:
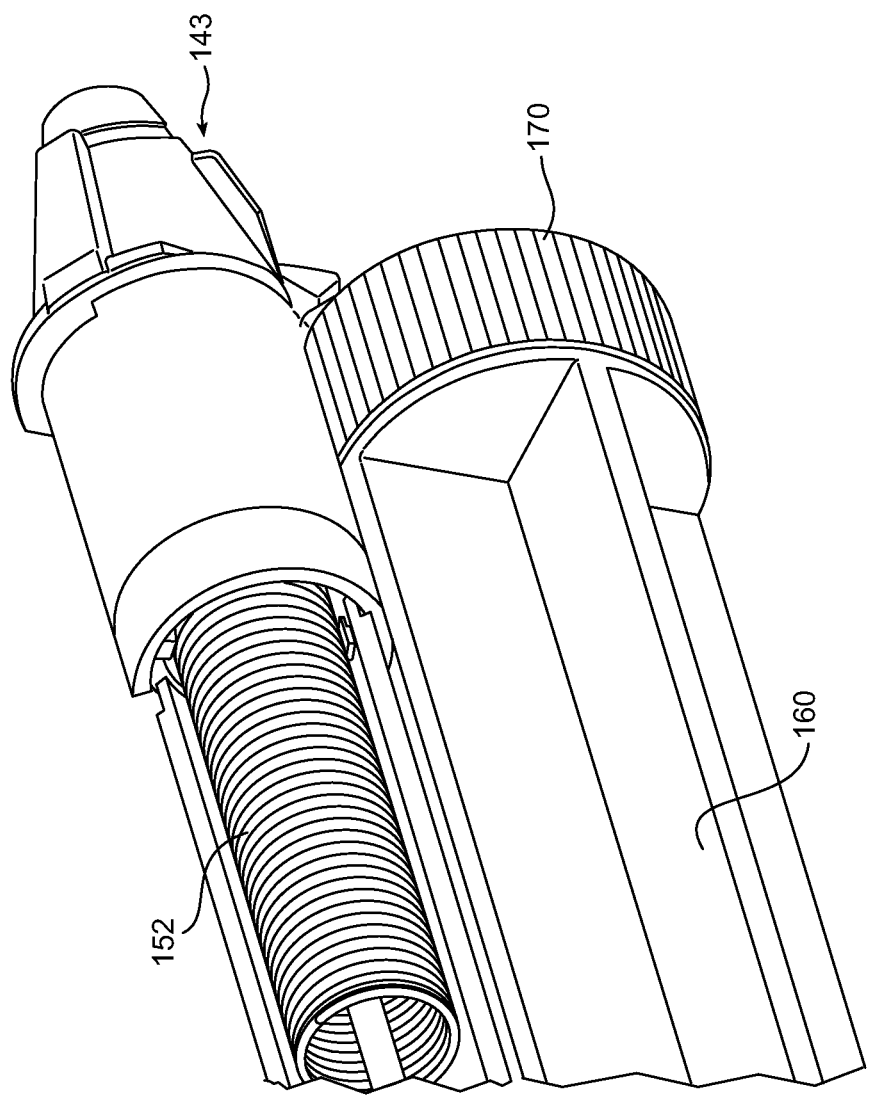
FIG. 12 illustrates a partial perspective view of the plunger rod, needle hub assembly and the trigger element shown in FIG. 11 after the portion of the needle hub assembly is more fully retracted into the retraction barrel.

In use, as shown in FIGS. 8-10, the user is free to aspirate fluid or liquid into the fluid barrel 110 and expel the fluid without inadvertently activating the retraction mechanism and retracting the needle cannula. After the user aspirated and expelled the liquid as desired, the user may activate the retraction mechanism by applying a force on the trigger element 190 in the distal direction. The separate retraction barrel 120 and the needle chamber 125 allows the use of a reliable or constant activation force to activate the retraction mechanism. Specifically, the activation force is no longer dependent on the viscosity of the liquid filled within the fluid chamber 115. In addition, the activation force no longer has to compensate for the risk of accidental activation during normal operation of the syringe assembly, and, therefore, the activation force may be set at a low level. Moreover, because the retraction feature no longer has to cut through a stopper, as required by some retractable syringe assemblies, the activation force can be optimized to solely activate the retraction feature, instead of also being optimized to penetrate stoppers.

In addition, the separation of the retraction mechanism from the fluid barrel 110 also reduces the risk of accidental activation because it is no longer coupled with the aspiration and injection of the fluid using the plunger rod. Accordingly, there is no risk of premature activation of the retraction mechanism by applying high force during high speed injections. In use, after the finger or thumb is used to apply a force on the plunger rod 160 to expel the contents of the fluid barrel 110, the user simply shifts the finger or thumb to the trigger pad 194 disposed adjacent to the thumb press 164 at the proximal end of the retraction barrel 120. The user does not need to modify their grip or utilize two hands to activate the retraction mechanism, as is required in known embodiments of retractable syringe assemblies.

The separation of the retraction barrel, needle hub assemblies and the retraction feature of the syringe assemblies disclosed herein also allows the use of exchangeable needles for all dimensions of the retractable syringe. The asymmetrical orientation of the needle hub assembly, with respect to the entire syringe assembly, facilitates low angle injections (i.e. subcutaneous injections). Further, the asymmetrical orientation also allows the user to detent needle cannula orientation by simply gripping the syringe assembly.

In one or more embodiments, the needle hub assembly may be attached to the retraction barrel to provide a leak proof pathway for the liquid. In one or more embodiments, this is accomplished by utilizing a needle hub assembly that includes a sealing member, which is activated by the pressing and turning required to assemble the needle hub assembly. The pressing and turning motions are achieved by incorporating slightly wedged surfaces on the needle hub assembly which attach to corresponding structures on the retraction barrel. The needle hub assembly may also be designed to be turned and attached in one direction. This allows the needle hub assembly to be locked in a defined position, while the torque applied is turned into sealing pressure.

Figure 18:
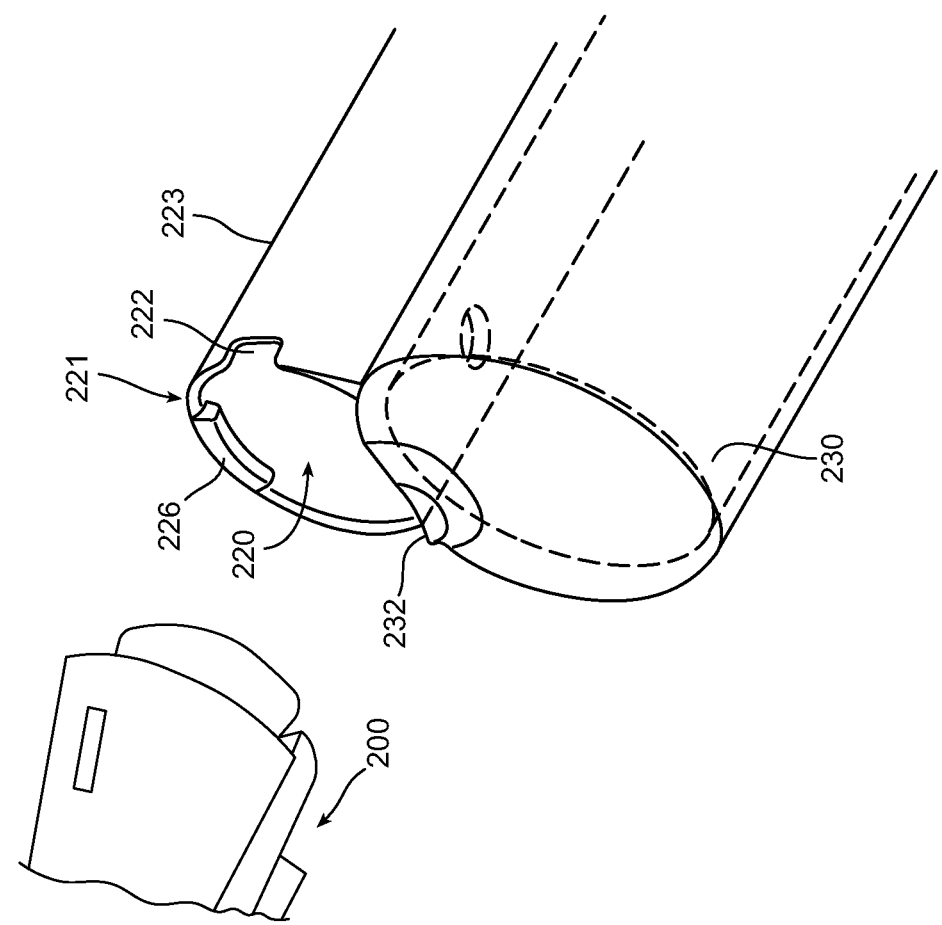
FIG. 18 illustrates a perspective view of a needle hub assembly being assembled to a retraction barrel according to one or more embodiments.

In the embodiment shown in FIGS. 18-23, the needle hub assembly 200 may be shaped and sized to cooperate with the retracting barrel 220 and a needle shield 240 to provide sealing pressure to the retraction barrel. In the embodiment shown, the retraction barrel 220 includes a wall 223 that extends from an open distal end 221. The wall includes a securing element 222 disposed at the distal end 221 for securing the needle hub assembly 200 to the retraction barrel. The securing element 222 is formed integrally with the sidewall of the barrel, as shown in FIG. 18. In the embodiment shown, the securing element 222 includes at least one indentation or opening 224 for receiving a corresponding finger element or other protrusion on the needle hub assembly. In the embodiment shown, the opening 224 extends in a distal direction from the open distal end 221. The securing element also includes at least one inwardly extending protuberance 226 that is disposed adjacent to the opening 224. The protuberance 226 extends inwardly into the open distal end 221 of the retraction barrel.

The retraction barrel 220 is attached to a fluid barrel 230 with a fluid chamber (not shown) that includes an aperture 232 for permitting fluid communication between the needle hub assembly 200 and the fluid chamber. The aperture 232 is disposed on the opposite side of the open distal end 221 of the retraction barrel from the protuberance 226. The securing element 222 of the retraction barrel may include alternative structure which cooperates with the needle hub assembly 200 to secure the needle hub assembly 200 to the retraction barrel.

Figure 19:
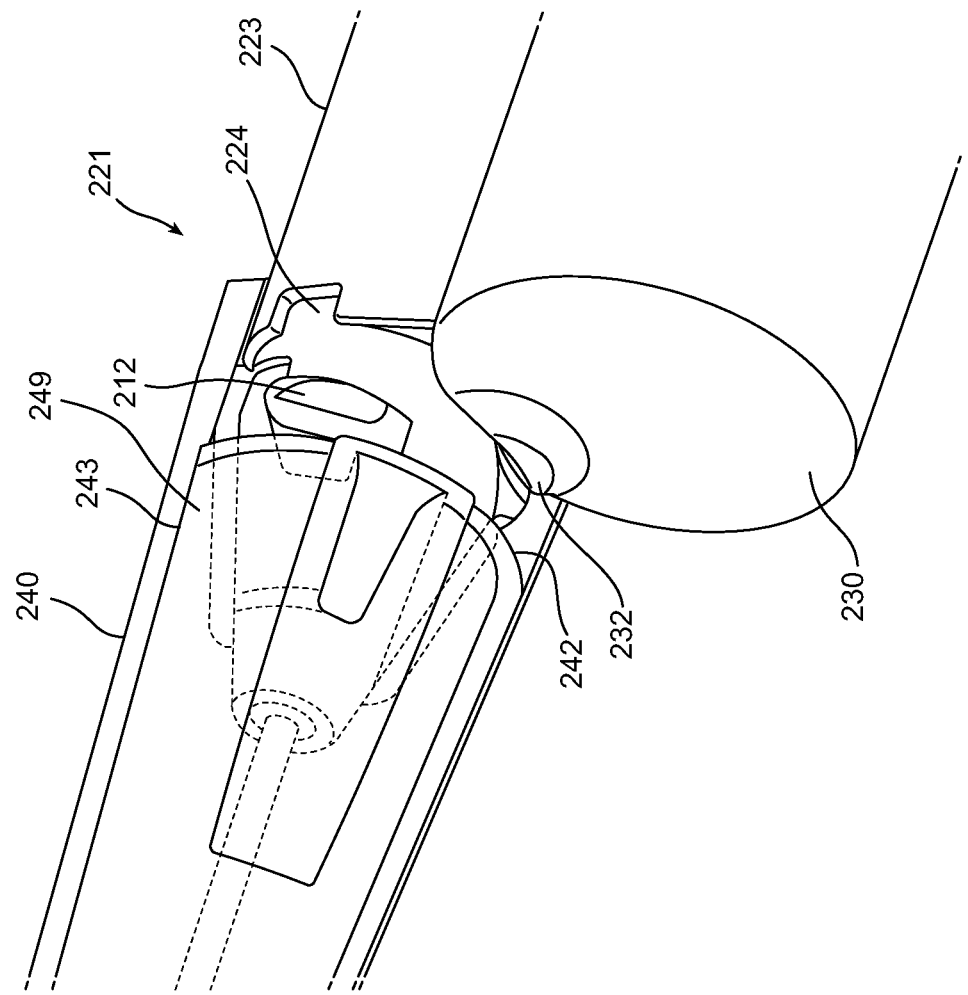
FIG. 19 illustrates the needle hub assembly shown in FIG. 18 attached to a needle shield as it is placed on the retraction barrel also shown in FIG. 18.
Figure 23:
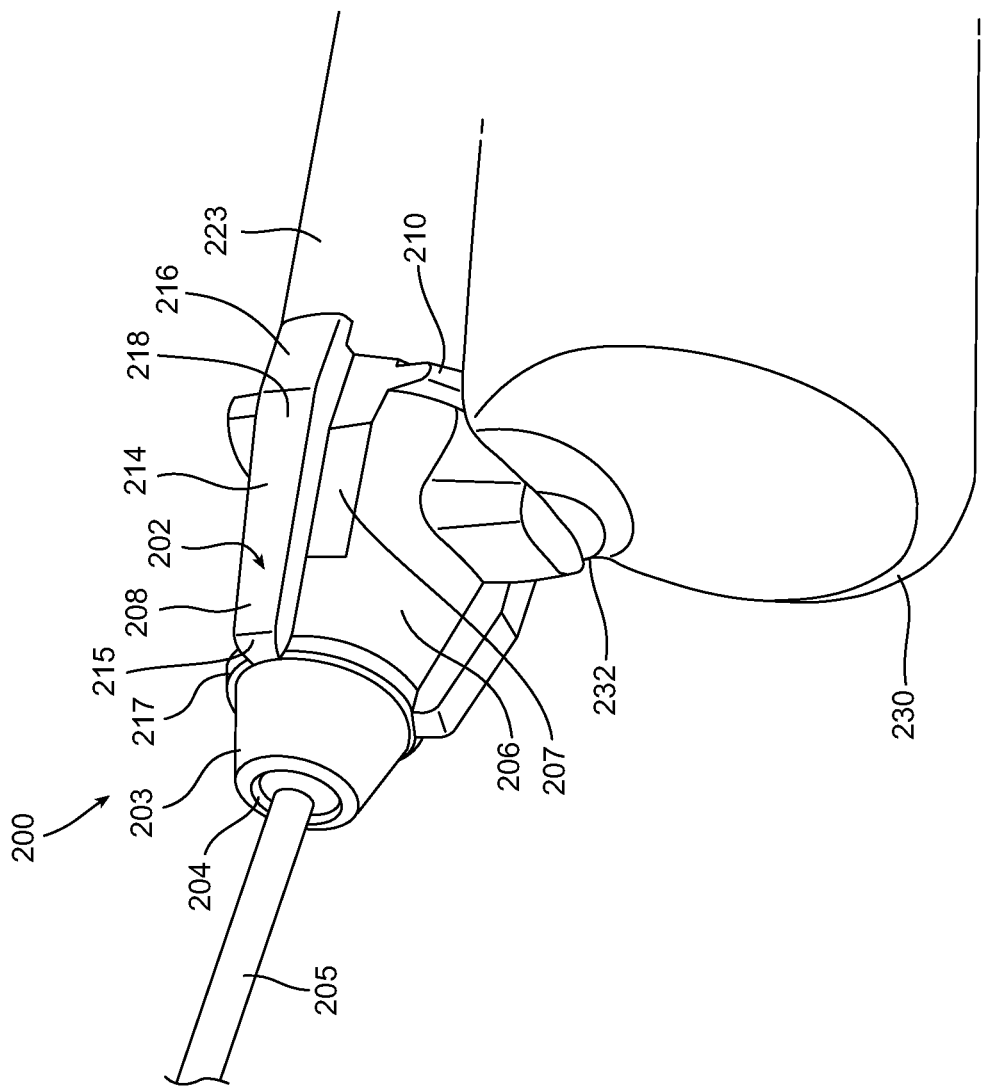
FIG. 23 illustrates the needle hub assembly and needle shield shown in FIG. 22 after removal of the needle shield.
Figure 24:
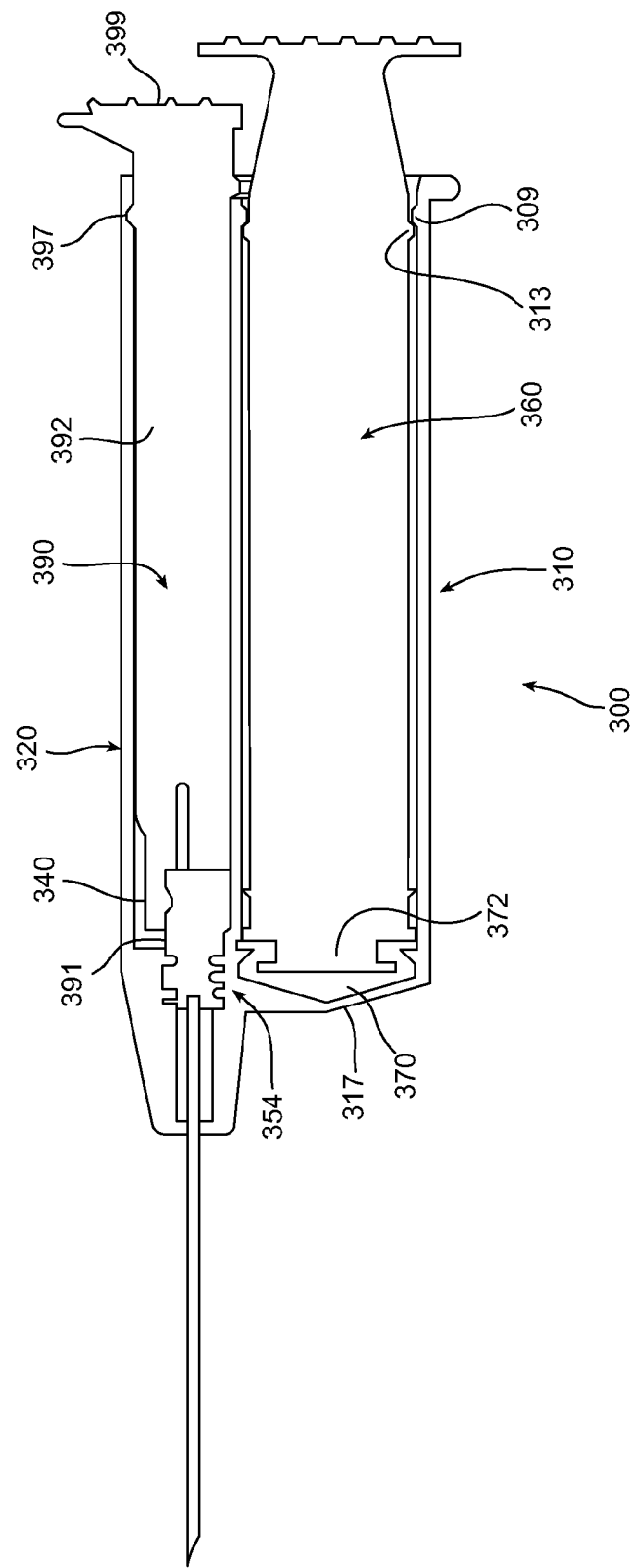
FIG. 24 illustrates cross-sectional side view of a retractable syringe assembly according to one or more embodiments.

As shown in FIG. 19, the needle hub assembly 200 is assembled with a needle shield 240 prior to attachment to the retraction barrel. As shown in FIG. 23, the needle hub assembly includes a needle hub body 202 having a distal end 203 and a proximal end (not shown). The distal end 203 includes an opening 204. A needle cannula 205 is disposed within the needle hub body 202 and extends through the opening 204 of the needle hub body. A biasing element (not shown) may be disposed within the needle hub body 202 as otherwise described herein, for example, with reference to FIGS. 8-17. The needle hub body 202 includes an outside surface 206 that includes an attachment element 208 that engages the securing element 222 of the retraction barrel 220. The outside surface 206 has a generally rounded conical shape or a curved conical shape. In the embodiment shown, the attachment element 208 of the needle hub assembly includes at least one radially outwardly extending tab 210 disposed on the outside surface 206 of the needle hub body. The tab 210 engages the protuberance 226 by sliding under the protuberance 226 such that the protuberance 226 exerts a force in the proximal direction on the tab 210, when the needle hub assembly 200 is attached to the retraction barrel.

The needle hub body 202 also includes an open conduit 212 for permitting fluid communication between the needle cannula 205 and the aperture 232 of the fluid barrel. In the embodiment shown, the position and location of the attachment element 208 and the securing element 222 permits alignment of the open conduit 212 and the aperture 232. Moreover, proper engagement of the attachment element 208 and the securing element 222 ensures fluid communication between the fluid barrel 230 and the needle cannula 205.

In the embodiment shown, the needle hub body 202 also includes at least one finger element 214 disposed along the outside surface 206. Specifically, the finger element 214 has a distal end 215 that is attached to the outside surface 206 and proximal end 216 that is free and unattached to the outside surface 206 of the needle hub body 202. In the embodiment shown in FIG. 23, the finger element 214 is flexible to extend outwardly from the outside surface of the hub body. Application of a radially outwardly-directed force on the finger elements 214 cause the proximal end 216 to lift off the outside surface 206 of the needle hub body. The finger element 214 in the embodiment shown has an elongate shape that extends a distal ring 217 that is disposed distally adjacent to the midpoint between the distal end 203 and the proximal end (not shown) of the needle hub body 202. The distal ring 217 in the embodiment shown forms an indentation on the outside surface 206 of the needle hub body 202 that extends along the perimeter of the outside surface 206. In one variant, the distal ring may form a rib that extends outwardly from the outside surface 206.

The finger element 214 has a rounded distal end 215 in the embodiment shown, but may include a distal end 215 having a different shape. The finger element 214 forms a raised platform with respect to the outside surface 206 of the needle hub body 202. From the distal end 215 to a bent portion 218, the finger element 214 extends substantially parallel to the conically shaped outside surface 206 of the needle hub body 202. From the bent portion 218 to the proximal end 216, the finger element 214 extends substantially parallel to the retraction barrel 220. The outside surface 206 also includes an indented portion 207 adjacent to the finger element 214. The indented portion 207 does not have a curved conical shape, like the remaining portions of the outside surface 206, but instead, has a surface that is parallel to the retraction barrel or is inwardly curved with respect to the retraction barrel. The finger element 214 and the indented portion 207 are disposed adjacent to the tab 210. In the embodiment shown, the needle hub body 202 includes two tabs 210 located across the needle hub body 202 from one another and the indented portion 207 and the finger element 214 disposed therebetween. The open conduit 212 is disposed on the opposite side of the tab 210 from the finger element 214 and the indented portion 207.

The needle shield 240 is disposed over the needle hub body 202 such that it encloses the needle cannula 205. The needle shield 240 provides protection to the user from the needle cannula 205 and prevents contamination of the needle cannula 205. The needle shield 240 also activates the engagement of the needle hub assembly 200 and the securing element 222 of the retraction barrel. In the embodiment shown, the needle shield 240 has structure that engages the needle hub body 202 and facilitates the rotation thereof, with respect to the retraction barrel 220 such that the needle hub assembly 200 is properly attached to the retraction barrel. In the embodiment shown, the needle shield 240 includes a closed distal end (not shown), an open proximal end 249 and a hollow body 242 defining a cavity 243 for receiving the needle hub body 202 and the needle cannula 205. The hollow body 242 includes an interior surface 242. The interior surface 242 includes the structure that enables the needle shield 240 to engage the needle hub body 202 and facilitate attachment of the needle hub assembly 200 to the retraction barrel.

The interior surface 242 includes a plurality of detents 244 that extend inwardly and engage the at least one finger element 214 of the needle hub body 202. The detents 244 engage the finger element 214 to rotate the needle hub body 202 with respect to the securing element 222 to attach the needle hub assembly 200 to the open distal end of the retraction barrel.

Figure 20:
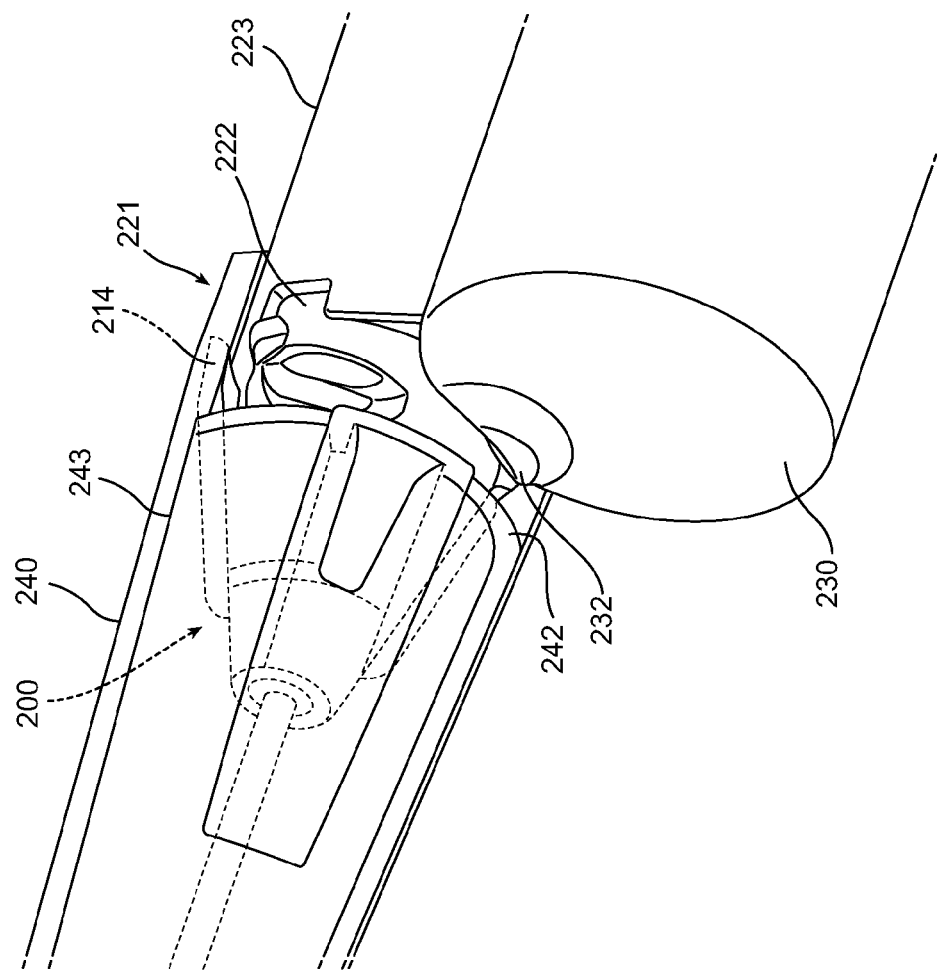
FIG. 20 illustrates the needle hub assembly and needle shield shown in FIG. 19 after the needle shield engages the needle hub assembly.
Figure 21:
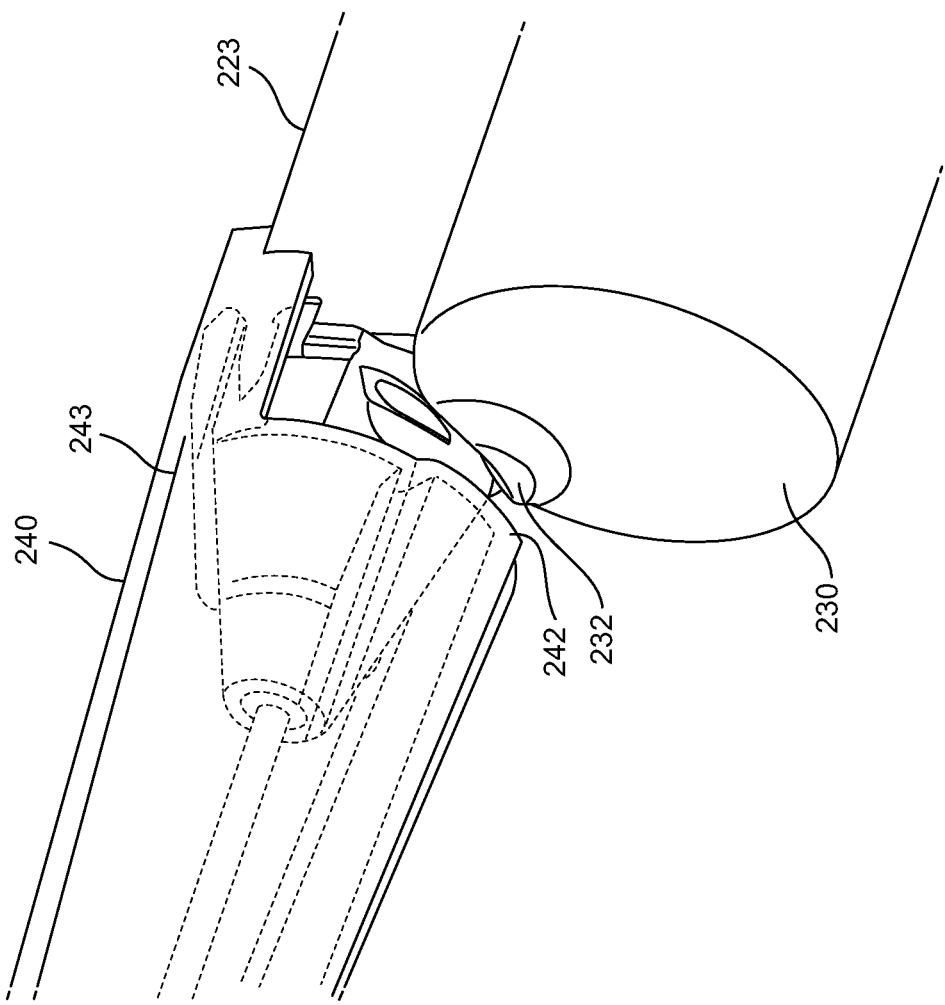
FIG. 21 illustrates the needle hub assembly and needle shield shown in FIG. 20 after rotation with respect to the retraction barrel.
Figure 22:
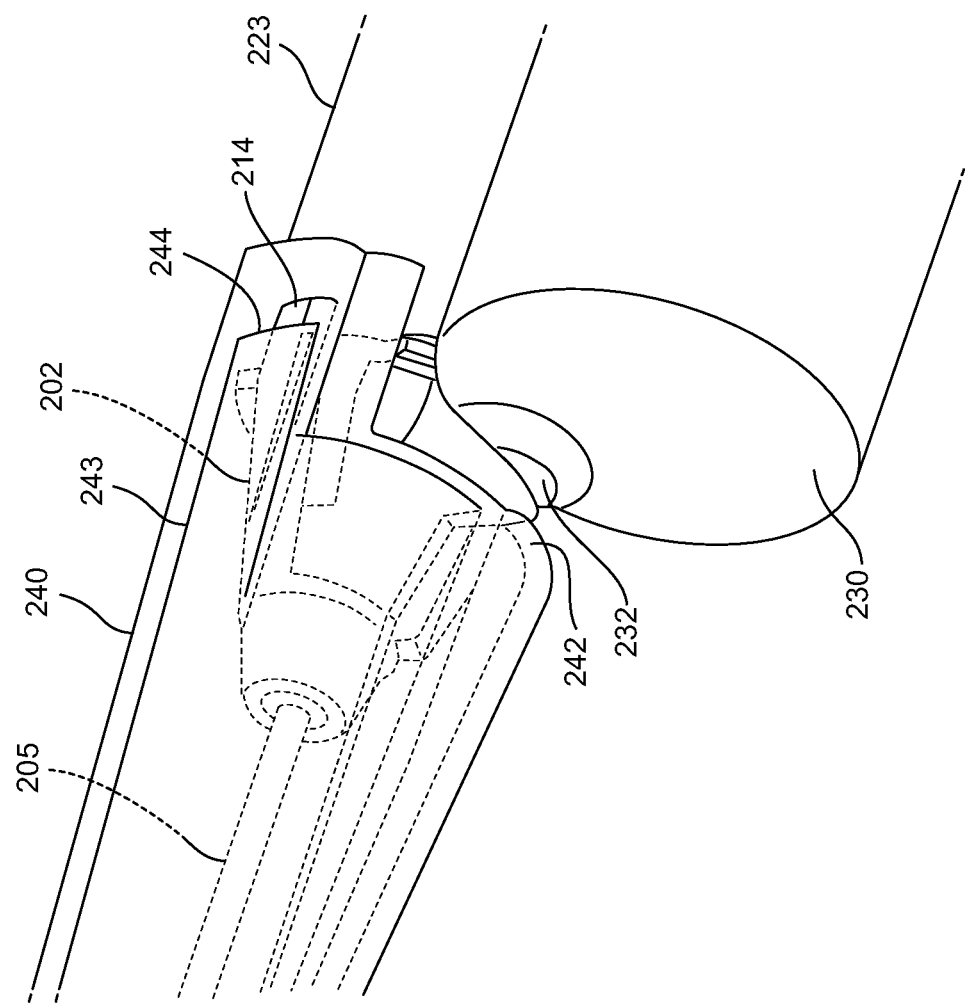
FIG. 22 illustrates the needle hub assembly and needle shield shown in FIG. 21 after alignment of the open conduit of the needle hub assembly and the aperture of the retraction barrel.

As shown in FIG. 20, as the needle hub assembly 200 and the needle shield 240 are placed within the open distal end 221 of the retraction barrel, the finger element 214 flexes as it moves over the wall 223 of the retraction barrel. As the user rotates the needle shield 240 and needle hub assembly 200 attached thereto, the detents 244 engage the finger element 214 and apply a rotational force on the finger element 214 to rotate the needle hub body 202 and needle hub assembly 200 until the tab 210 engages the protuberance 226 of the retraction barrel and the finger element 214 engages the opening 224 of the wall 223 of the retraction barrel. Upon engagement of the tab 210 and protuberance 226 and the finger element 214 and the opening 224, the aperture 232 is aligned with the open conduit 212 of the needle hub assembly. In other words, the engagement of the securing element 222 and the attachment element 208 permits fluid communication between the aperture and the needle cannula. After proper engagement of the securing element 222 and the attachment element 208, the needle shield may be removed from the needle hub body 202.

To remove the needle hub assembly 200 from the retraction barrel, the user places the needle shield 240 over the needle hub body 202 and the needle cannula 205 and applies a rotational force to the needle shield 240, which in turn causes the detents 244 to apply a rotational force on the finger element 214 and cause the needle hub body 202 to rotate in the opposite direction to disengage that tab 210 from the protuberance 226 and the finger element 214 from the opening.

A second aspect of the present invention pertains to a retractable syringe assembly that provides for the separate containment of the retraction mechanism and the needle cannula in a needle chamber. The assembly also includes an activation button, located at the proximal end of the syringe assembly, that extends within the needle chamber and is located adjacent to the plunger rod used to aspirate and expel fluid from a separate fluid chamber disposed adjacent to the needle chamber. On activation of the button, the needle hub is released into the needle chamber.

The embodiments according to the second aspect provide an alternative mechanism to a retractable needle syringe. Typical retractable needle syringes provide a chamber within the plunger rod to house the needle cannula and other associated components after the retraction mechanism is activated. This requires increased component complexity to enable the sealed plunger and stopper to be breached during activation. The dual barrel design of the embodiments according to the second aspect moves the retraction mechanism into a dedicated region allowing a conventional plunger and stopper to be used.

Most conventionally designed retractable needles (single barrel designs with plunger activated retraction) are activated after dosing by a continued pressure on the rear of the plunger rod. As these are the same forces that must be applied during dispensing of the medication, inadvertent activation can occur. Specifically, such devices may be inadvertently activated during dosing if sufficient pressure is generated, i.e., during the expulsion of a viscous medication from the barrel, which requires higher forces to be applied and such forces may exceed the forces needed to activate the retraction mechanism. In other known devices, the pressure generated at the stopper may be sufficient to cause failure of the stopper or any removable opening into the plunger rod.

The retraction mechanisms of conventional type, plunger-activated safety syringes must withstand increased syringe pressures and the associated large plunger forces as described above. This leads to a requirement for large activation forces which exceed the operational forces by some safety margin in order to prevent premature retraction. Additionally, since most devices of this type employ an additional plunger motion after full dispensing, and in the same direction as the dispensing motion, a threshold force must be employed to allow the user to differentiate between a fully bottomed plunger and the activation operation.

By incorporating a separate release mechanism, distinct from the plunger rod, this limitation is removed in the dual barrel design, and the release activation force can be arbitrarily specified based on user requirements, ergonomics and safety considerations. Further, decoupling the retraction activation from the plunger rod allows for a separate and distinct control to be utilized for the needle retraction affording the operator greater control over when needle retraction occurs and removing the possibility of inadvertent actuation. Moreover, since the plunger rod and the stopper are no longer utilized with the retraction mechanism, existing plunger rods and stoppers from existing devices may be utilized with embodiments described herein.

A retractable syringe assembly 300 according to one or more embodiments of the second aspect is shown in FIGS. 24-29. The syringe assembly 300 includes a dual syringe barrel that includes fluid barrel 310 and a retraction barrel 320. The retractable syringe also includes a needle hub assembly 340, a plunger rod 360, stopper 370 and a trigger element 390. The fluid barrel shown in FIGS. 27A-D includes a distal end 311, a open proximal end 319, a sidewall 312 extending from the distal end 311 and the proximal end 319 including an inside surface 314 defining a chamber 315. The inside surface 314 defines a cross-sectional width and may include a reuse prevention feature, that will be discussed in greater detail below. The distal end 311 includes a distal wall 317 that encloses the distal end 311. In the embodiment shown, the sidewall 312 includes a first aperture 330 for permitting fluid communication between the fluid barrel and the retraction barrel. As will be discussed in greater detail below, the first aperture 330 also permits fluid communication between a needle cannula disposed within the retraction barrel 320 and the fluid barrel 310.

The fluid barrels shown in FIGS. 24-29 may include a reuse prevention feature. Specifically, the fluid barrel 310 may include a retaining element 309 that extends around the entire circumference of the inside surface 314 of the fluid barrel 310 at a location adjacent to the proximal end 319 of the fluid barrel. The cross-sectional width of the inside surface 314 at the retaining element is less than the first cross-sectional width or the cross-sectional width of the inside surface 314 at the remaining locations along the length of the fluid barrel. In one or more embodiments, optional tabs or detents can be used to create a region of the fluid barrel 310 having a cross-sectional width that is less than the first cross-sectional width of the fluid barrel 310. The retaining element may also be shaped to facilitate activation of the reuse prevention feature. For example, the fluid barrel 310 may also include a diameter transition region disposed proximally adjacent to the retaining element at the proximal end 319 of the fluid barrel 310. The cross-sectional width of the inside surface 314 of the fluid barrel at the diameter transition region increases from the distal end 311 to the proximal end 319 of the fluid barrel 310. As will be described in greater detail below, in embodiments of the retractable syringe assembly that utilize a reuse prevention feature, the reuse prevention feature of the fluid barrel 310 cooperates with corresponding reuse prevention features on the plunger rod 360 to lock the plunger rod 360 within the fluid barrel 310 and/or to disable the plunger rod 360 from further use.

As more clearly shown in FIGS. 27A-D, the retraction barrel 320 is disposed adjacent to the sidewall 312 of the fluid barrel 310. The retraction barrel 320 is configured to house a needle hub assembly 340 therein and the retraction feature. The retraction barrel 320 includes distal end 321 and an open proximal end 329. The distal end includes a tapered wall segment 232 that houses the needle hub assembly 340 therein. A wall 322 having an interior surface 324 defining the needle chamber 325 extends from the open distal end 321 to the open proximal end 329. The wall 322 of the retraction chamber is adjacent to the sidewall 312 of the fluid barrel 310. In one or more embodiments, the wall 322 may extend around the portions of the retraction barrel 320 that are not in direct contact with fluid barrel 310 and the sidewall 312 may form the barrier between the retraction barrel 320 and the fluid barrel 310. In other words, the outside surface of the sidewall 312 may form the interior surface 324 of the retraction barrel 320 along the portion of the retraction barrel 320 that is in direct contact with the fluid barrel 310.

The size of the needle chamber 325 may be modified to accommodate the needle hub assembly 340 and/or the retraction feature. According to one or more embodiments, the interior surface 324 of the retraction barrel 320 has a cross-sectional width that is smaller than the first cross-sectional width of the fluid barrel 310. In specific embodiments, the cross-sectional width of the interior surface 324 of the retraction barrel is less than about 90%, 80%, 70%, 60%, 50%, 40%, 30%, or 20% of the cross-sectional width of the inside surface 314 of the fluid barrel. Such designs in which the cross-sectional width of the interior surface 324 of the retraction barrel is less than the cross-sectional width of the inside surface 314 of the fluid barrel, provides ergonomic and functional advantages. For example, the overall appearance and handling of the dual barrel syringe is more appealing to the user. In certain embodiments, the retraction barrel can be nested within the fluid barrel. For example, both the retraction barrel and the fluid barrel may both be bounded or circumscribed by a common wall, and the retraction barrel may be partially or fully disposed within the fluid barrel, or alternatively, a dividing wall may separate a single barrel into two separate barrels, a fluid barrel and a retraction barrel.

The wall 322 may include a second aperture 332 that permits fluid communication with the fluid chamber 315 and the needle chamber 325. The second aperture of the wall may also allow fluid communication between the fluid chamber 315, needle chamber 325 and the needle cannula.

According to one or more embodiments, the retraction barrel a cross-sectional dimension that is smaller than the cross-sectional dimension of the fluid barrel. In specific embodiments, the cross sectional dimension of the retraction barrel is less than about 90%, 80%, 70%, 60%, 50%, 40%, 30%, or 20% of the cross-sectional dimension of the fluid barrel. Such designs in which the cross-sectional dimension of the retraction barrel is less than the cross-sectional dimension of the fluid barrel, provides ergonomic and functional advantages. For example, the overall appearance and handling of the dual barrel syringe is more pleasing to the user The needle hub assembly may include a fluid path 354 that extends from an open end of the needle cannula to second aperture 332 of the retraction barrel. The second conduit may include an opening (not shown) that must be aligned with the second aperture to permit fluid communication between the needle cannula and the fluid barrel.

Referring to FIGS. 28 and 28A, the needle hub assembly 340 disposed within the retraction barrel 320 and includes a needle hub 342 and a needle cannula 350 attached to the needle hub 342. The needle hub 342 includes a distal end 341 and a proximal end 349. The needle cannula 350 includes a free and open distal end 351 end and an open proximal end 359 that is attached to the distal end 341 of the needle hub. The needle hub 342 shown in FIGS. 28 and 28A includes a recessed portion 355 for partially housing one end of the needle cannula. The recessed portion 355 is in fluid communication with the fluid path 354 to permit fluid communication between the needle cannula 350 and the fluid barrel 310.

The needle cannula 350 of the needle hub assembly 340 is biased to move in the proximal direction. In the embodiment shown, the needle hub assembly 340 is biased to move in the proximal direction, thereby biasing the attached needle cannula 350. The needle hub assembly 340 is biased to move in the proximal direction by a biasing element 352 disposed between the needle cannula 350 and the tapered wall segment 323 of the retraction barrel. As shown more fully in FIGS. 26-27, the biasing element 352 is shown as surrounding the needle cannula 350.

In the embodiment shown, the biasing element 352 engages the needle cannula 350. The biasing element 352 may include a spring, which may be a compression spring that applies a constant force on the needle hub 342 in the proximal direction. In alternative embodiments, the biasing element 352 may be provided in another form, for example, a lever arm (not shown) may be disposed between the needle hub and the barrier wall. The needle hub 342 includes at least one hub seal 343 disposed along the outside surface of the needle hub 342 for forming a fluid tight seal with the tapered wall segment 323 of the retraction barrel. As will be described in greater detail below, the trigger element 390 supports the needle hub 342 and prevents biasing element 352 from moving in the proximal direction. The needle hub 342 includes at least one detent 344 that receives and engages the corresponding structure on the trigger element 390 that supports the needle hub 342. As will be explained in greater detail below, disengaging the detent 344 from the corresponding structure on the trigger element will allow the biased needle hub 342 and the needle cannula 350 attached thereto to retract into the retraction barrel 320.

Figure 25:
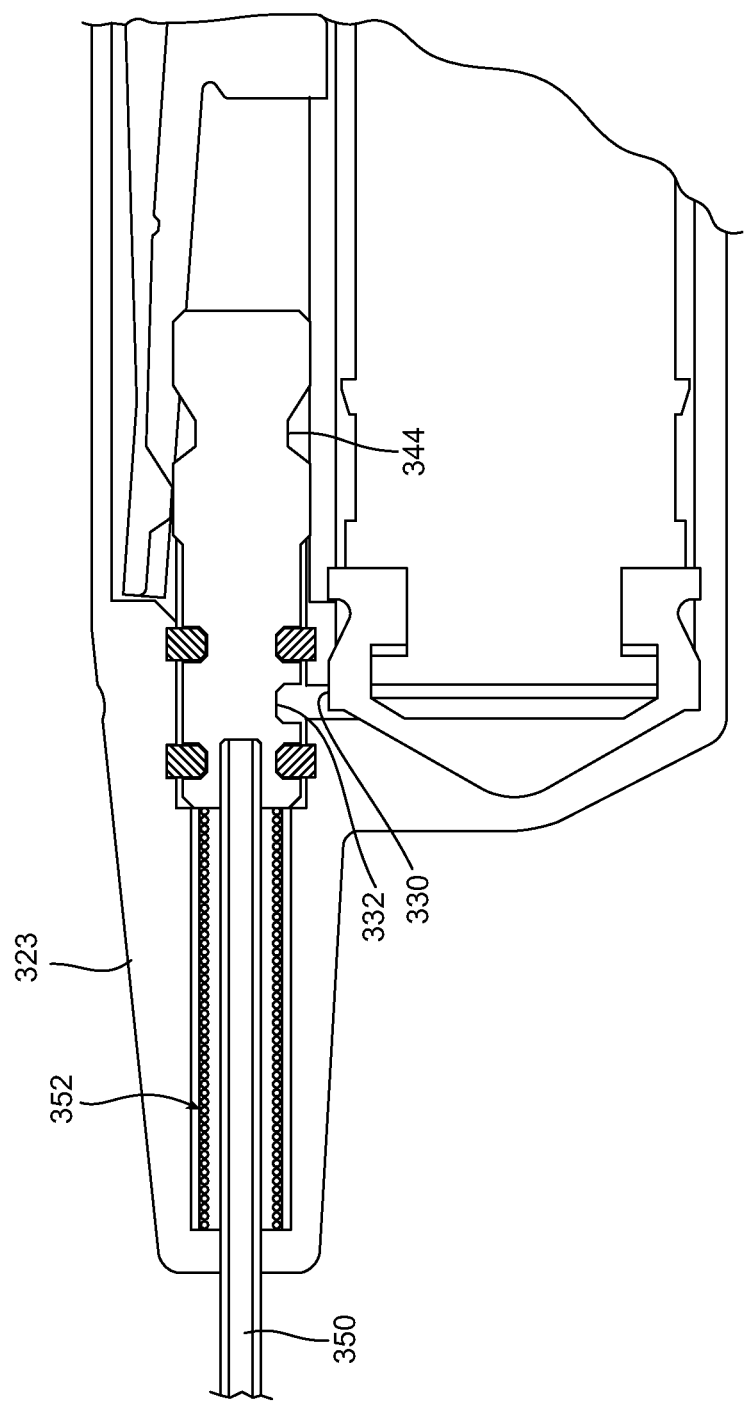
FIG. 25 illustrates an enlarged partial cross-sectional view of the retractable syringe assembly shown in FIG. 24.
Figure 26:
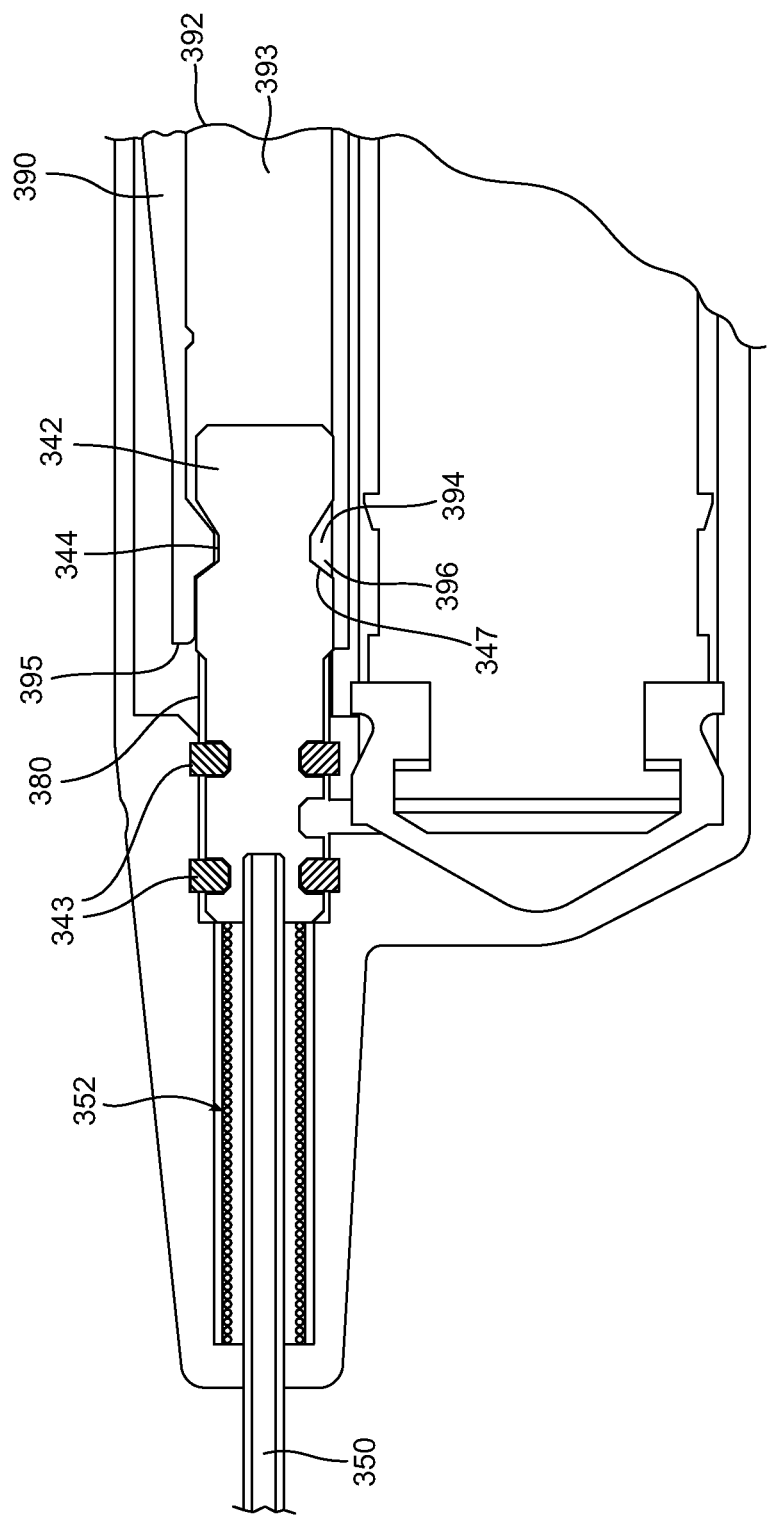
FIG. 26 illustrates an enlarged partial cross-sectional view of the retractable syringe assembly shown in FIG. 25 after application of the trigger force on the needle hub assembly.
Figure 27A:
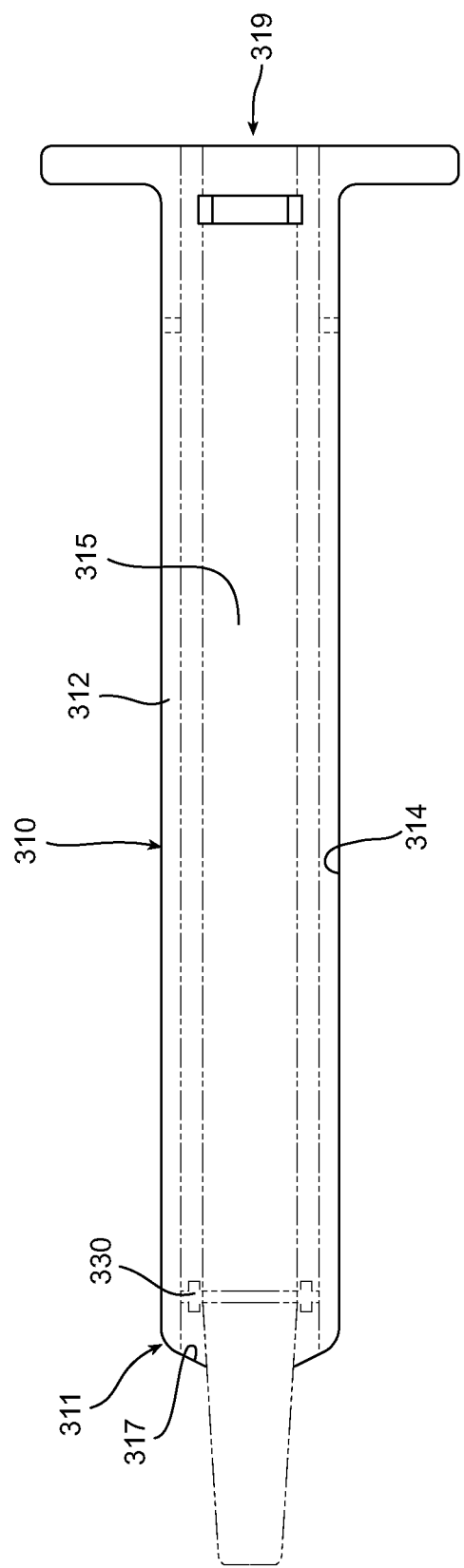
FIG. 27A illustrates a cross-sectional top view of the dual chamber syringe barrel shown in FIG. 24.
Figure 27B:
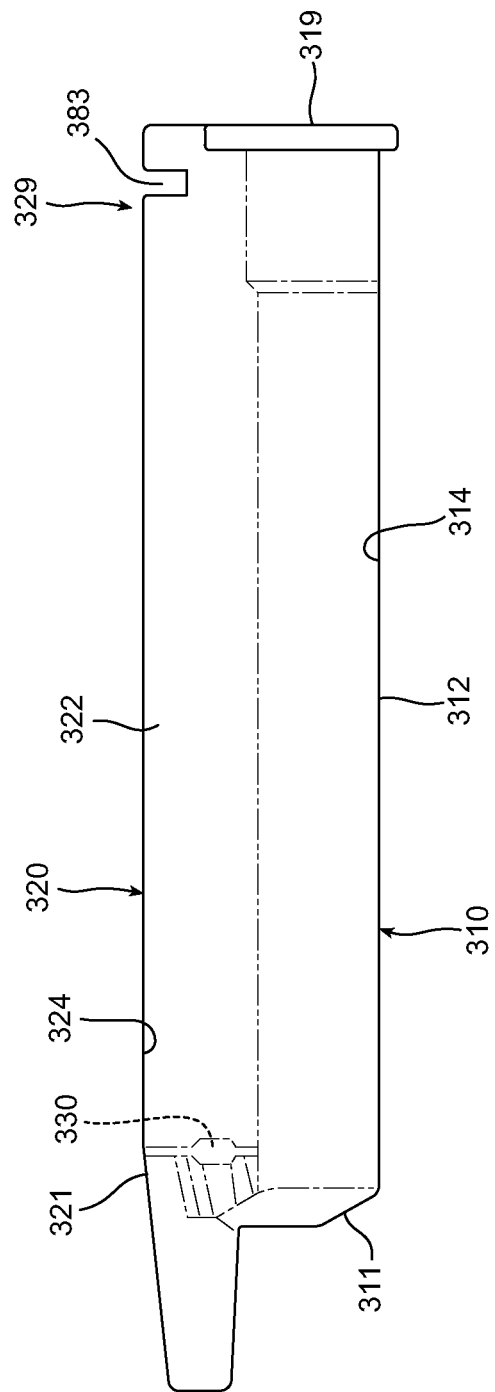
FIG. 27B illustrates a cross-sectional side view of the dual chamber syringe barrel shown in FIG. 27A.
Figure 27C:
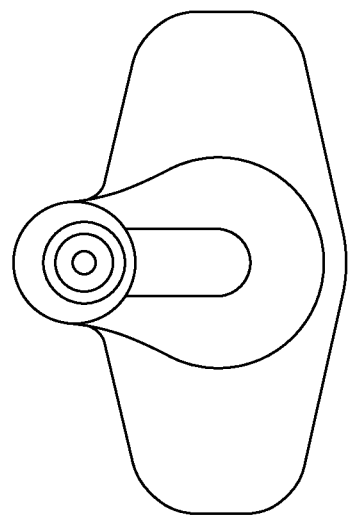
FIG. 27C illustrates a cross-sectional view of the dual chamber syringe barrel shown in FIG. 27A taken from the proximal end.
Figure 27D:
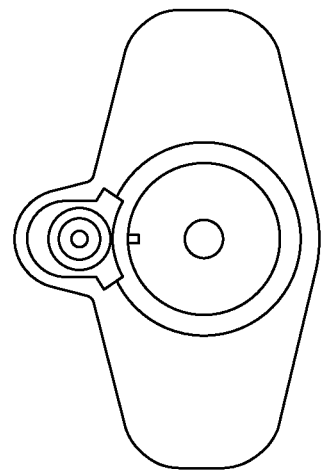
FIG. 27D illustrates a cross-sectional side view of the dual chamber syringe barrel shown in FIG. 27A taken from the distal end.

In the embodiment shown, for example in FIGS. 25, 28 and 28A, the needle hub 342 includes a first attachment portion. In the embodiment shown, the first attachment portion is provided in the form of at least two detents 344 or grooves 345 disposed on opposite ends of the needle hub 342. The grooves 345 are disposed adjacent to the proximal end 349 of the needle hub assembly. The grooves are shown as including a first portion inclined radially inwardly into the needle hub 342, a second portion that has no incline and is substantially parallel to the axis along which the needle hub is disposed, and a third portion that inclines sharply radially outwardly. The first attachment portion facilitates engagement of the trigger element 390 with the grooves 345. The third portion 347 prevents disengagement of the trigger element 390 until a sufficient force is applied to the trigger element 390. Specifically, the sharp incline of the third portion 347 prevents the trigger element from sliding over and out of the detent 344, when engaged with the detent 344. Once a sufficient force is applied to the trigger rod 390 to overcome the third portion 347 of the detent 344, referred herein as the trigger force, the disengagement of the trigger element 390 from the needle hub 342 permits the biasing element 352 to move the needle cannula 350 and the needle hub 342 attached thereto into the trigger element 390 and/or the retraction barrel 320. Specifically, the expansion of the biasing element 352 drives the needle cannula 350 and the needle hub 342 into the trigger element 390 and/or the retraction barrel 320.

The needle hub assembly is sized moveable within the needle chamber. The size and shape of the needle hub assembly may be modified to permit movement in needle chambers having different sizes. In the assembled state, prior to use, the needle hub assembly is positioned at the open distal end of the retraction barrel.

A plunger rod 360 is disposed within the fluid barrel 310 and includes a stopper 370 attached thereto for forming a fluid-tight seal with the inside surface 314 of the fluid barrel 310. The plunger rod 360 may include a reuse prevention feature that locks the plunger rod 360 within the fluid barrel 310 or otherwise disables the plunger rod 360. The plunger rod may include a reuse prevention feature that cooperates with a reuse prevention feature disposed on the fluid barrel 310. In one or more embodiments, the plunger rod may include a protrusion 313 that has a cross-sectional width that is greater than the cross-sectional width of the inside surface 314 of the fluid barrel 310 at the retaining element 309. As discussed above, the retaining element form a smaller cross-sectional width than at other locations along the length of the fluid barrel 310. Accordingly, when the protrusion of the plunger rod advances distally past the retaining element of the fluid barrel 310, the smaller cross-sectional width of the retaining element prevents movement of the protrusion in the proximal direction. Accordingly, the plunger rod 360 is locked within the fluid barrel 310 by the retaining element. In one or more embodiments, the stopper 370 and/or the plunger rod 360 may have a structure to permit relative movement of the plunger rod 360 with respect to the stopper 370. For example, the stopper 370 may have an interior recess that allows the distal end of the plunger rod 360 to move in the distal and proximal directions within the interior recess, thus elongating and shortening the length of the plunger rod and the stopper. Exemplary plunger rods and stoppers which permit relative movement of the plunger rod with respect to the stopper are disclosed in U.S. application Ser. Nos. 12/137,732 and 12/262,836 referred to above and are incorporated herein by reference.

The stopper 370 may also include reuse prevention features that also cooperates with reuse prevention features disposed on the fluid barrel 310. For example, the stopper 370 may include a sealing portion (not shown) that has a cross-sectional width that is greater than the cross-sectional width of the inside surface 314 of the fluid barrel 310 at the retaining element. In such embodiments, removal of the stopper 370 is prevented because the smaller cross-sectional width of the retaining element of the fluid barrel 310 prevents the stopper 370 from being removed. The plunger rod 360 and the stopper 370 may be joined by a frangible connection 372 that may cause the plunger rod 360 to become disconnected from the stopper 370, while the stopper 370 remains locked within the fluid barrel 310 by the retaining ring. Exemplary stoppers which include a reuse prevention feature and plunger rods and stoppers joined by a frangible connection are disclosed in U.S. application Ser. Nos. 12/137,732 and 12/262,836 and are incorporated herein by reference.

The retractable syringe assembly 300 also includes a trigger element 390 that includes a distal end 391 and a proximal end 399. The trigger element 390 is moveable independently of the plunger rod 360 and extends into the needle chamber 325 of the retraction barrel 320. In the embodiment shown, the trigger element 390 includes a trigger pad 394 on which the user applies a force in the distal direction to activate the retraction mechanism of the syringe assembly.

The trigger element 390 includes a trigger element body 392 that extends from the distal end 391 to the proximal end 399. The trigger element body 392 is shaped to have a cylindrical shape and is elongate. In the embodiment shown, the trigger element 390 has an open distal end 391 and the trigger element body 392 has a hollow interior 393 to house the needle hub 342 and the needle cannula 350. The proximal end 399 of the trigger element is closed and may be tapered to retain the needle hub 342 within the hollow interior 393 after the needle hub 342 and the needle cannula 350 is retracted into retraction barrel. The needle cannula 350 may also include structure to retain the retracted needle cannula 350 within the trigger element 390.

The distal end 391 of the trigger element 390 includes a second attachment portion 394 for engaging the first attachment portion. In the embodiment shown, the second attachment portion includes at least one flexible arm 395 that extends distally from the trigger element body 393. The flexible arm 395 includes a release member 396 that is shaped, sized and positioned to engage the grooves 345 of the needle hub 342. Specifically, the detent includes a first segment 346 that is inclined radially inwardly, a second portion that has no incline and is substantially parallel to the axis along which the trigger element 390 is disposed, and a third segment 347 that inclines sharply radially outwardly. It will be understood that the release member 396 may have another shape or size that does not replicate the shape and size of the grooves 345.

The interior surface 324 of the retraction barrel may include a capture rib 380 for capturing or retaining the flexible arm 395 of the trigger element 390 upon application of the trigger force. Specifically, the capture rib 380 is disposed adjacent to the tapered wall segment 323 and extends into the needle chamber 325. The capture rib has a distal end that is attached to the interior surface of the retraction barrel and a free proximal end that extends into the needle chamber 325. The capture rib 380 is contoured to facilitate the distal end 391 of the trigger element 390 to slide over or ride over the capture rib 380 upon application of a trigger force that permits the release member 396 to disengage from the grooves 345 and the trigger rod moves in the distal direction. As shown more clearly in FIG. 26, as the flexible arm 395 of the trigger element 390 slides over the capture rib 380, the flexible arm 395 flexes or moves outwardly. The capture rib 380 holds the flexible arm 395 in the flexed position and permits the needle hub 342, the needle cannula 350 and the biasing element 352 to move proximally past the release member 396 into the hollow interior 393 of the trigger element.

The retraction barrel 320 includes a release opening 383 disposed adjacent to the proximal end of the retraction barrel. The release opening 383 may be enclosed to form an indentation in the wall 322 of the retraction barrel. The trigger element 390 includes a release detent 397 disposed on the trigger element body 392 that engages the release opening 383. The release opening 383 and the release detent 397 provide an indication to the user for how much force is sufficient to overcome the grooves 345 of the needle hub 342. This indication can be a visual indication, a tactile indication, or a combination of visual and tactile indication. Specifically, the force required to disengage the release detent 397 from the release opening 383 is the same or substantially the same as the trigger force. The height of the release detent 397 may be modified to require more or less force to disengage the release detent 397 from the release opening 383. In addition, the release opening 383 may be modified to have curved entrances to decrease the angle between the interior surface of the wall 322 and the release opening 383. In embodiments where the release opening 383 is open and not enclosed, the release opening 383 and the release detent 397 provide visual indication whether the trigger force has been applied. Specifically, the user can see whether the release detent 397 is engaged with the release opening 383 and know whether the trigger force has been applied.

In one or more embodiments, the trigger force, which is the force required to disengage the release detent 397 from the release opening 383 and/or to disengage the release member 396 from the groove 345 is at least about 4 pounds of force (lbf). In one or more variants, the trigger force is about 4 lbf. In another variant, the trigger force may include 2 lbf, 3 lbf, 4 lbf, 5 lbf, or 6 lbf. In a more specific embodiment, the trigger force is in the range from about 3.5 lbf to about 4.5 lbf.

In the embodiment shown, the needle hub assembly is permanently attached to the retraction barrel 320 because it is enclosed within the retraction barrel. In one or more alternative embodiments, the needle hub assembly may be removably attached to the retraction barrel 320 or may be attached by the user to the open distal end 321 of the retraction barrel.

Referring to FIG. 29, the length of the plunger rod 360, the trigger element 390 and the syringe barrel 301 may be modified so that the plunger rod 360 aligns with the trigger element upon expulsion of all of the contents of the syringe, as shown in FIG. 29. The alignment of the plunger rod 360 and the trigger element 390 provides one or more of visual indication and tactile indication that the contents of the fluid barrel 310 have been expelled and the needle cannula 350 can be retracted into the retraction barrel. Further, such alignment of the trigger element 390 and the plunger rod 360 after the stopper 370 is in contact with the distal wall 317 of the fluid barrel 310 requires that the trigger element 390 is not aligned with the plunger rod 360 when the fluid barrel is filled. Specifically, the trigger element 390 is located closer to the proximal end 329 of the retraction barrel and the proximal end 319 of the fluid barrel than the plunger rod 360. This alignment, when retraction of the needle cannula is not desired, reduces the chance of inadvertent activation of the retraction mechanism.

Figure 30:
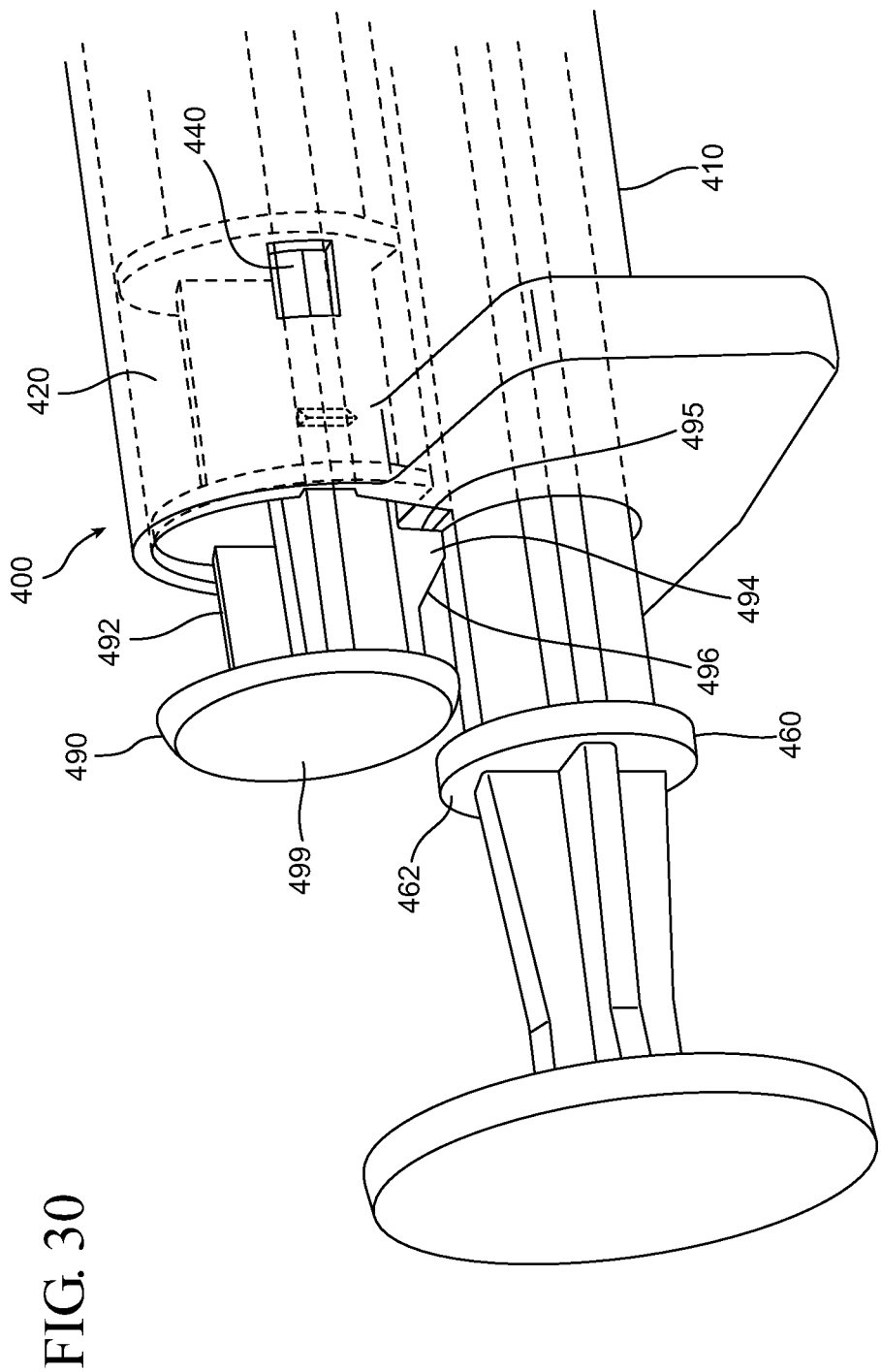
FIG. 30 illustrates the proximal end of a retractable syringe assembly according to one or more embodiments.
Figure 31:
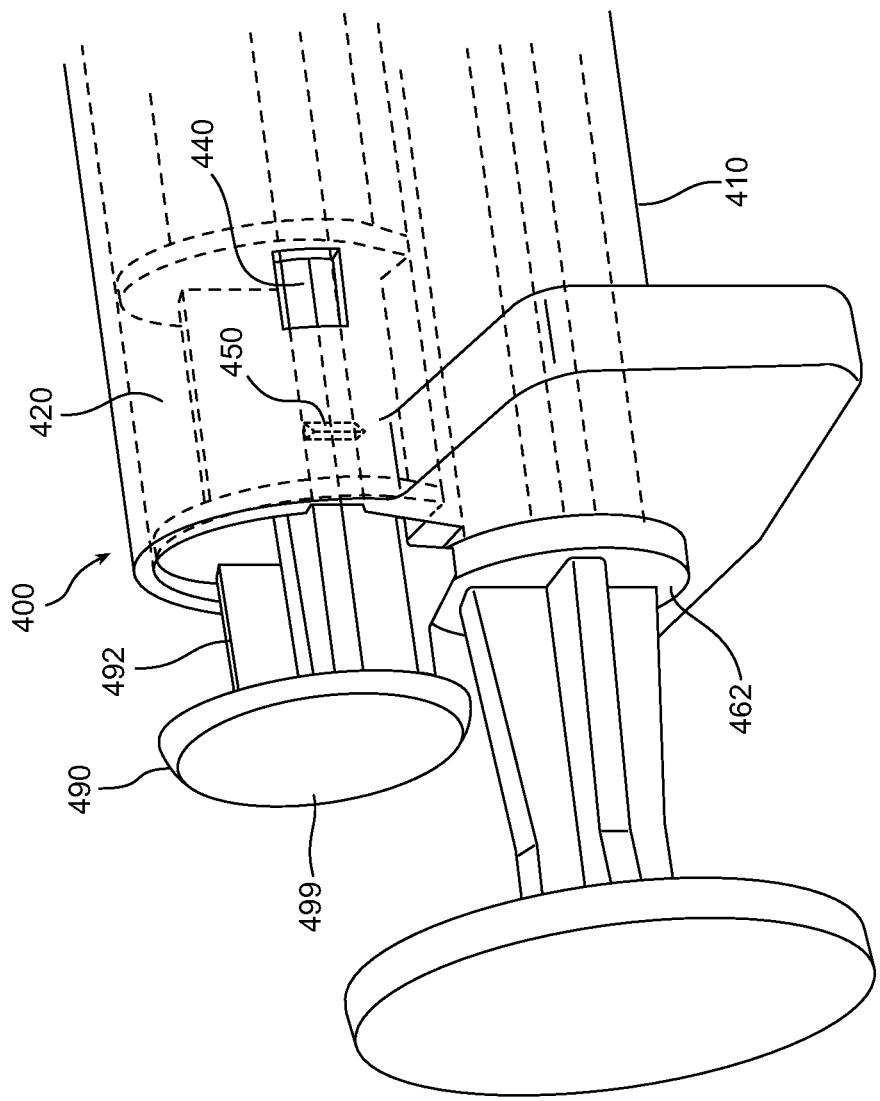
FIG. 31 illustrates the proximal end of a retractable syringe assembly shown in FIG. 30 after application of a force on the plunger rod in the distal direction.
Figure 32:
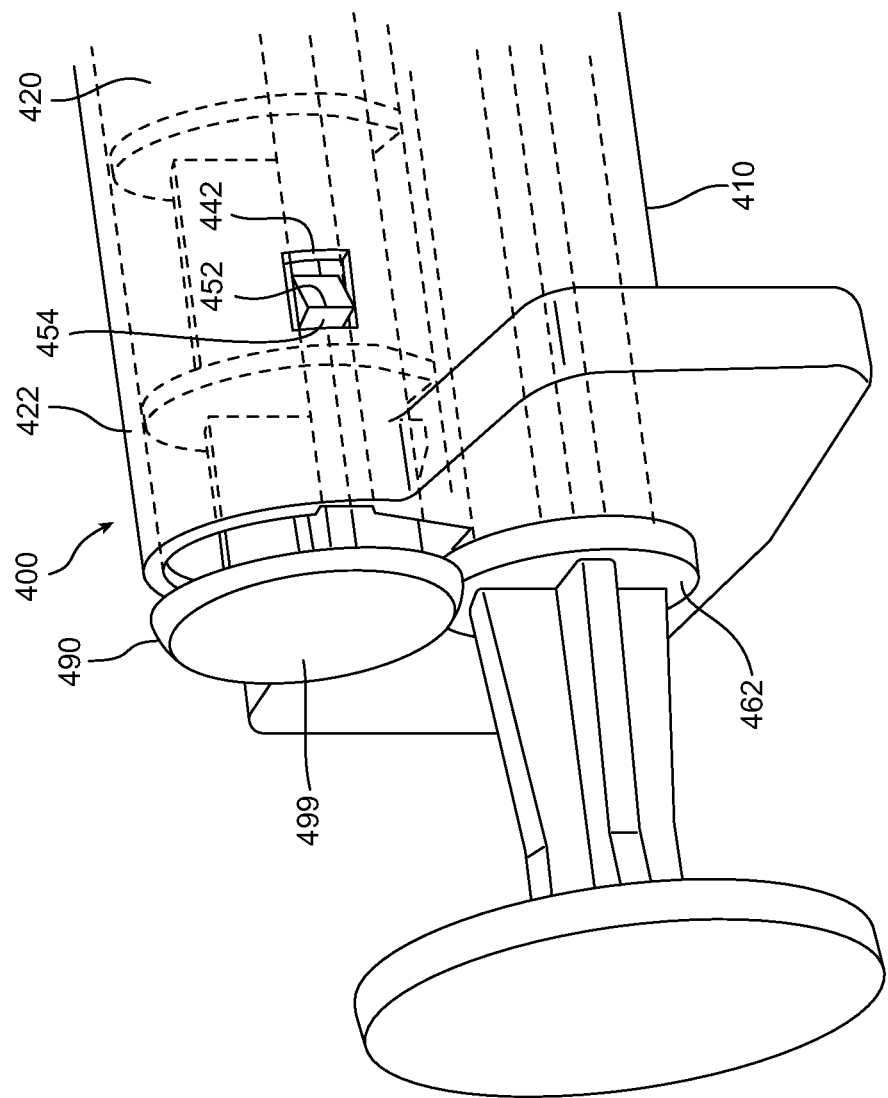
FIG. 32 illustrates the proximal end of a retractable syringe assembly shown in FIG. 31 the trigger element locked within the retraction barrel after application of a force on the trigger element in the distal direction.
Figure 33:
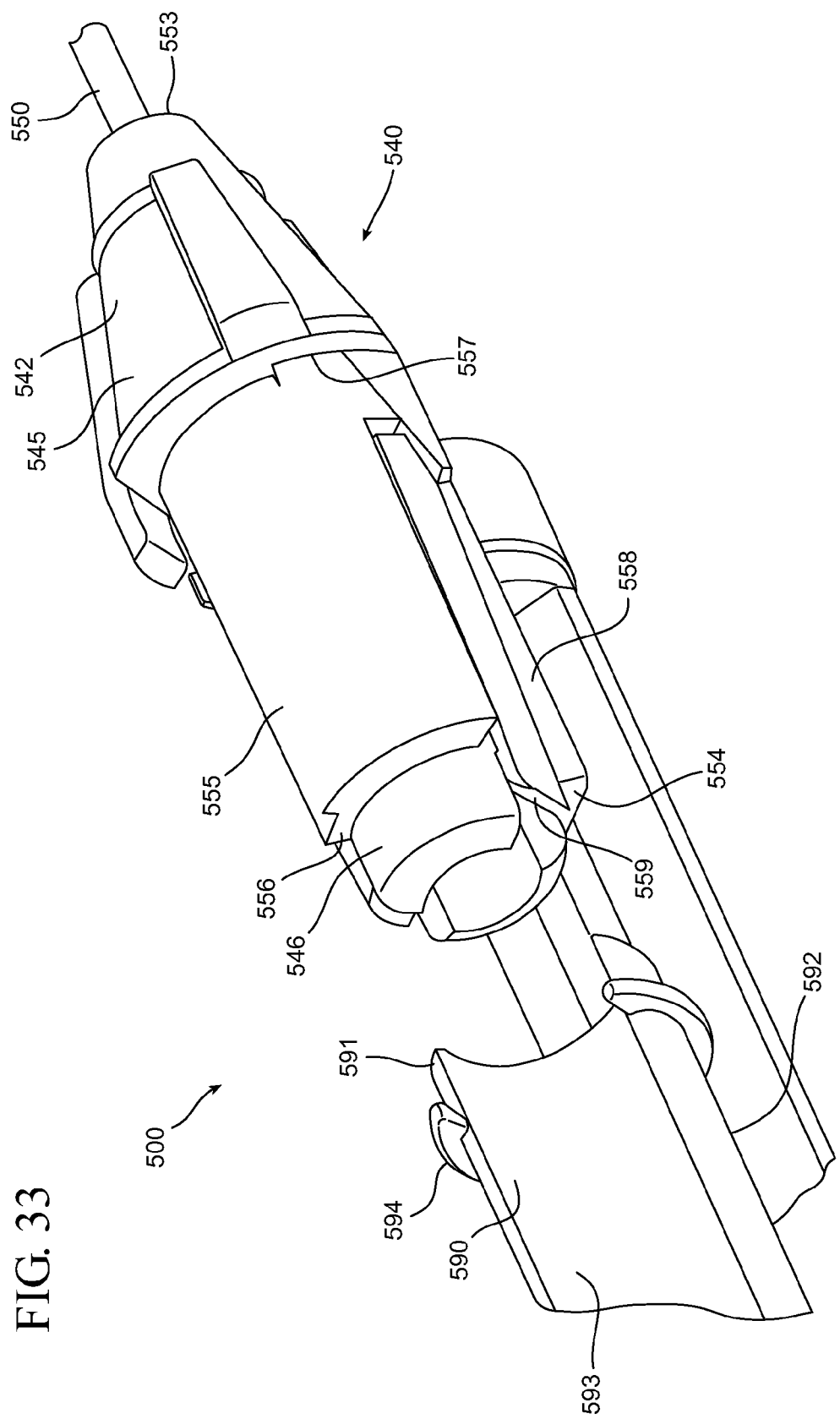
FIG. 33 illustrates a partial perspective view of a plunger rod, trigger element and needle hub assembly according to one or more embodiments.
Figure 34:
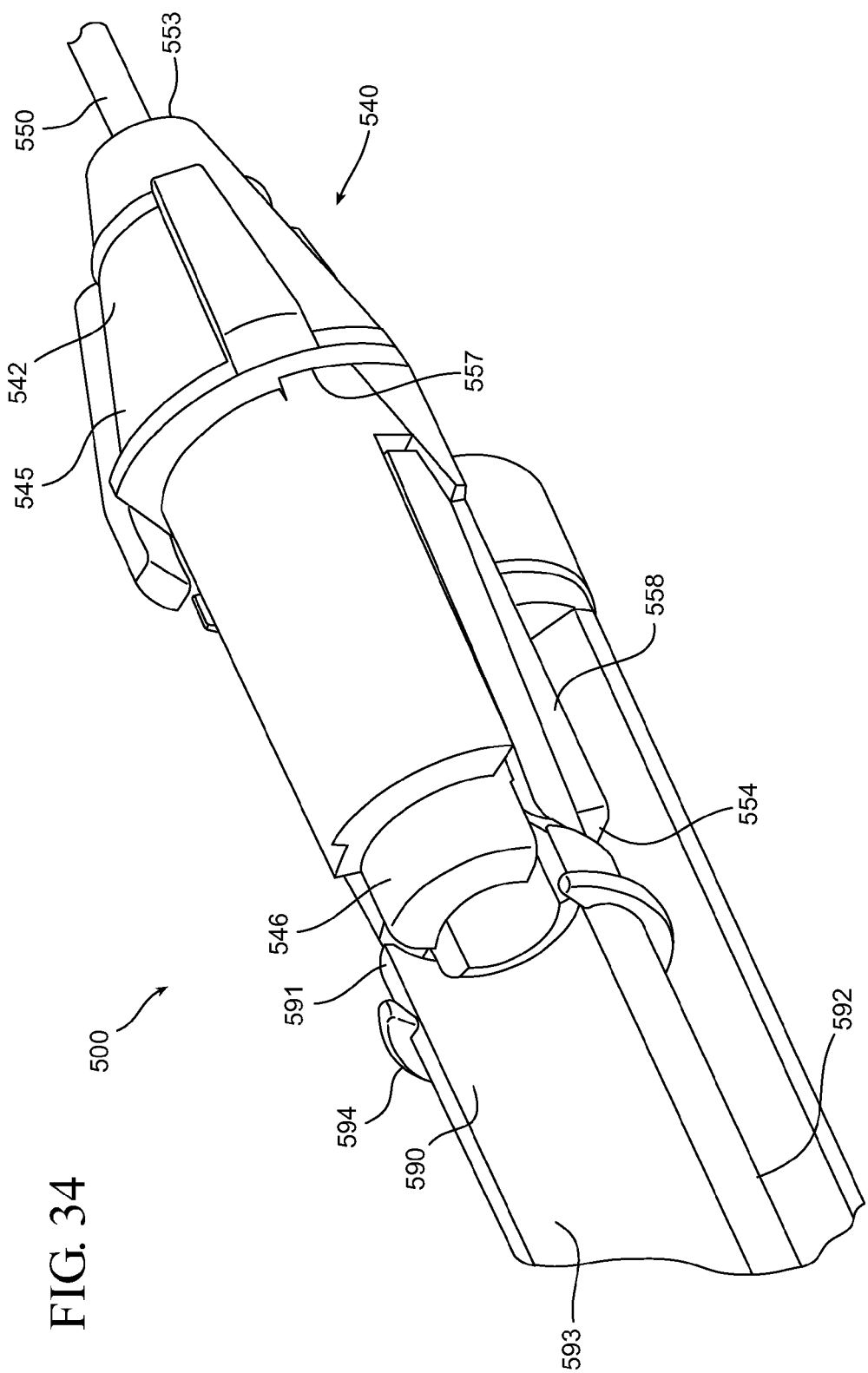
FIG. 34 illustrates a partial perspective view of a plunger rod, trigger element and needle hub assembly shown in FIG. 33 after application of a force on the trigger element in the distal direction.
Figure 35:
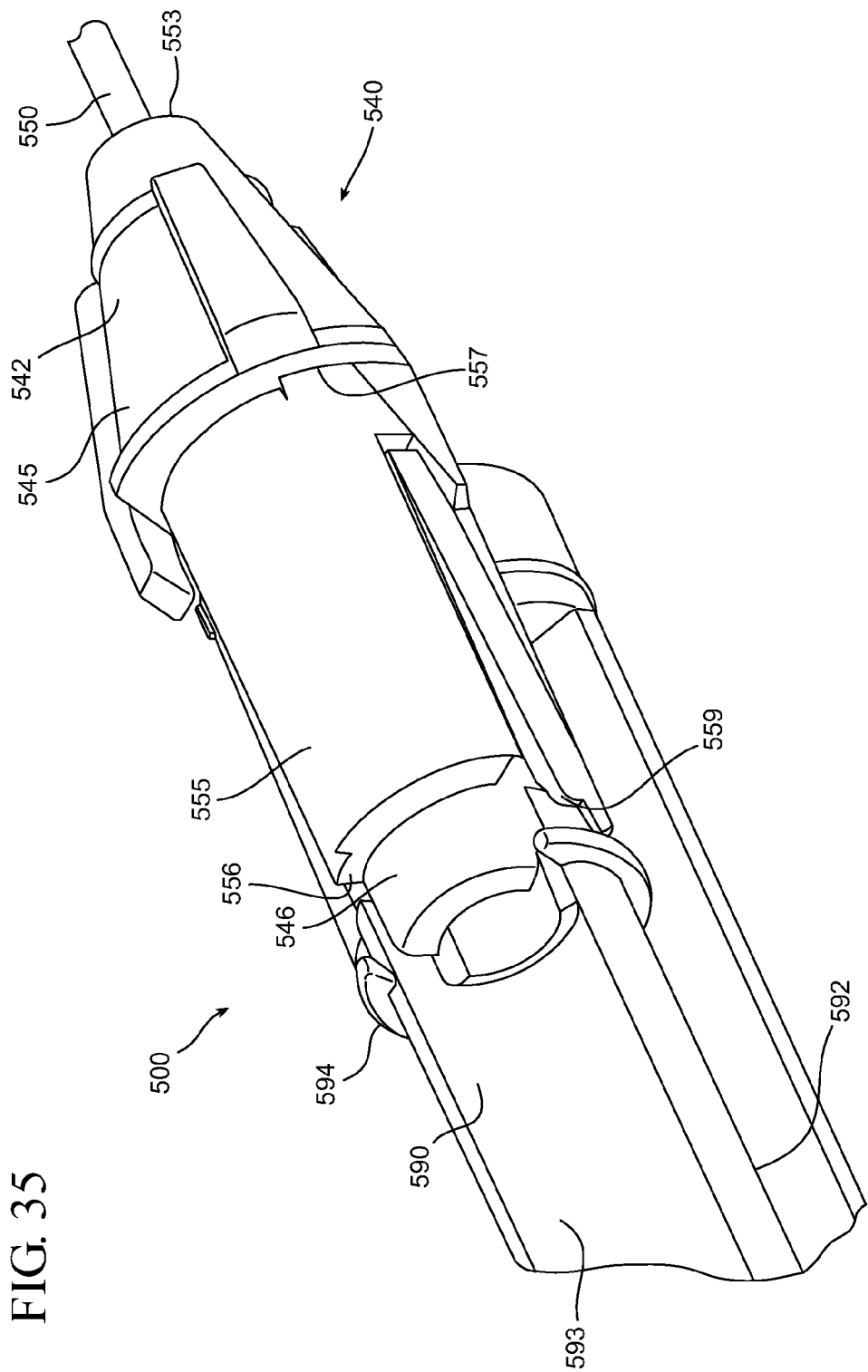
FIG. 35 illustrate a partial perspective view of a plunger rod, trigger element and needle hub assembly shown in FIG. 34 during application of a force on the trigger element in the distal direction, as the trigger element contacts the needle hub assembly.
Figure 36:
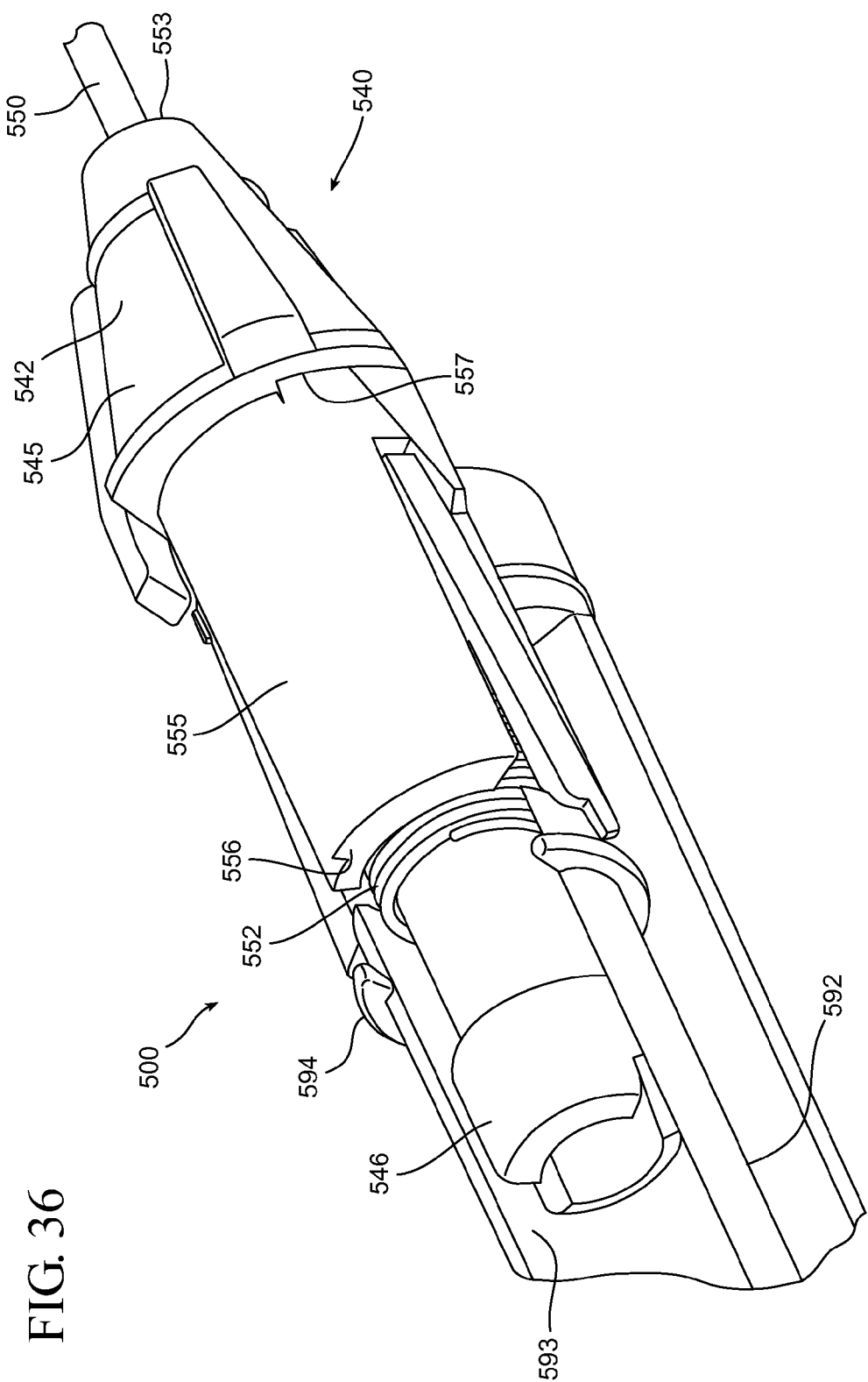
FIG. 36 illustrates a partial perspective view of a plunger rod, trigger element and needle hub assembly shown in FIG. 35 after the trigger element contacts the needle hub assembly, as the trigger element exerts a trigger force on the needle hub assembly.
Figure 37:
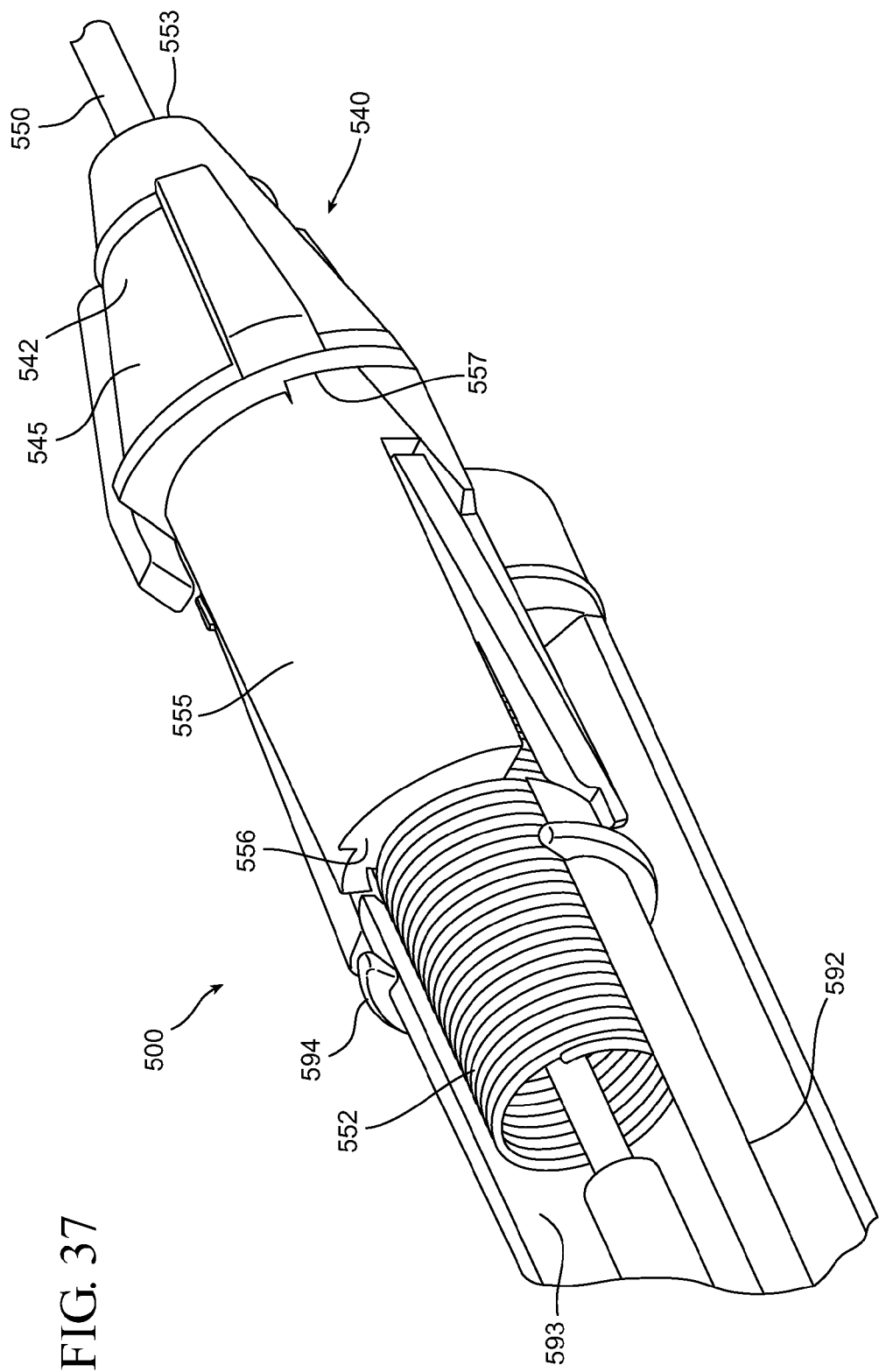
FIG. 37 illustrates a partial perspective view of a plunger rod, trigger element and needle hub assembly shown in FIG. 36 after a portion of the needle hub assembly is retracted into trigger element.
Figure 38:
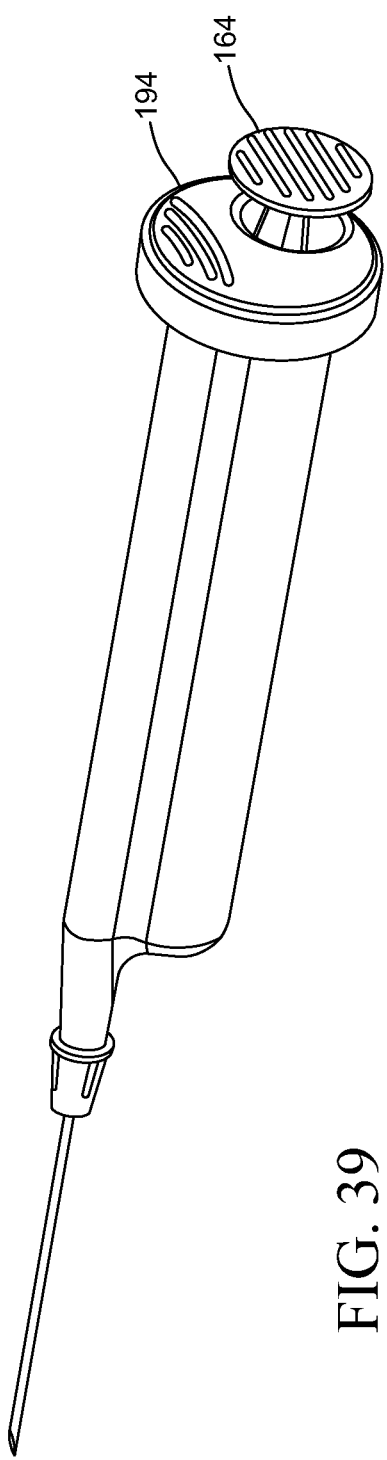
FIG. 38 illustrates a perspective view of a retractable syringe assembly according to one or more embodiments.
Figure 39:
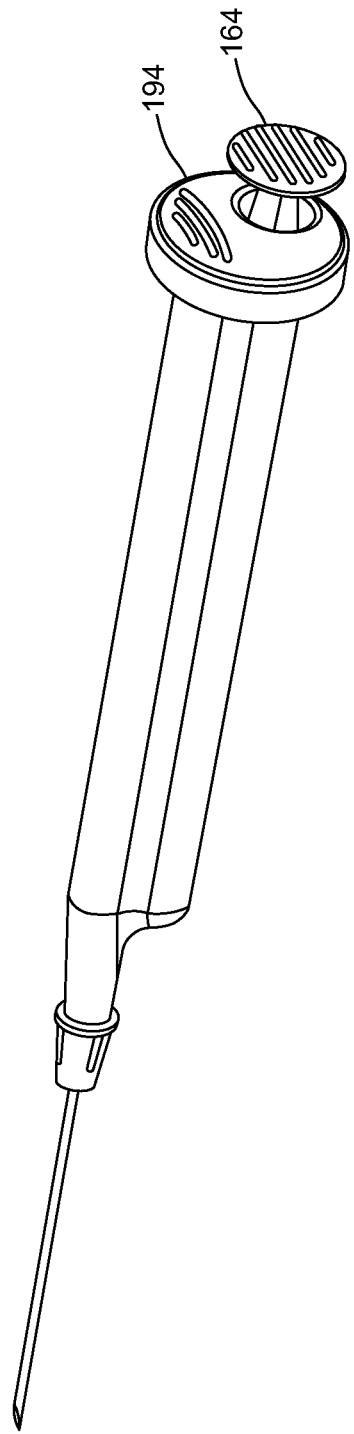
FIG. 39 illustrates a perspective view of a retractable syringe assembly according to one or more embodiments.
Figure 38A:
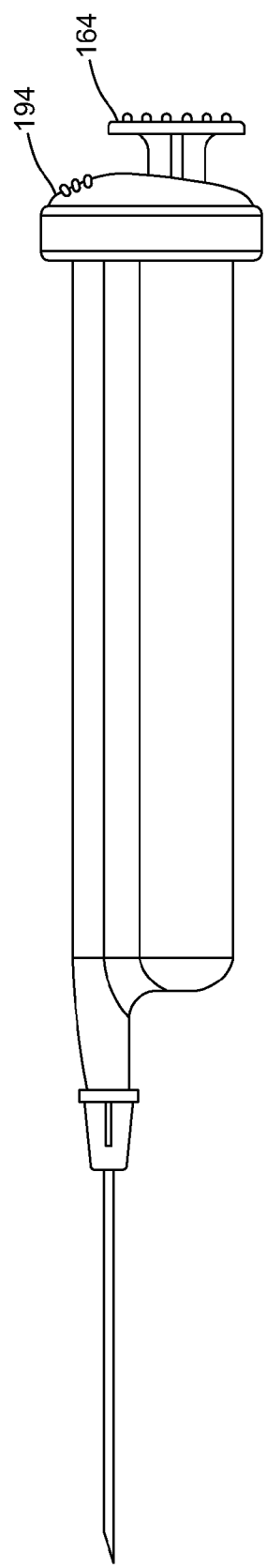
FIG. 38A illustrates a side view of the retractable syringe assembly shown in FIG. 38.
Figure 38B:
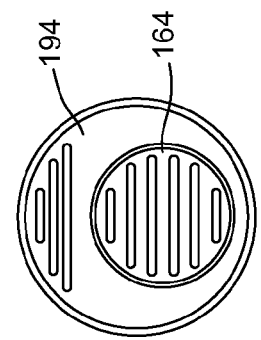
FIG. 38B illustrates a view of the retractable syringe assembly shown in FIG. 38 taken from the proximal end.

A third aspect of the present invention pertains to a retractable syringe assembly that incorporates structure to prevent premature activation of the retraction mechanism. The retractable syringe assembly is shown in FIGS. 30-32. In the embodiments shown in FIGS. 30 and 32, the syringe assembly 400 includes a dual syringe barrel as otherwise described herein that includes a retraction barrel 420 and a fluid barrel 410. A trigger element 490 is disposed within the retraction barrel 420 and a plunger rod 460 is disposed within the fluid barrel 410. The plunger rod 460 and the trigger element 490 have features that prevent the plunger rod from interacting with the trigger element 490 and accidentally activating the trigger element 490. In addition, the plunger rod 460 and the trigger element 490 have reuse prevention features that prevent the user from reusing the syringe assembly 400. These premature activation prevention features and reuse prevention features of the trigger element 490 and the plunger rod 460 described with respect to the third aspect may be incorporated with other trigger elements and plunger rods described herein.

The trigger element 490 includes a distal end (not shown) and a proximal end 499 and a trigger element body 492 that extends from the distal end to the proximal end 499. A snap 494 is disposed adjacent to the proximal end 499. In the embodiment shown, the snap 494 is located between the trigger element 490 and the plunger rod 460. The snap 494 engages the retraction barrel and the engagement therebetween hinders or prevents movement of the trigger element 490 in the distal direction. As shown in FIG. 30, the snap 494 is shown as a radially outward extension that extends from the trigger element body 492. The snap 494 includes a distal end 495 and a proximal end 496. The snap 494 has a height that increases from the proximal end 496 to the distal end 495 to permit or facilitate movement of the plunger rod 460 past the snap 494. The distal end 495 of the snap 494 is shown as substantially perpendicular to the trigger element body The snap element 494 is depressible upon application of a force in the distal direction. The snap element 494 is not depressible upon application of a force in the proximal direction. Accordingly, the engagement of the snap element 494 with the retraction barrel 420 applies a force on the snap element 494 in the proximal direction, which prevents the snap element from depressing and hinders movement of the trigger element 490 in the distal direction. When the plunger rod 460 is moved in the distal direction, it depresses the snap element 494 and permits movement of the trigger element 490 in the distal direction. The plunger rod 460 may include a contacting surface, shown in FIGS. 30-32 as a flat radial ring 462, that deflects the snap element 494 so the trigger element 494 may be moved in the distal direction and the activation of the retraction mechanism can proceed.

In use, as shown in FIGS. 31-32, the movement of the plunger rod in the distal direction to expel all the contents of the fluid barrel 410 depresses the snap element 494. When the plunger rod is bottomed or when all the contents of the fluid barrel 410 are expelled and the stopper is in contact with the distal end of the fluid barrel, the plunger rod continues to depress the snap element 494. The depression of the snap element 494 permits movement of the trigger element 490 only after the contents of the syringe are expelled. Accordingly, premature activation of the retraction mechanism is prevented.

The underlying principle of the snap element 494 is that the inclusion of an abrupt angled surface, which can be as much as 90 degrees), engages the retraction barrel and prevents distal movement of the trigger element. The snap element 494 may have sufficient stiffness in the axial direction but may be easily deflectable in the radial direction. This ensures smooth deflection when the plunger rod engages the snap element 494.

Figure 58:
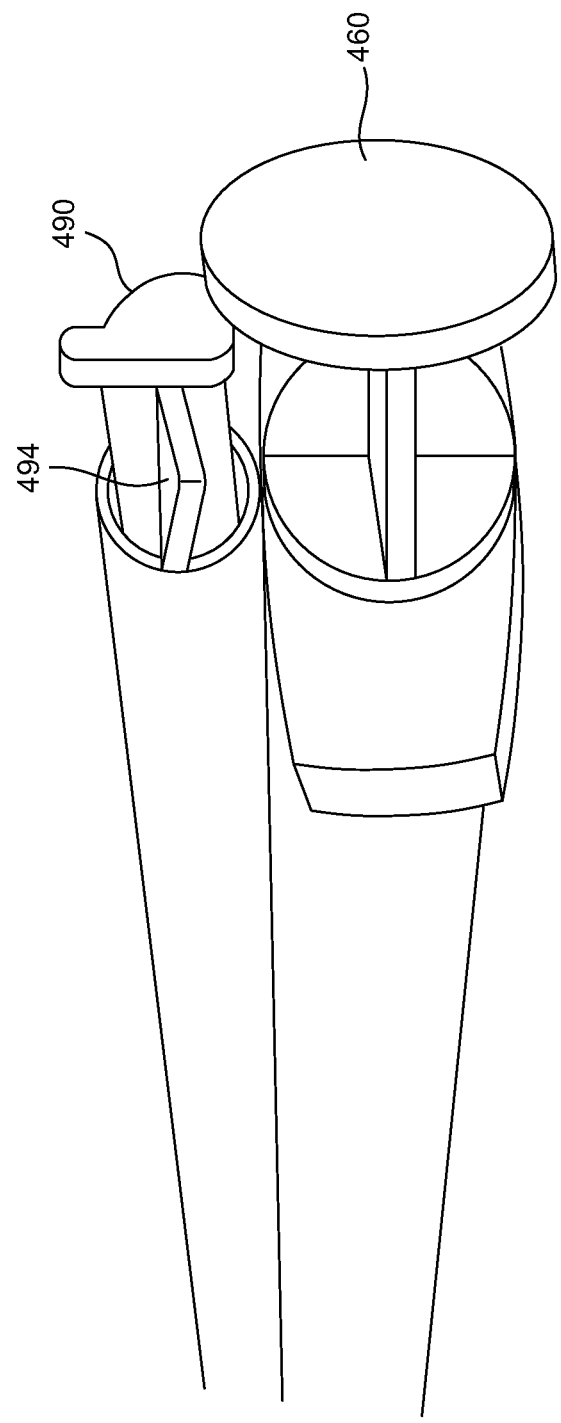
FIG. 58 illustrates a perspective view of the proximal end of a retractable syringe assembly according to one or more embodiments.
Figure 59:
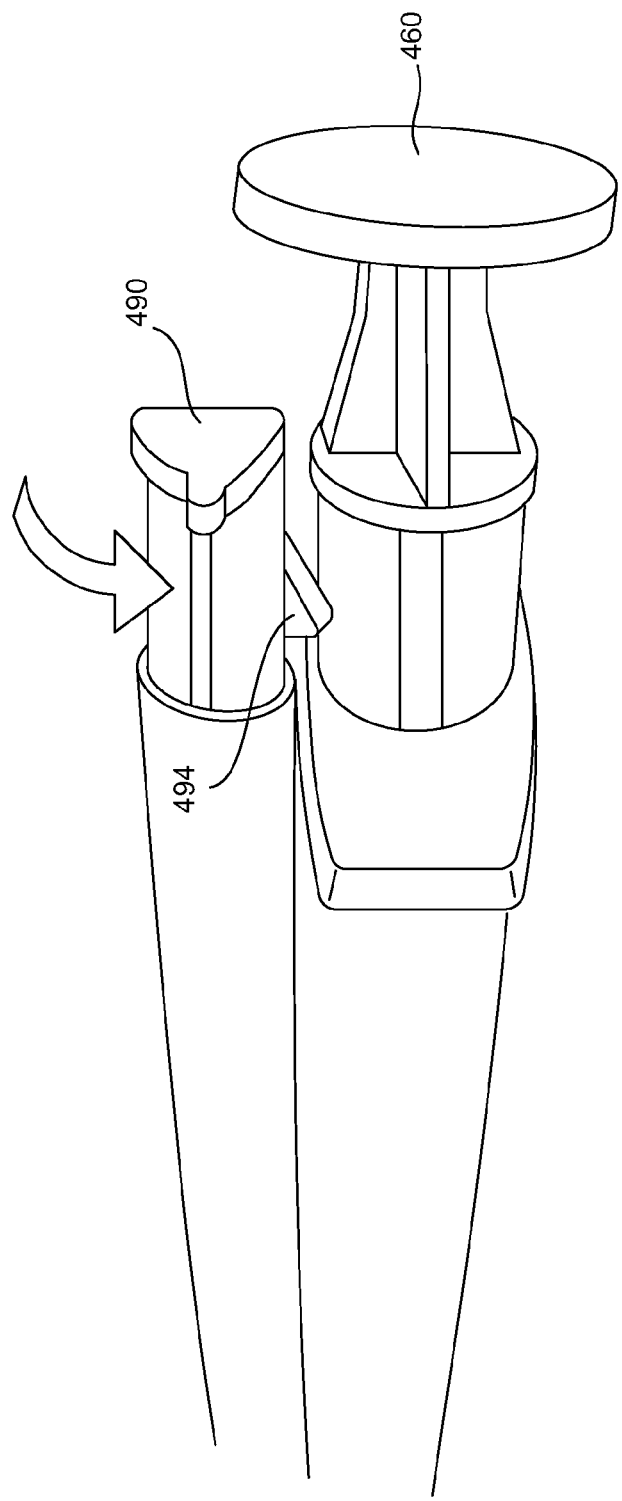
FIG. 59 illustrates a perspective view of the proximal end of a retractable syringe assembly shown in FIG. 58 after rotation of the trigger element to prevent movement of the trigger element in the distal direction.
Figure 60:
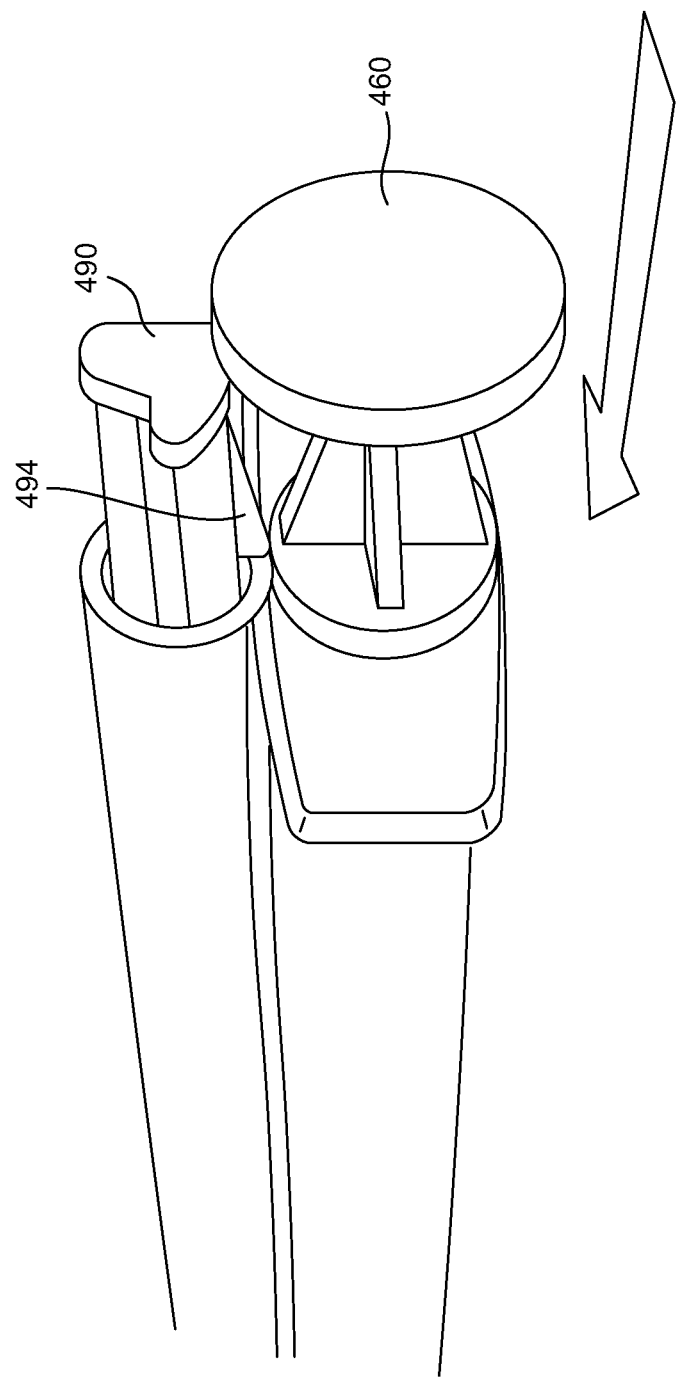
FIG. 60 illustrates a perspective view of the proximal end of a retractable syringe assembly shown in FIG. 59 after rotation of the trigger element to permit movement of the trigger element in the distal direction.

In one or more embodiments, the snap element 494 may be rotatable so it may be to be turned away during transport and storage, as shown in FIGS. 58-60. Prior to use or prior to activation, as shown in FIG. 58, the trigger element 490 may be turned or rotated such that the snap element 494 is positioned to prevent movement of the trigger element 490 in the distal direction, as shown in FIG. 59. Thereafter, when activation of the retraction mechanism is desired, for example, when the contents of the fluid barrel 410 has been expelled, the trigger element 490 may be rotated such that the snap element 494 is positioned to permit movement of the trigger element 490 in the distal direction, as shown in FIG. 60.

The trigger element 490 and the retraction barrel 420 include a reuse prevention feature. The retraction barrel 420 includes a first locking element 440 disposed adjacent to its proximal end which engages with a second locking element 450 disposed on the trigger element body 492. The first locking element 440 is shown as an opening 442 on the wall 422 of the retraction barrel 420. It will be understood that the opening may be provided in other forms. The second locking element 450 is shown as an outwardly extending projection 452 disposed on the trigger element body 492. The projection 452 has a proximally facing stop face 454 that prevents movement of the trigger element 492 in the proximal direction and prevents disengagement of the first locking element 440 and the second locking element 450.

The first locking element and the second locking element 450 are positioned on the retraction barrel 420 and the trigger element 490 so they can engage when a force is applied to the trigger rod in the distal direction to activate the retraction mechanism. As shown in FIG. 32, upon application of the force on the trigger element 490 in the distal direction, the projection 452 engages the opening 442.

A reuse prevention feature of the trigger element may be designed to be easily deflectable in the radial direction when the trigger element contacts the interior surface of the retraction barrel 420. In the final position of the first and second locking elements 440, 450, the projection 452 of the trigger element 490 should reach the opening 442 where the projection 452 can re-expand and lock backward motion of the trigger element 490. This will prevent the trigger element 490 from being pulled out of the retraction barrel 420 and activated for multiple activations of the retraction mechanism. By adding this reuse feature to the device, the retraction mechanism can only be activated once, thus preventing re-use after for example exchanging the retracting needle.

A fourth aspect of the present invention pertains to a retractable syringe assembly 500 that includes an alternative retraction mechanism. The retractable syringe assembly 500 is shown in FIGS. 33-37. The syringe assembly 500 includes a dual chamber syringe barrel as otherwise described herein that includes a needle chamber and a fluid chamber. A needle hub assembly 540 according to the needle hub assembly described with reference to FIGS. 8-17, wherein a needle hub 542 encloses a needle cannula support 546, a needle cannula 550 that is attached to the needle cannula support and a biasing element 552 disposed between the needle cannula support 546, needle cannula 550 and the needle hub 542. The needle hub 542, as shown in FIGS. 33-37, include a distal end 553 and a proximal end 554. The distal end 553 may include a body portion 545 having a conical shape and including an opening (not shown) therethrough for receiving the needle cannula 550. The proximal end 554 includes a first retraction portion 555 that extends in the proximal direction from the body 545 and defines a hub cavity for housing the needle cannula support 546, biasing element 552 and the needle cannula, as described above with reference to FIGS. 8-17. The first retraction portion 554 includes a distal end 557 attached to the body portion 545 and a free proximal end 556. The first retraction portion 555 also includes at least one flexible portion 558 having an engaging tab 559 at the proximal end thereof. The engaging tab 559 engages the needle cannula support 546 and exerts a force on the needle cannula support 546 in the distal direction to counteract the force applied by the biasing element 552 in the proximal direction on the needle hub assembly 540.

The trigger element 590 includes a distal end 591 and a proximal end (not shown). The trigger element 590 also includes a trigger element body 592 extending from the distal end 591 to the proximal end, as otherwise described herein, which may include a hollow interior 593 for housing the retracted needle cannula. The trigger element body 592 includes a rib 594 that extends radially outwardly for disengaging the engaging tab 559 from the needle cannula support 546 and releasing the force applied by the engaging tab 559 on the needle hub assembly 540. The trigger element 590 disengages the tab 559 and the needle cannula support 546 upon application of the trigger force by the trigger element, which provides sufficient force in the distal direction on the engaging tab 559 and/or the flexible portion 558 to cause the flexible portion 558 to move outwardly so the engaging tab 559 is no longer engaged with the needle cannula support 546 and the force applied by the biasing element is no longer counteracted. Specifically, the removal of the force applied by the engaging tab 559 on the needle cannula support 546 in the distal direction allows the force applied by the biasing element 552 to move the needle cannula support 546 and needle cannula 550 into the trigger element.

The embodiments described herein may include alternative retraction mechanisms that are disclosed in U.S. Provisional Application Reference Number P-8842, U.S. provisional application Ser. No. 61/366,749, incorporated by reference in its entirety. Specifically, the retraction mechanisms disclosed in FIGS. 7-11, 18-22 and 24-27 of U.S. Provisional Application Reference Number P-8842.

Alternative embodiments of the trigger element are shown in FIGS. 38-57, 57A, 57B and FIGS. 61-66, which may be utilized with the syringe assemblies described herein.

In FIGS. 38, 38A, 38B, 39, 39A, 39B and 54, 54A, 54B and 55, the proximal end of the trigger element has a circular trigger pad that substantially envelopes or surrounds the plunger rod in the open proximal end of the fluid barrel. The trigger element may be coded by indicia such as one or more of indentations, markings or color coding. Upon activation of the trigger element by applying a distal force on the plunger rod, the plunger rod proximal end or thumbpress may be fully nested within the trigger pad.

Figure 40:
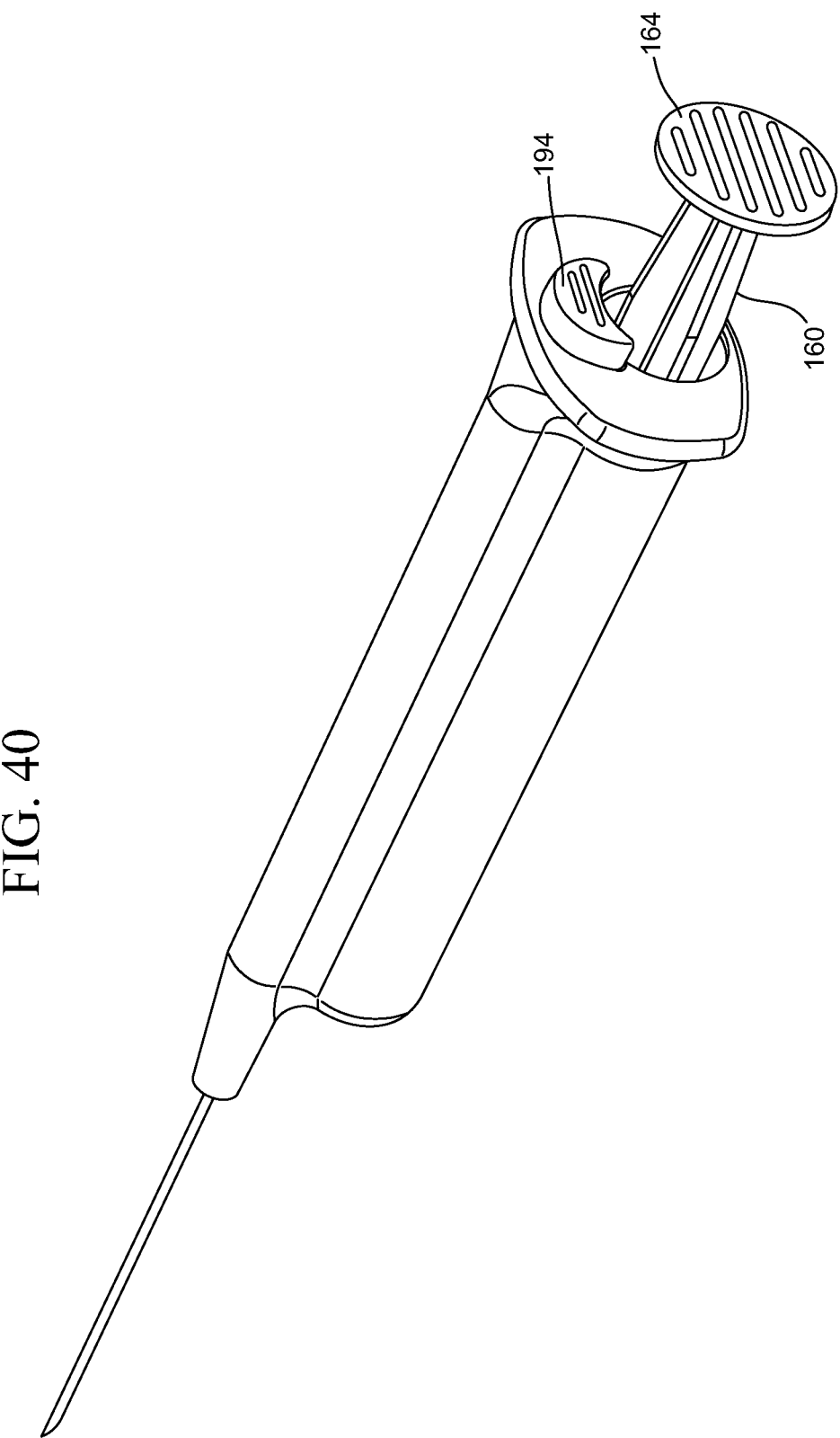
FIG. 40 illustrates a perspective view of a retractable syringe assembly according to one or more embodiments.
Figure 43:
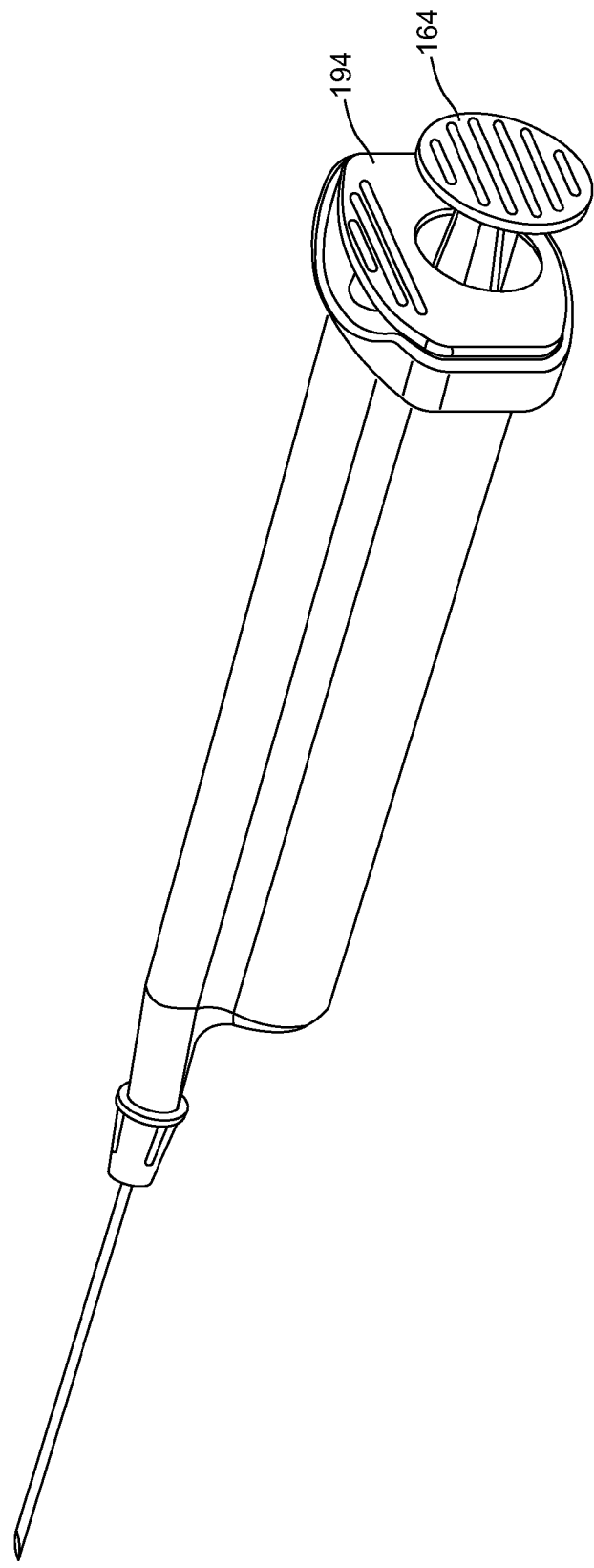
FIG. 43 illustrates a perspective view of a retractable syringe assembly according to one or more embodiments.
Figure 43A:
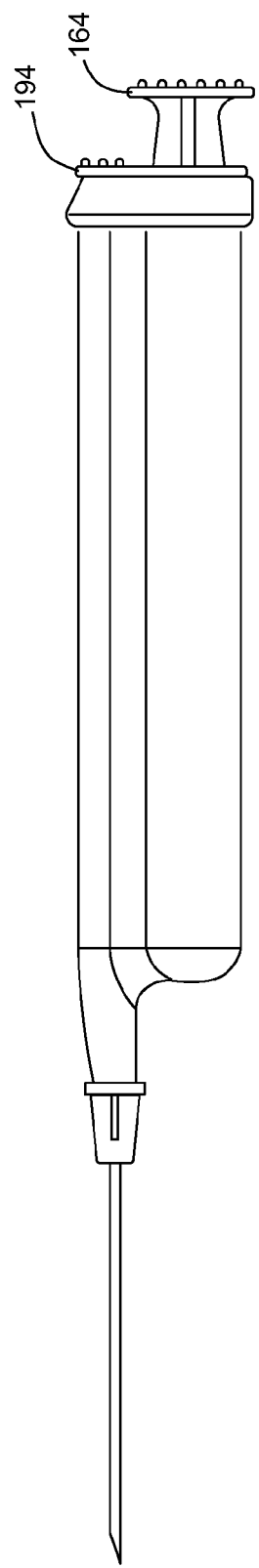
FIG. 43A illustrates a side view of the retractable syringe assembly shown in FIG. 43.
Figure 43B:
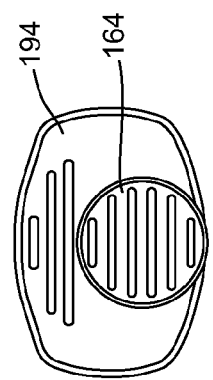
FIG. 43B illustrates a view of the retractable syringe assembly shown in FIG. 43 taken from the proximal end.
Figure 44:
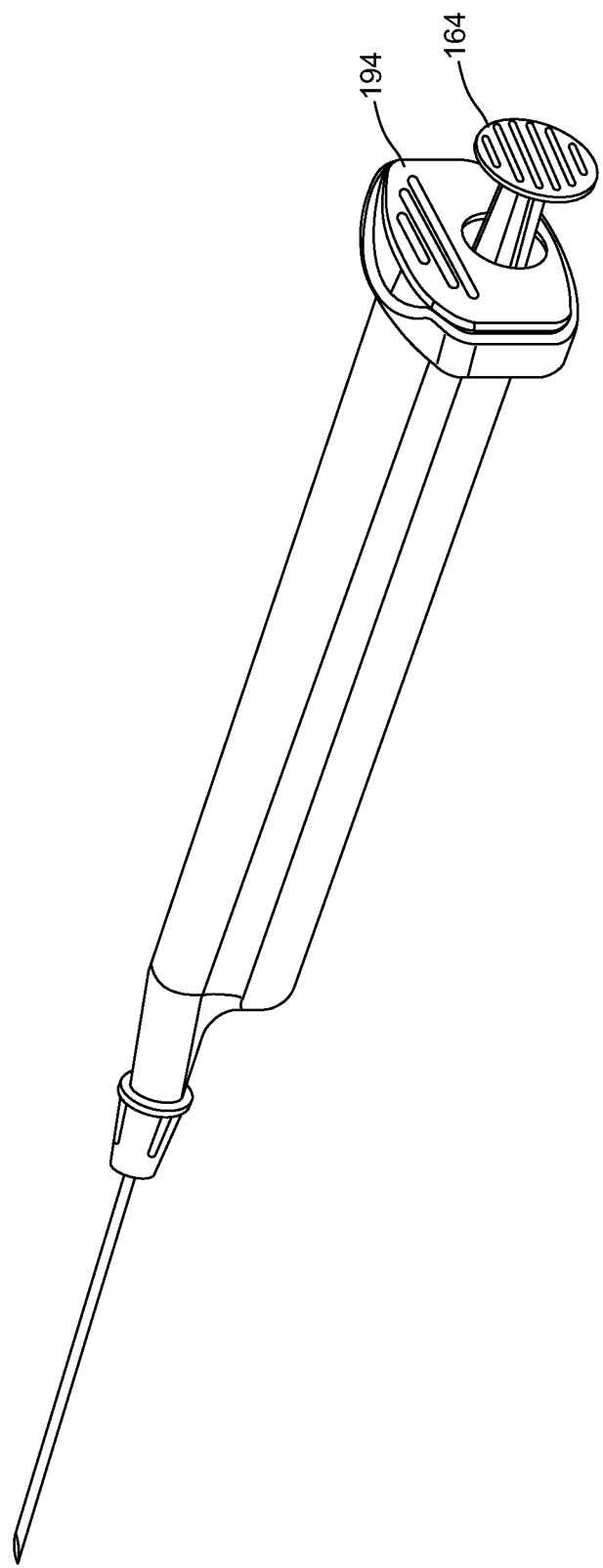
FIG. 44 illustrates a perspective view of a retractable syringe assembly according to one or more embodiments.
Figure 44A:
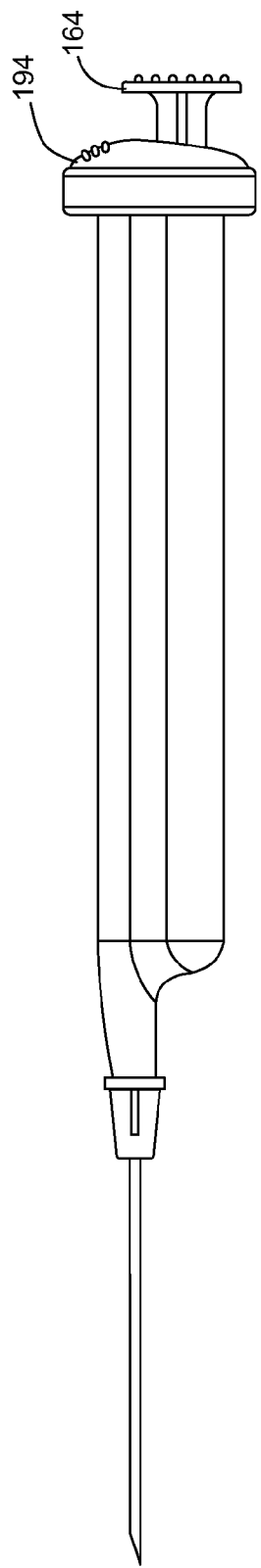
FIG. 44A illustrates a side view of the retractable syringe assembly shown in FIG. 44.
Figure 44B:
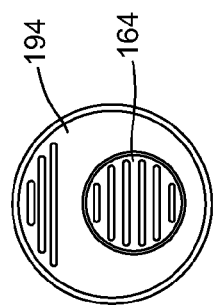
FIG. 44B illustrates a view of the retractable syringe assembly shown in FIG. 44 taken from the proximal end.
Figure 45:
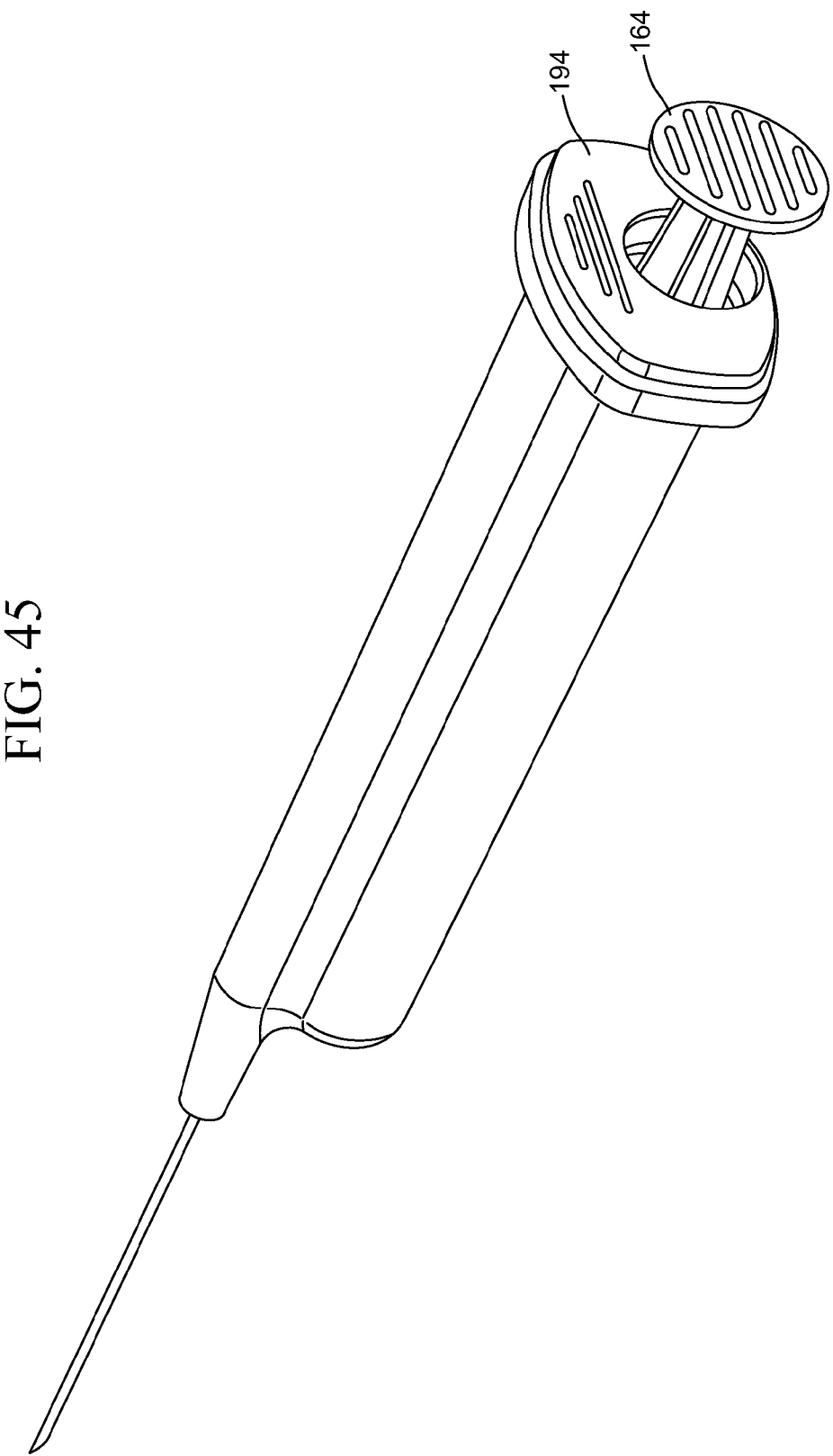
FIG. 45 illustrates a perspective view of a retractable syringe assembly according to one or more embodiments.

FIGS. 40-42 show a design in which the plunger rod engages the trigger element shaped a semicircular element or crescent-shaped element. The plunger rod thumbpress can be depressed to its distal most position, and the user can then activate the trigger element by application of force to the trigger element.

Figure 48:
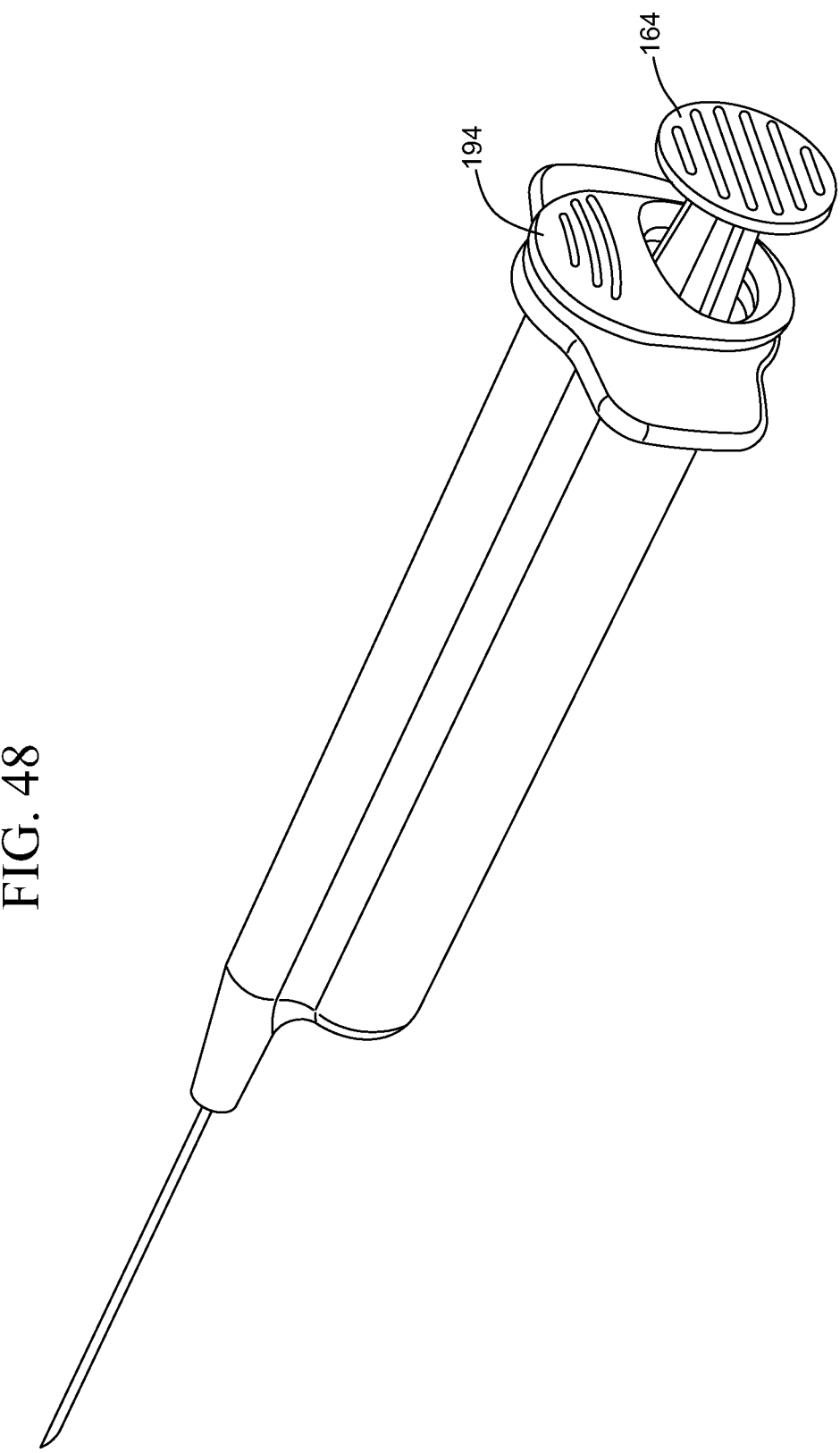
FIG. 48 illustrates a perspective view of a retractable syringe assembly according to one or more embodiments.
Figure 51:
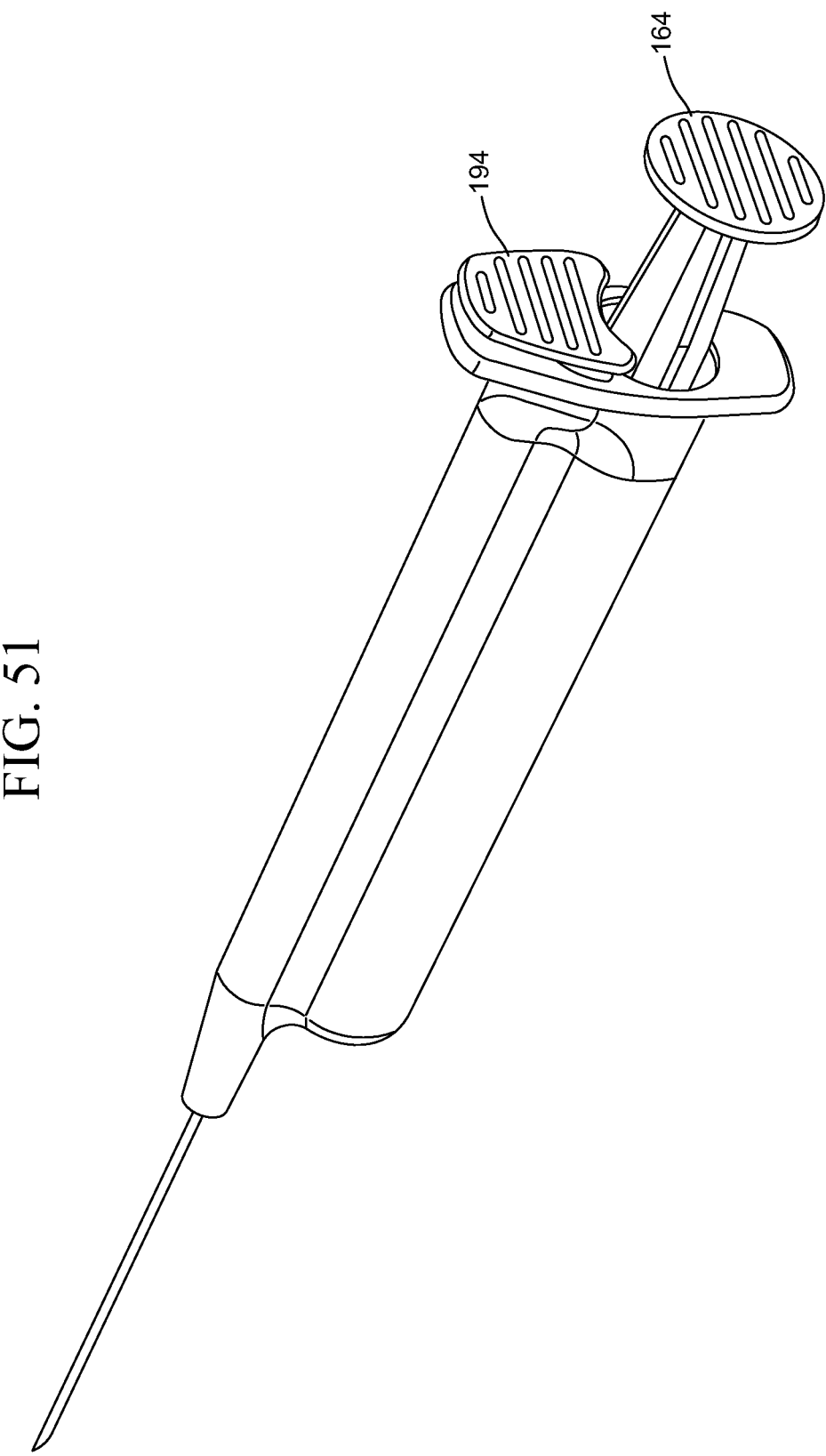
FIG. 51 illustrates a perspective view of a retractable syringe assembly according to one or more embodiments.
Figure 52:
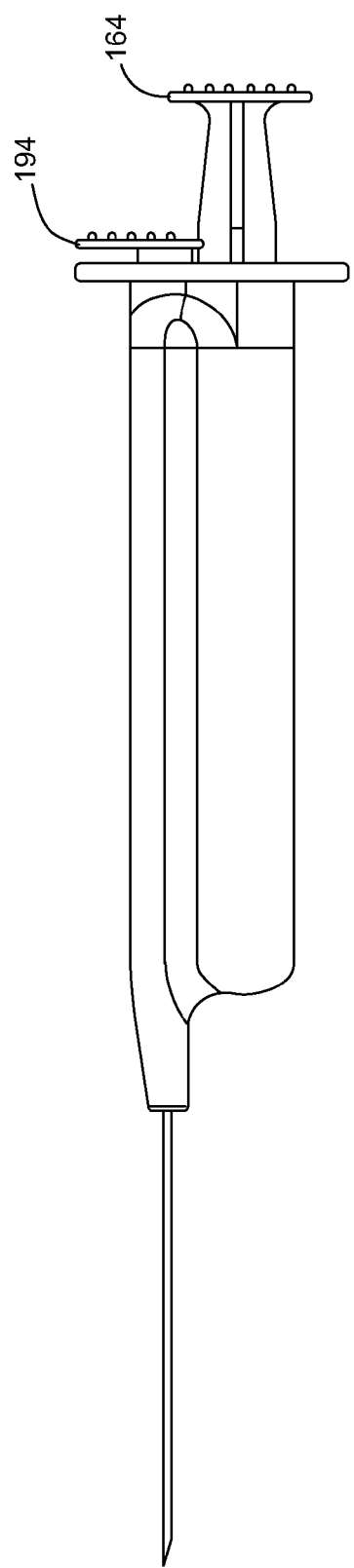
FIG. 52 illustrates a side view of the retractable syringe assembly shown in FIG. 51.
Figure 53:
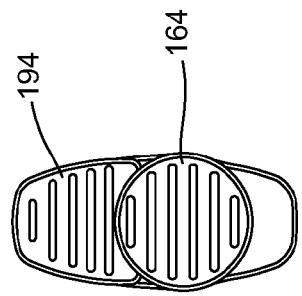
FIG. 53 illustrates a view of the retractable syringe assembly shown in FIG. 52 taken from the proximal end.
Figure 54:
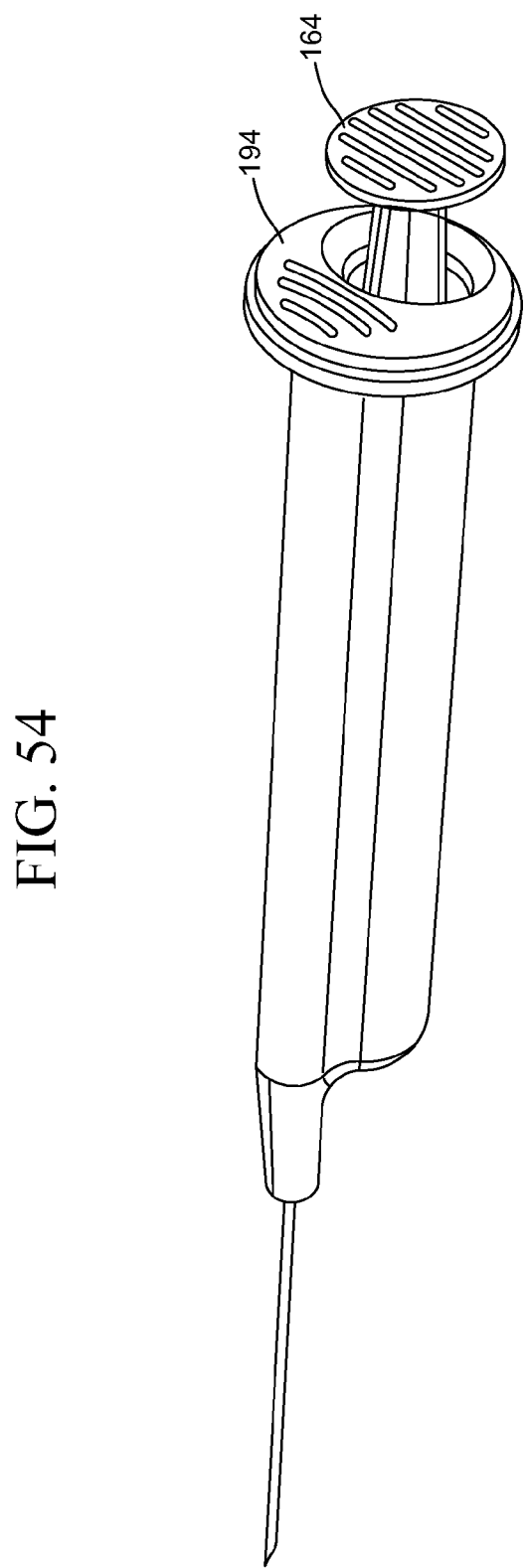
FIG. 54 illustrates a perspective view of a retractable syringe assembly according to one or more embodiments.
Figure 54A:
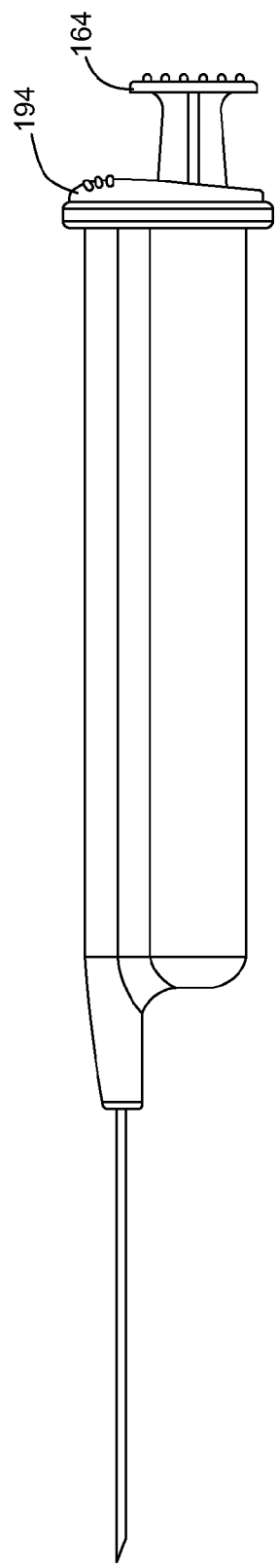
FIG. 54A illustrates a side view of the retractable syringe assembly shown in FIG. 54.
Figure 54B:
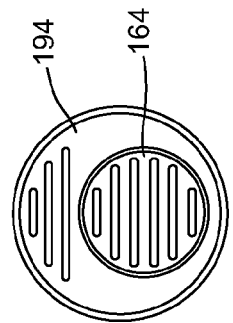
FIG. 54B illustrates a view of the retractable syringe assembly shown in FIG. 54 taken from the proximal end.
Figure 55:
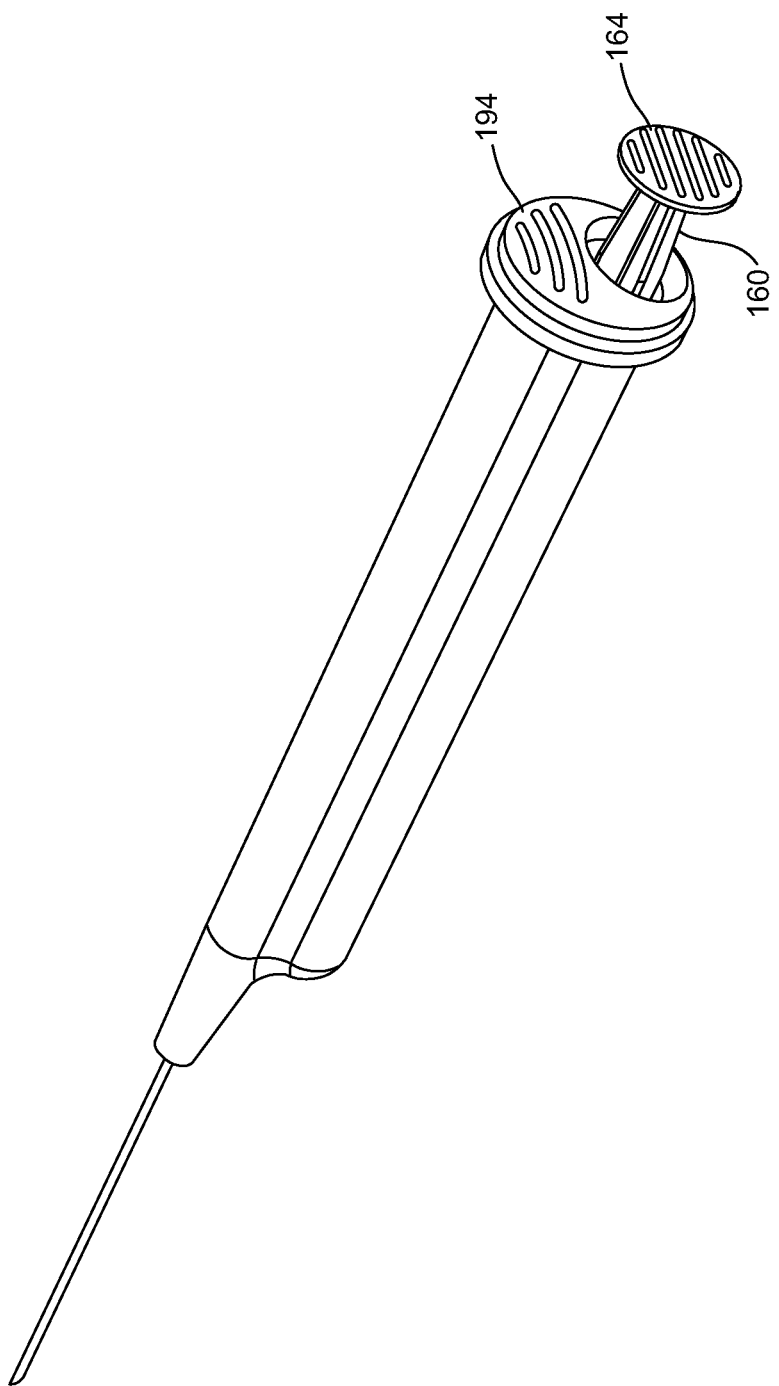
FIG. 55 illustrates a perspective view of a retractable syringe assembly according to one or more embodiments.
Figure 56:
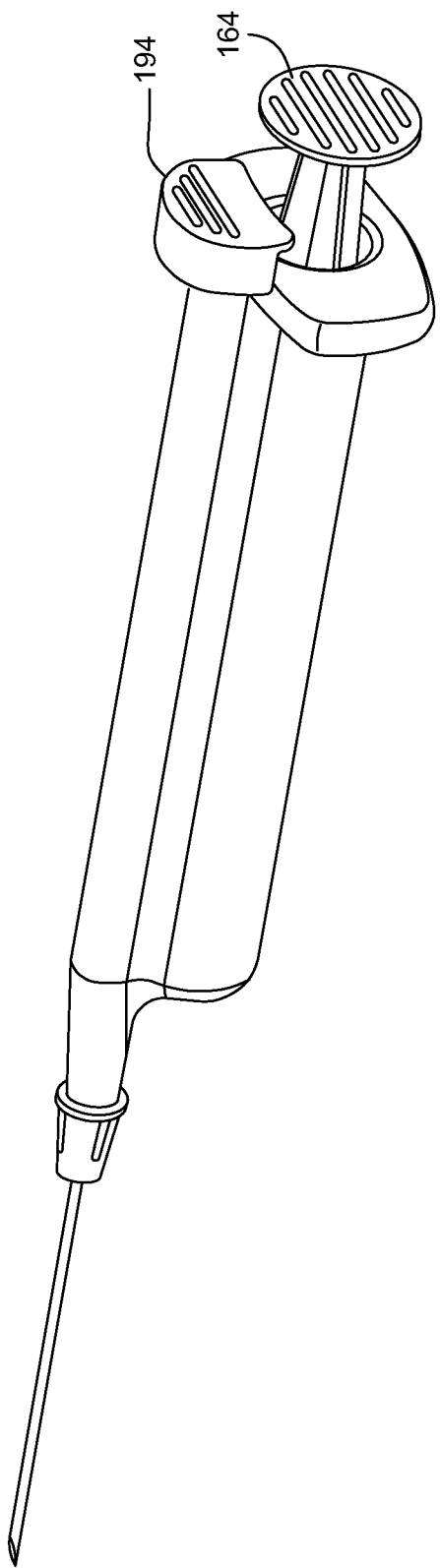
FIG. 56 illustrates a perspective view of a retractable syringe assembly according to one or more embodiments.
Figure 56A:
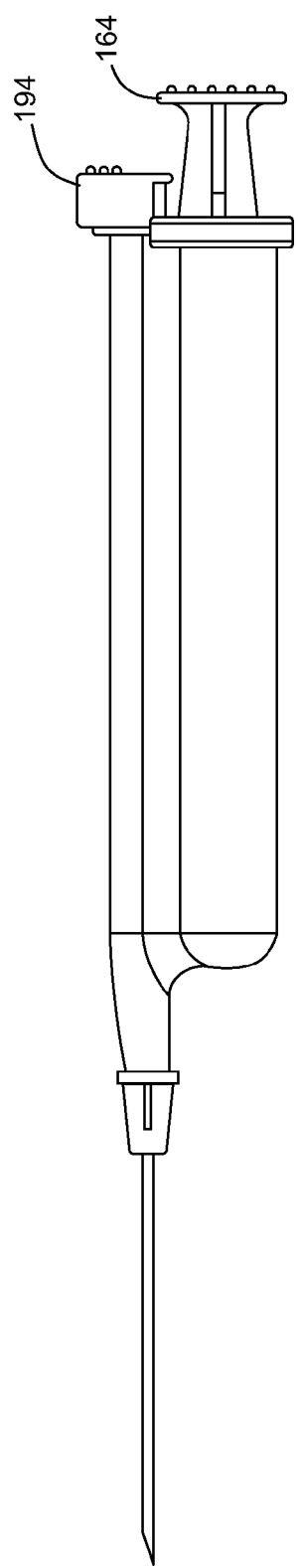
FIG. 56A illustrates a side view of the retractable syringe assembly shown in FIG. 56.
Figure 56B:
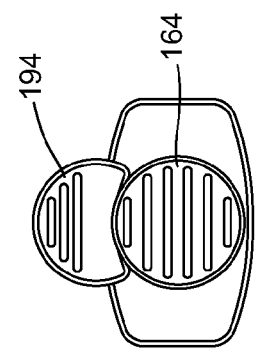
FIG. 56B illustrates a view of the retractable syringe assembly shown in FIG. 56 taken from the proximal end.
Figure 57:
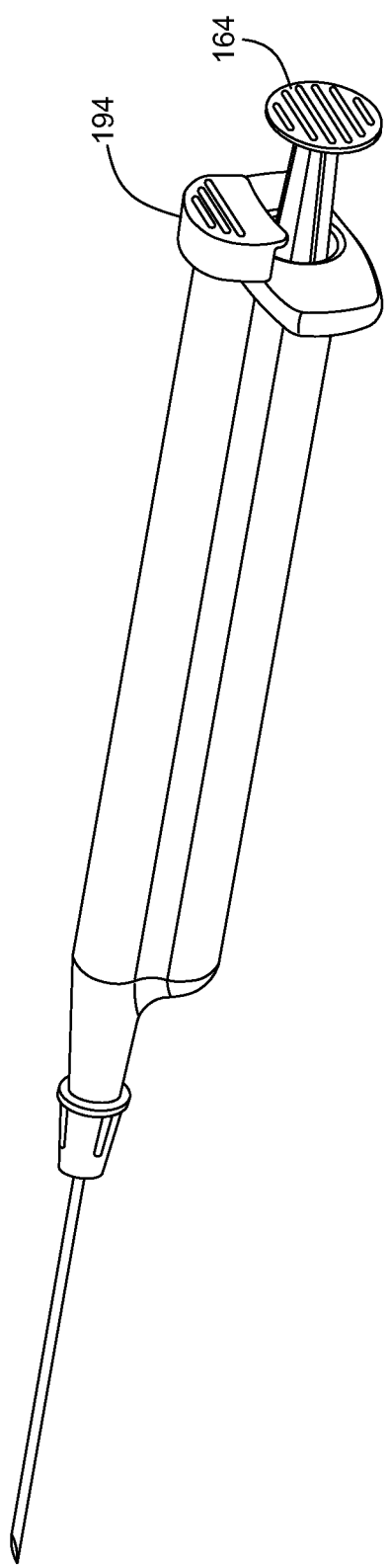
FIG. 57 illustrates a perspective view of a retractable syringe assembly according to one or more embodiments.
Figure 57A:
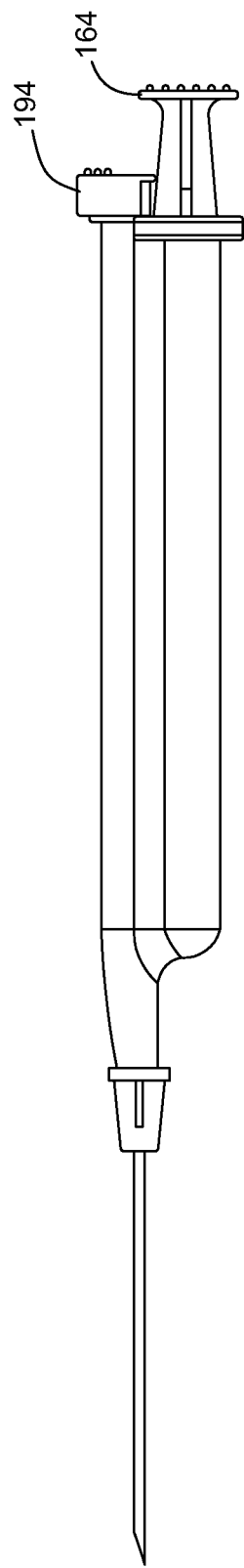
FIG. 57A illustrates a side view of the retractable syringe assembly shown in FIG. 57.
Figure 57B:
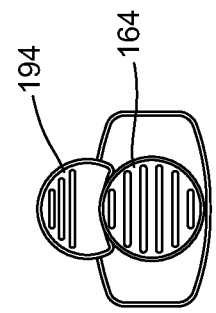
FIG. 57B illustrates a view of the retractable syringe assembly shown in FIG. 57 taken from the proximal end.
Figure 61:
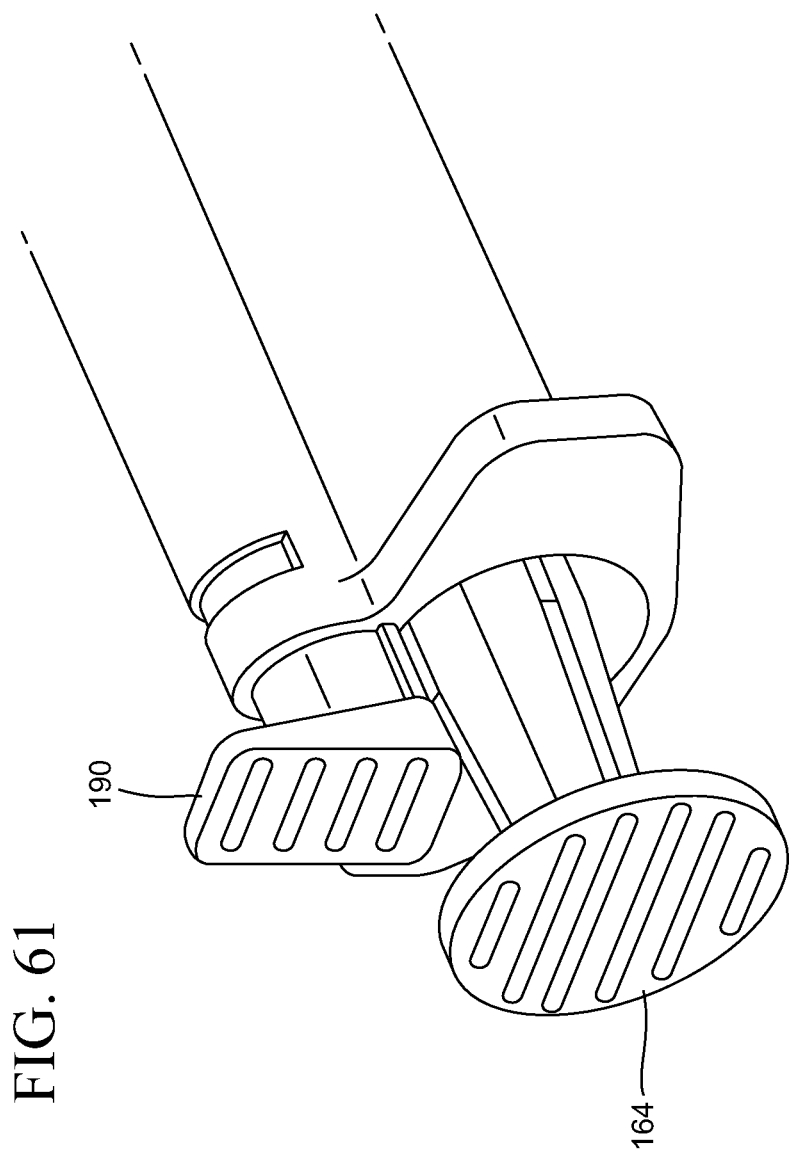
FIG. 61 illustrates a perspective view of the proximal end of a retractable syringe assembly according to one or more embodiments.
Figure 62:
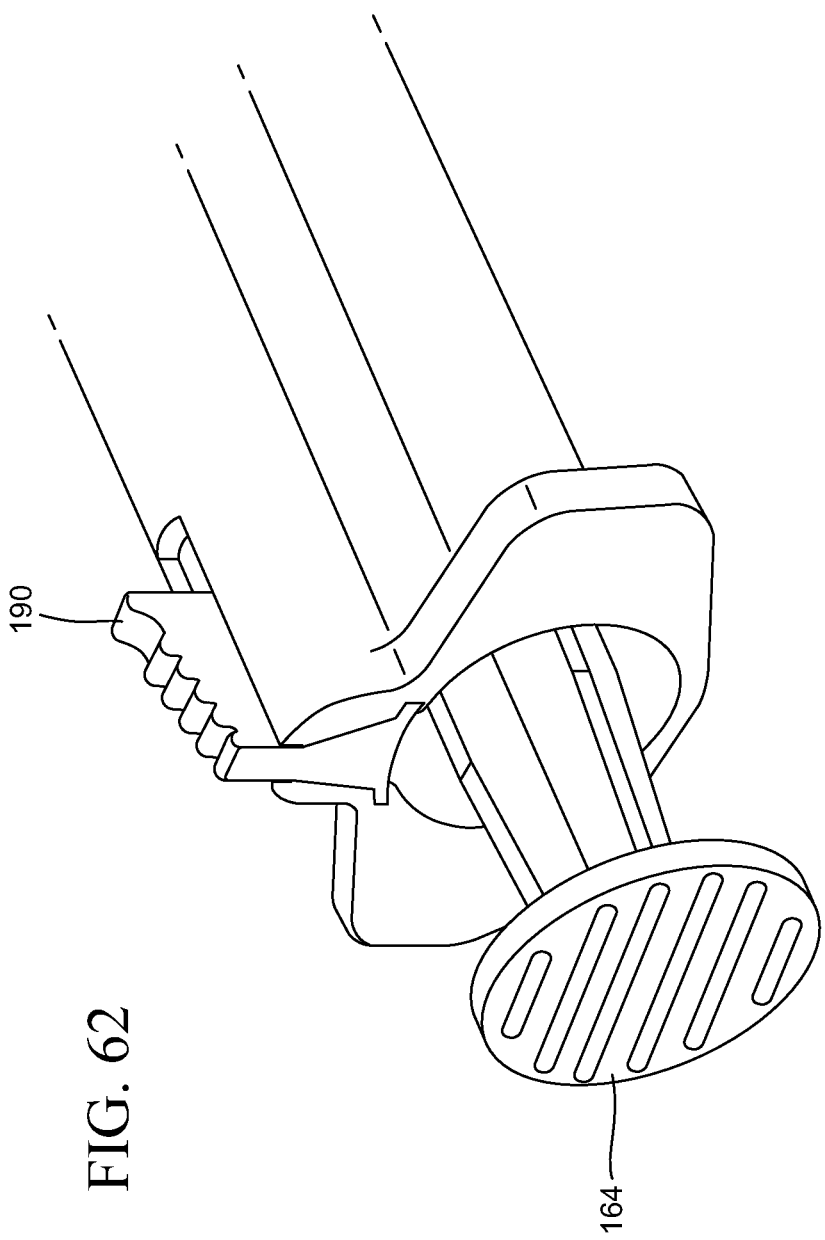
FIG. 62 illustrates a perspective view of the proximal end of a retractable syringe assembly according to one or more embodiments.
Figure 63:
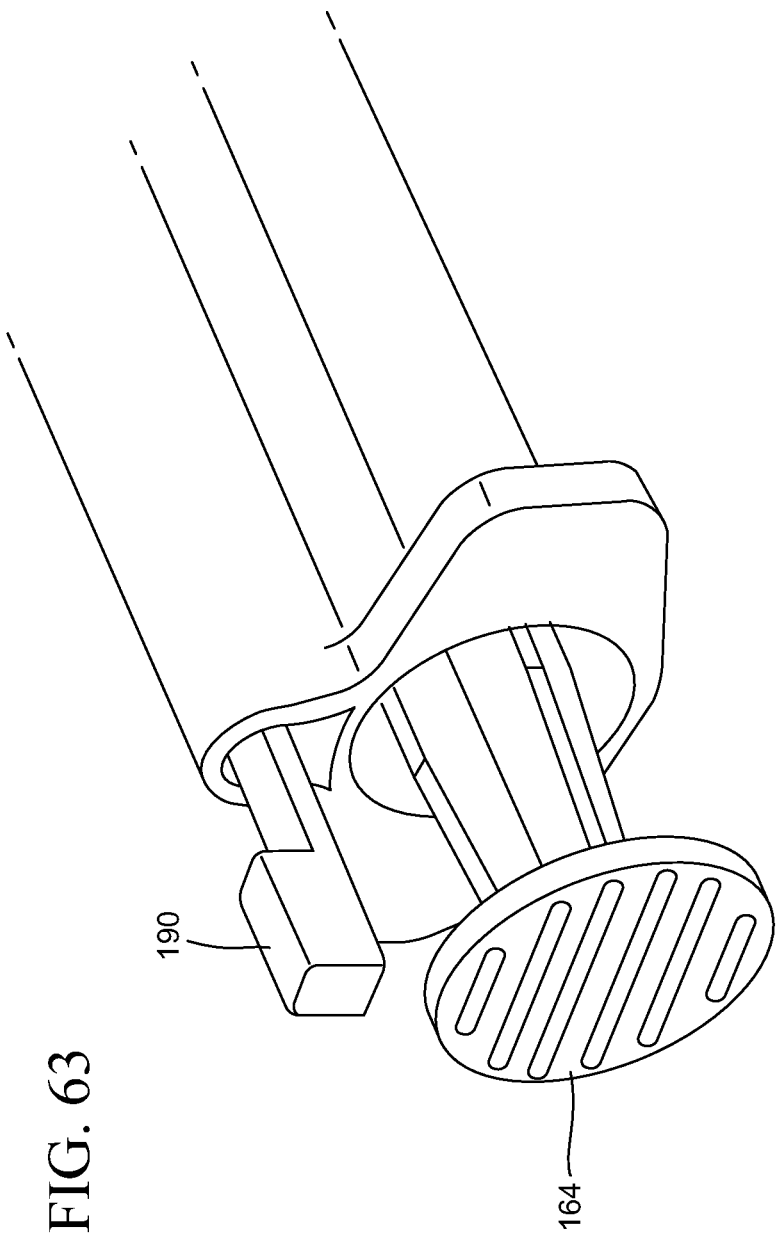
FIG. 63 illustrates a perspective view of the proximal end of a retractable syringe assembly according to one or more embodiments.
Figure 64:
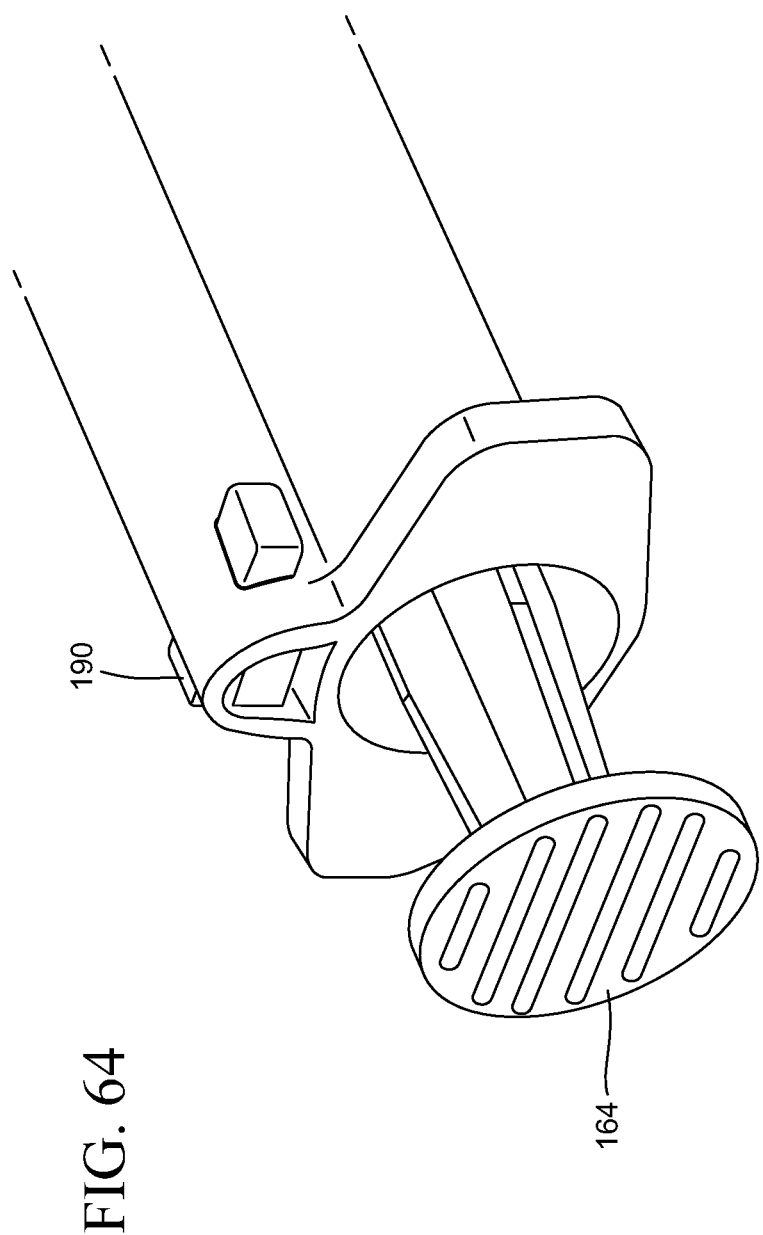
FIG. 64 illustrates a perspective view of the proximal end of a retractable syringe assembly according to one or more embodiments.

FIGS. 43-47 show a design in which proximal end of the trigger element has a substantially rectangular shaped trigger pad with curved edges and the plunger rod can nest within the trigger pad. In FIGS. 48-50, the trigger pad is substantially oval in shape. In FIGS. 51-53, the trigger pad is aligned with the needle cannula on one side of the finger flange of the syringe assembly. In FIGS. 56, 57, 57A and 57B, the trigger element has a trigger pad that is aligned with the needle cannula and needle chamber, and the trigger pad extends outwardly from the body of the needle chamber. FIG. 61 shows a configuration in which the trigger element is a small tab at the end of the needle chamber. FIG. 62 shows a trigger element as a tab that can be activated by applying a force in the distal direction. The trigger element has a gripping surface in the form of a plurality of spaced ribs. FIG. 63 shows an alternative trigger element design in which the trigger element is in the form of a block-shaped that can be activated by the user. FIG. 64 shows a button embedded in the proximal end of the needle barrel that can be activated by the user by pressing or squeezing the button to cause the needle to retract.

Figure 65:
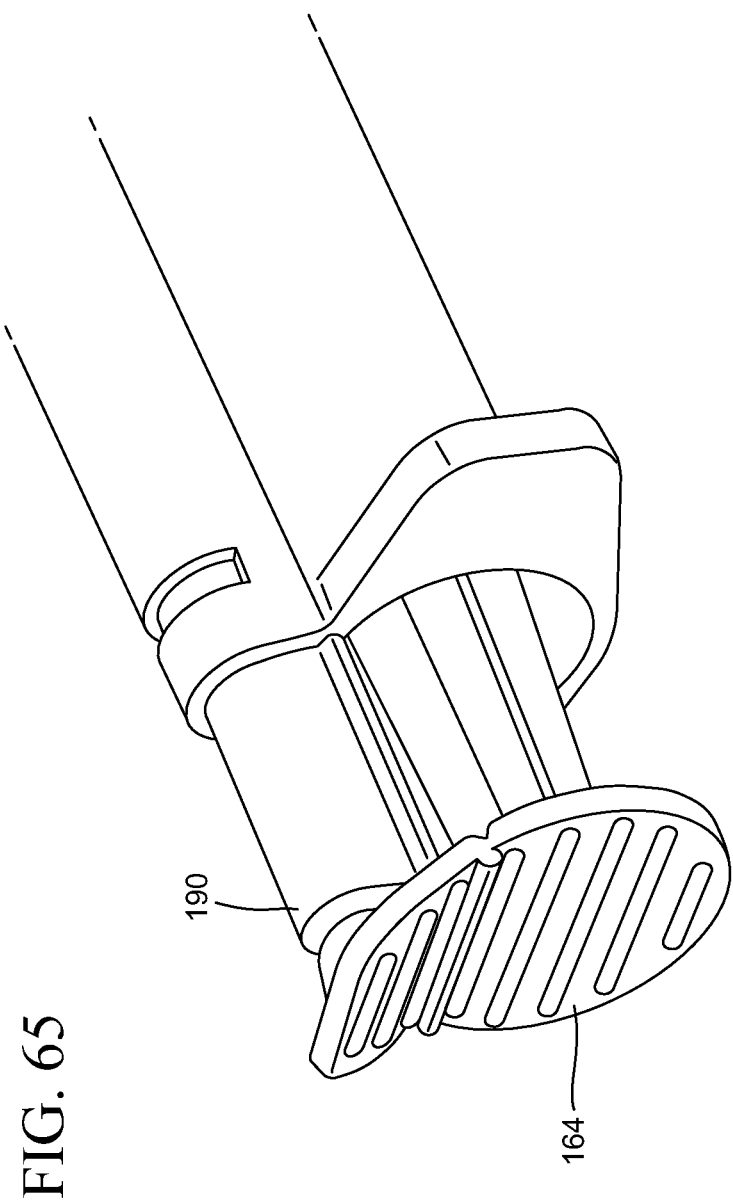
FIG. 65 illustrates a perspective view of the proximal end of a retractable syringe assembly according to one or more embodiments.
Figure 66:
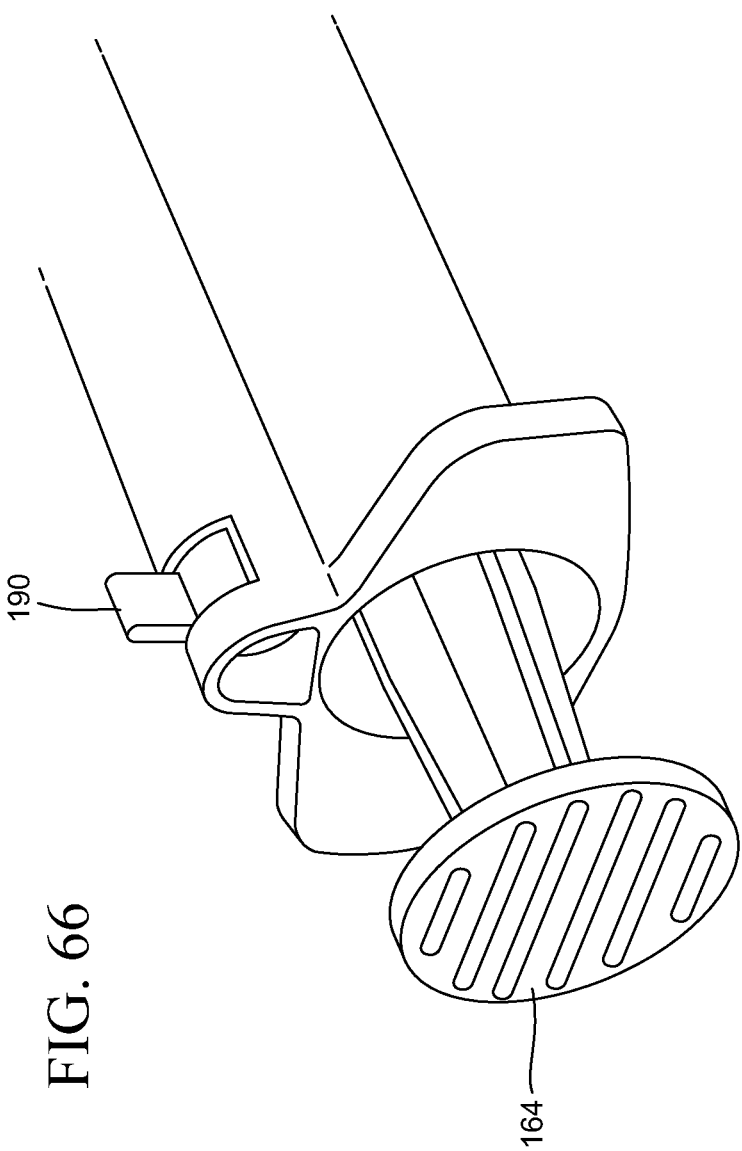
FIG. 66 illustrates a perspective view of the proximal end of a retractable syringe assembly according to one or more embodiments.

FIG. 65 shows a plunger rod thumbpress that has hinged portion that can be moved by applying distal force to the hinged portion to activate the trigger element an retraction mechanism. FIG. 66 shows a trigger element that is somewhat similar to FIG. 64, except that the trigger element is in the form of a toggle type element that can be radially moved to activate the retraction mechanism.

In another embodiment of the present invention, a method for aspirating and expelling a liquid from a syringe assembly of the present invention is provided comprising aligning the trigger guard to prevent movement of the trigger element in the distal direction. A pre-selected amount of liquid is then aspirated into the fluid chamber by inserting the needle cannula into the liquid and applying a force on the plunger rod in a proximal direction. The liquid from the fluid chamber is expelled by applying a force on the plunger rod in the distal direction. The needle cannula is retracted into the retraction barrel by aligning the trigger guard to permit movement of the trigger element in the distal direction and applying a force on the trigger guard in the distal direction to provide the trigger force causing the needle cannula to retract into the retraction barrel.

In another embodiment of the present invention, a method for aspirating and expelling a liquid from a syringe assembly of the present invention is provided comprising aspirating a pre-selected amount of liquid into the fluid chamber by inserting the needle cannula into the liquid and applying a force on the plunger rod in a proximal direction. The liquid from the fluid chamber is then expelled by applying a force on the plunger rod in the distal direction. The plunger rod is locked within the fluid barrel by applying a continuous force on the plunger rod in the distal direction causing the protrusion of the plunger rod to move distally past the retaining ring of the fluid barrel. The needle cannula is retracted into the retraction barrel by aligning the trigger guard to permit movement of the trigger element in the distal direction and applying a force on the trigger guard in the distal direction to provide the trigger force causing the needle cannula to retract into the retraction barrel.

In another embodiment of the present invention, a method for aspirating and expelling a liquid from a syringe assembly of the present invention is provided comprising providing a syringe barrel including a fluid barrel and a retraction barrel in fluid communication, the fluid barrel including a plunger rod attached to a stopper for aspirating and expelling liquid from the fluid barrel and a retraction barrel including a needle hub, needle cannula with an opening and a trigger element for providing a trigger force causing the needle cannula to retract into the retraction barrel. The opening of the needle cannula is submerged in a liquid and the fluid barrel of the syringe is filled with the liquid by applying a force to the plunger rod in a proximal direction. The liquid from the fluid barrel is expelled by applying a force to the plunger rod in a distal direction. The needle cannula is then retracted into the retraction barrel by applying a force to the trigger element in the distal direction to provide the trigger force.

In another embodiment of the present invention, a method for aspirating and expelling a liquid from a syringe assembly of the present invention is provided further comprising locking the plunger rod in the fluid barrel after expelling the liquid from the fluid barrel.

In another embodiment of the present invention, a method for aspirating and expelling a liquid from a syringe assembly of the present invention is provided wherein the force applied to the plunger rod is oriented along an axis that is parallel to the axis along which the force applied to the trigger element is oriented.

In another embodiment of the present invention, a method for aspirating and expelling a liquid from a syringe assembly of the present invention wherein the force applied to the plunger rod to expel the liquid is less than the force applied to the trigger element.

Reference throughout this specification to "one embodiment," "certain embodiments," "one or more embodiments" or "an embodiment" means that a particular feature, structure, material, or characteristic described in connection with the embodiment is included in at least one embodiment of the invention. Thus, the appearances of the phrases such as "in one or more embodiments," "in certain embodiments," "in one embodiment" or "in an embodiment" in various places throughout this specification are not necessarily referring to the same embodiment of the invention. Furthermore, the particular features, structures, materials, or characteristics may be combined in any suitable manner in one or more embodiments.

Although the invention herein has been described with reference to particular embodiments, it is to be understood that these embodiments are merely illustrative of the principles and applications of the present invention. It will be apparent to those skilled in the art that various modifications and variations can be made to the method and apparatus of the present invention without departing from the spirit and scope of the invention. Thus, it is intended that the present invention include modifications and variations that are within the scope of the appended claims and their equivalents.

What is claimed is:

1. A syringe assembly comprising:
    a fluid barrel including a sidewall having an inside surface defining a fluid chamber for retaining fluid and having a first cross-sectional width, an open proximal end and a distal end including a distal wall;
    a plunger rod disposed within the fluid chamber comprising a distal end, a proximal end, a plunger rod body extending from the distal end to the proximal end, and a stopper disposed at the distal end of the plunger rod for forming a fluid-tight seal with the inside surface of the barrel;
    a retraction barrel disposed adjacent to the sidewall of the fluid barrel, the retraction barrel including a wall having an interior surface defining a needle chamber, an open proximal end, an open distal end including a barrier wall, an aperture between the wall of the retraction barrel and the sidewall of the fluid barrel permitting fluid communication between the fluid chamber and the needle chamber and a needle hub assembly comprising a needle hub, a needle cannula attached to the needle hub, the needle cannula being in fluid communication with the aperture and biased to move in a proximal direction; and
    a trigger element disposed within the needle chamber and moveable within the retraction barrel independently from the plunger rod, wherein the trigger element includes a proximal end, a free and open distal end that provides the trigger force, and a trigger element body extending from the proximal end to the distal end and including an interior surface defining a hollow interior, the trigger element providing a trigger force causing the needle cannula to retract into the retraction barrel.

2. The syringe assembly of claim 1, wherein the needle chamber has a cross sectional width that is less than the first cross-sectional width.

3. The syringe assembly of claim 1, wherein the needle cannula is retracted into the retraction barrel, it is housed within the hollow interior of the trigger element.

4. The syringe assembly of claim 1, wherein the inside surface of the fluid barrel sidewall includes a retaining ring adjacent to the proximal end defining a second cross-sectional width that is less than the first cross-sectional width, and the plunger rod body includes a flexible protrusion having a cross-sectional width greater than the cross-sectional width of the inside surface of the fluid barrel at the retaining ring and a frangible portion.

5. The syringe assembly of claim 4, wherein contact between the stopper and the distal wall of the barrel causes the protrusion to advance distally past the retaining ring in the fluid barrel and lock the plunger rod in the fluid barrel to prevent reuse of the syringe assembly.

6. The syringe assembly of claim 5, wherein continuous application of a force on the plunger rod in the proximal direction after the protrusion has advanced distally past the retaining ring causes the frangible portion to break.

7. The syringe assembly of claim 4, wherein the distal end of the plunger rod includes a stopper-engaging portion and the stopper is attached to the stopper-engaging portion of the plunger rod, the stopper being distally and proximally movable relative to the stopper-engaging portion for a pre-selected axial distance such that when a force is applied to the plunger rod in the distal direction and the distal end of the stopper is in contact with the distal wall of the barrel, the protrusion is permitted to advance distally past the retaining ring in the fluid barrel and lock the plunger rod in the fluid barrel to prevent reuse of the syringe assembly.

8. The syringe assembly of claim 7, wherein continuous application of a force on the plunger rod in the proximal direction after the protrusion has advanced distally past the retaining ring causes the frangible portion to break.

9. The syringe assembly of claim 1, wherein the needle hub body assembly is disposed at the open distal end of the retraction barrel and includes a frangible element for exerting a force on the needle hub assembly in the distal direction.

10. The syringe assembly of claim 9, wherein the needle cannula is biased by a spring disposed between the needle hub and the barrier wall that exerts a force on the needle hub in a proximal direction.

11. The syringe assembly of claim 9, wherein application of a force in the distal direction to the trigger element provides the trigger force on the needle hub assembly to break the frangible element so the needle cannula is retracted into the retraction barrel.

12. The syringe assembly of claim 11, wherein the inside surface of the fluid chamber sidewall includes a retaining ring adjacent to the proximal end defining a second cross-sectional width that is less than the first cross-sectional width and the plunger rod body includes a flexible protrusion having a cross-sectional width greater than the cross-sectional width of the barrel at the rib and a frangible portion.

13. The syringe assembly of claim 12, wherein contact between the stopper and the distal wall of the barrel causes the protrusion to advance distally past the rib in the barrel and lock the plunger rod in the barrel to prevent reuse of the syringe assembly.

14. The syringe assembly of claim 13, wherein continuous application of a force on the plunger rod in the proximal direction after the protrusion has advanced distally past the rib causes the frangible portion to break.

15. The syringe assembly of claim 12, wherein the distal end of the plunger rod includes a stopper-engaging portion and the stopper is attached to the stopper-engaging portion of the plunger rod, the stopper being distally and proximally movable relative to the stopper-engaging portion for a pre-selected axial distance such that when a force is applied to the plunger rod in the distal direction and the distal end of the stopper is in contact with the distal wall of the barrel, the protrusion is permitted to advance distally past the rib in the barrel and lock the plunger rod in the barrel to prevent reuse of the syringe assembly.

16. The syringe assembly of claim 15, wherein continuous application of a force on the plunger rod in the proximal direction after the protrusion has advanced distally past the rib causes the frangible portion to break.

17. The syringe assembly of claim 1, wherein the open distal end of the retraction barrel comprises a securing element for securing the needle hub assembly to the retraction barrel and the needle hub assembly includes an attachment element that engages the securing element, the engagement of the attachment element and the securing element being activated by a needle shield disposed on the needle hub.

18. The syringe assembly of claim 17, wherein engagement of the securing element and the attachment element permits fluid communication between the aperture and the needle cannula.

19. The syringe assembly of claim 17, wherein the needle shield may be removed from the needle hub upon engagement of the attachment element and the securing element.

20. The syringe assembly of claim 17, wherein the securing element of the retraction barrel comprises at least one opening in the wall of the retraction barrel extending in a distal direction from the open distal end and the attachment element comprises at least one radially outwardly extending tab disposed on the needle hub for engaging the at least one opening.

21. The syringe assembly of claim 20, wherein the needle hub comprises an open conduit for permitting fluid communication between the needle cannula and the aperture and the engagement of the tab of the needle hub and the opening of the retraction barrel permits alignment of the open conduit and the aperture.

22. The syringe assembly of claim 17, wherein the needle hub comprises a distal end, a proximal end and a hub body extending from the distal end to the proximal end, the hub body including an outside surface and at least one finger element disposed along an outside surface, the finger element extending outwardly from the outside surface of the hub body and including a distal end attached the outside surface of the needle hub and a free proximal end that is unattached to the needle hub.

23. The syringe assembly of claim 22, wherein the needle shield comprises a closed distal end, an open proximal end and a hollow body defining an cavity for receiving the needle hub, the hollow body including an interior surface comprising a plurality of detents that extend inwardly and engage the at least one finger of the needle hub to rotate the needle hub with respect to the securing element to attach the needle hub to the open distal end of the retraction barrel.

24. The syringe assembly of claim 23, wherein the plurality of detents apply a rotational force to the at least one finger or the needle hub to engage the finger and permit rotation of the needle hub.

* * * * *